(12) United States Patent
Moffat et al.

(10) Patent No.: US 8,003,695 B2
(45) Date of Patent: Aug. 23, 2011

(54) IKK-BETA SERINE-THREONINE PROTEIN KINASE INHIBITORS

(75) Inventors: David Festus Charles Moffat, Oxfordshire (GB); Stephen John Davies, Abingdon (GB); Michael Hugh Charlton, Abingdon (GB); Simon Christopher Hirst, Abingdon (GB); Stuart Thomas Onions, Nottingham (GB); Jonathan Gareth Williams, Nottingham (GB)

(73) Assignee: Chroma Therapeutics Ltd. (GB)

( * ) Notice: Subject to any disclaimer, the term of this patent is extended or adjusted under 35 U.S.C. 154(b) by 281 days.

(21) Appl. No.: 12/513,206

(22) PCT Filed: Oct. 29, 2007

(86) PCT No.: PCT/GB2007/004114
§ 371 (c)(1),
(2), (4) Date: May 1, 2009

(87) PCT Pub. No.: WO2008/053182
PCT Pub. Date: May 8, 2008

(65) Prior Publication Data
US 2010/0087515 A1    Apr. 8, 2010

(30) Foreign Application Priority Data

Nov. 1, 2006  (GB) .................................. 0621720.2
Aug. 9, 2007  (GB) .................................. 0715470.1

(51) Int. Cl.
*A61K 31/381*    (2006.01)
*C07D 333/38*    (2006.01)

(52) U.S. Cl. .......................................... 514/534; 560/42
(58) Field of Classification Search .................. 514/534; 560/42
See application file for complete search history.

(56) References Cited

FOREIGN PATENT DOCUMENTS

| WO | WO 03/010158 A | 2/2003 |
| WO | WO 2004/063186 A | 7/2004 |

OTHER PUBLICATIONS

International Search Report of PCT/GB2007/004114 dated Feb. 19, 2009.

*Primary Examiner* — Sreeni Padmanabhan
*Assistant Examiner* — Sahar Javanmard
(74) *Attorney, Agent, or Firm* — Banner & Witcoff, Ltd.

(57) ABSTRACT

Compounds of formula (IA) or (IB) are inhibitors of IkB kinase (IKK) activity, and are useful in the treatment of autoimmune and inflammatory diseases: Formula (A) and (B) wherein $R_7$ is hydrogen or optionally substituted ($C_1$-$C_6$) alkyl; ring A is an optionally substituted aryl or heteroaryl ring of 5-13 ring atoms; Z is (a) a radical of formula $R_1R_2CHNH$—Y-$L^1$-$X^1$—$(CH_2)_z$— wherein: z is 0 or 1; R1 is a carboxylic acid group (—COOH), or an ester group which is hydrolysable by one or more intracellular esterase enzymes to a carboxylic acid group; R2 is the side chain of a natural or non-natural alpha amino acid; Y is a bond, —C(=O)—, —S(=P)2-, —C(=O)O—, —C(=O)NR3-, —C(=S)—NR3, —C(=NH)—NR3 or —S(=O)2NR3— wherein $R_3$ is hydrogen or optionally substituted $C_1$-$C_6$ alkyl; L is a divalent linker radical of formula -$(Alk^1)_m(Q)(Alk^2)_p$- wherein m, n, p, Q, $Alk^1$ and $Alk^2$ are as defined in the claims.

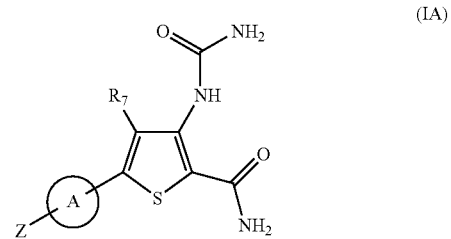

(IA)

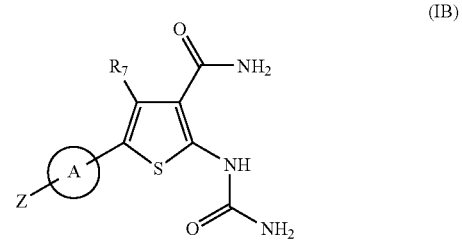

(IB)

11 Claims, No Drawings

IKK-BETA SERINE-THREONINE PROTEIN KINASE INHIBITORS

CROSS REFERENCE TO RELATED APPLICATIONS

This application is a National Stage application of co-pending PCT application PCT/GB2007/004114 filed Oct. 29, 2007, which claims the benefit of Great Britain application number 0621720.2 filed Nov. 1, 2006 and Great Britain application number 0715470.1 filed Aug. 9, 2007. These applications are incorporated herein by reference in their entireties.

This invention relates to thiophene carboxamides characterised by the presence in the molecule of an amino acid ester group, to compositions containing them, to processes for their preparation and to their use in medicine as IKK inhibitors for the treatment of autoimmune and inflammatory diseases, including chronic obstructive pulmonary disease, asthma, rheumatoid arthritis, psoriasis, inflammatory bowel disease, Crohn's disease, ulcerative colitis, multiple sclerosis, diabetes, atopic dermatitis, graft versus host disease, systemic lupus erythematosus. The compounds are also of use in the treatment of proliferative disease states, such as cancers.

BACKGROUND OF THE INVENTION

The expression of many pro-inflammatory genes is regulated by the transcriptional activator nuclear factor-kB (NF-kB). These transcription factors have been suspected since their discovery to play a pivotal role in chronic and acute inflammatory diseases. It now seems that aberrant regulation of NF-kB could also underlie autoimmune diseases and different types of cancer.

Examples of genes dependent on the activation of NF-kB include: the cytokines tumor necrosis factor TNF-α, interleukin (IL)-6, IL-8 and IL-1β; the adhesion molecules E-selectin, intercellular adhesion molecule (ICAM)-1 and vascular cell adhesion molecule (VCAM)-1; and the enzymes nitric oxide synthase (NOS) and cyclooxygenase (COX)-2. NF-kB normally resides in the cytoplasm of unstimulated cells as an inactive complex with a member of the IkB inhibitory protein family. However, upon cellular activation, IkB is phosphorylated by the IkB kinase (IKK) and is subsequently degraded. Free NF-kB then translocates to the nucleus where it mediates pro-inflammatory gene expression.

There are three classical IkB's: IkBα, IkBβ and IkBε; all of which require the phosphorylation of two key serine residues before they can be degraded. Two major enzymes IKK-α and IKK-β appear to be responsible for IkB phosphorylation. Dominant-negative (DN) versions of either of these enzymes (where ATP binding is disabled by the mutation of a key kinase domain residue) were found to suppress the activation of NF-kB by TNF-α, IL-1β and LPS. Importantly IKK-β DN was found to be a far more potent inhibitor than IKK-α DN (Zandi, E *Cell*, 1997, 91, 243). Furthermore, the generation of IKK-α and IKK-β deficient mice established the requirement of IKK-β for activation of NF-kB by proinflammatory stimuli and reinforced the dominant role of IKK-β suggested by biochemical data. Indeed it was demonstrated that IKK-α was dispensable for NF-kB activation by these stimuli (Tanaka, M.; *Immunity* 1999, 10, 421). Thus, inhibition of IKK-β represents a potentially attractive target for modulation of immune function and hence the development of drugs for the treatment of auto-immune diseases.

BRIEF DESCRIPTION OF THE INVENTION

This invention makes available a class of thiophene carboxamides which are potent and selective inhibitors of IKK isoforms, particularly IKKβ. The compounds are thus of use in medicine, for example in the treatment of a variety of proliferative disease states, such as conditions related to the hyperactivity of IKK, as well as diseases modulated, by the NF-kB cascade. In addition, the compounds of the invention are useful for the treatment of stroke, osteoporosis, rheumatoid arthritis and other inflammatory disorders. The compounds are characterised by the presence in the molecule of an amino acid motif or an amino acid ester motif which is hydrolysable by an intracellular carboxylesterase. Compounds of the invention having the lipophilic amino acid ester motif cross the cell membrane, and are hydrolysed to the acid by the intracellular carboxylesterases. The polar hydrolysis product accumulates in the cell since it does not readily cross the cell membrane. Hence the IKK inhibitory activity of the compound is prolonged and enhanced within the cell. The compounds of the invention are related to the IKK inhibitors encompassed by the disclosure in International Patent Application No. WO 2004063186 but differ therefrom in that the present compounds have the amino acid ester motif referred to above.

DETAILED DESCRIPTION OF THE INVENTION

According to the present invention there is provided compound of formula (IA) or (IB), or a salt, N-oxide, hydrate or solvate thereof:

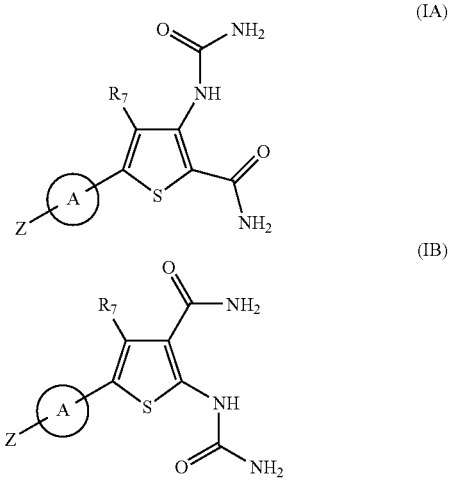

wherein $R_7$ is hydrogen or optionally substituted $(C_1-C_6)$alkyl;

ring A is an optionally substituted aryl or heteroaryl ring or ring system of 5-13 ring atoms;

Z is (a) a radical of formula $R_1R_2CHNH-Y-L^1-X^1-(CH_2)_z-$ wherein:

$R_1$ is a carboxylic acid group (—COOH), or an ester group which is hydrolysable by one or more intracellular esterase enzymes to a carboxylic acid group;

$R_2$ is the side chain of a natural or non-natural alpha amino acid;

Y is a bond, —C(=O)—, —S(=O)$_2$—, —C(=O)O—, —C(=O)NR$_3$—, —C(=S)—NR$_3$, —C(=NH)—NR$_3$ or —S(=O)$_2$NR$_3$— wherein R$_3$ is hydrogen or optionally substituted $C_1-C_6$ alkyl;

$L^1$ is a divalent radical of formula -(Alk$^1$)$_m$(Q)$_n$(Alk$^2$)$_p$- wherein m, n and p are independently 0 or 1, Q is (i) an optionally substituted divalent mono- or bicyclic carbocyclic or heterocyclic radical having 5-13 ring members, or (ii), in the case where p is 0, a divalent radical of formula -$Q^1$-$X^2$— wherein $X^2$ is —O—, —S— or $NR^A$— wherein $R^A$ is hydrogen or optionally substituted $C_1$-$C_3$ alkyl, and $Q^1$ is an optionally substituted divalent mono- or bicyclic carbocyclic or heterocyclic radical having 5-13 ring members, $Alk^1$ and $Alk^2$ independently represent optionally substituted divalent $C_3$-$C_7$ cycloalkyl radicals, or optionally substituted straight or branched, $C_1$-$C_6$ alkylene, $C_2$-$C_6$ alkenylene, or $C_2$-$C_6$ alkynylene radicals which may optionally contain or terminate in an ether (—O—), thioether (—S—) or amino (—$NR^A$—) link wherein $R^A$ is hydrogen or optionally substituted $C_1$-$C_3$ alkyl;

$X^1$ is a bond, —C(=O)—; or —S(=O)$_2$—; —$NR_4$C(=O)—, —C(=O)$NR_4$—, —$NR_4$C(=O)—$NR_5$—, —$NR_4$S(=O)$_2$—, or —S(=O)$_2NR_4$— wherein $R_4$ and $R_5$ are independently hydrogen or optionally substituted $C_1$-$C_6$ alkyl; and z is 0 or 1.

In another broad aspect, the invention provides the use of a compound of formula (IA) or (IB) as defined above, or an N-oxide, salt, hydrate or solvate thereof in the preparation of a composition for inhibiting the activity of IKK, especially IKKβ, as well as diseases modulated by the NF-kB cascade.

The compounds with which the invention is concerned may be used for the inhibition of IKK, especially IKKβ, activity in vitro or in vivo.

Pharmaceutical compositions comprising a compound of the invention together with one or more pharmaceutically acceptable carriers and excipients, also form part of the invention.

In one aspect of the invention, the compounds of the invention may be used in the preparation of a composition for the treatment of neoplastic/proliferative, autoimmune or inflammatory disease, particularly those mentioned above in which IKK, especially IKKp, activity plays a role.

In another aspect, the invention provides a method for the treatment of the foregoing disease types, which comprises administering to a subject suffering such disease an effective amount of a compound of formula (IA) or (IB) as defined above.

Terminology

As used herein, the term "($C_a$-$C_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent ($C_a$-$C_b$)alkylene radical" wherein a and b are integers refers to a saturated hydrocarbon chain having from a to b carbon atoms and two unsatisfied valences.

As used herein the term "($C_a$-$C_b$)alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent ($C_a$-$C_b$)alkenylene radical" means a hydrocarbon chain having from a to b carbon atoms, at least one double bond, and two unsatisfied valences.

As used herein the term "($C_a$-$C_b$)alkynyl" wherein a and b are integers refers to straight chain or branched chain hydrocarbon groups having from a to b carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent ($C_a$-$C_b$)alkynylene radical" wherein a and b are integers refers to a divalent hydrocarbon chain having from a to b carbon atoms, and at least one triple bond.

As used herein the term "carbocyclic" refers to a mono-, bi- or tricyclic radical having up to 16 ring atoms, all of which are carbon, and includes aryl and cycloalkyl.

As used herein the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and Q, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in its non-aromatic meaning relates to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

A "divalent phenylene, pyridinylene, pyrimidinylene, or pyrazinylene radical" is a benzene, pyridine, pyrimidine or pyrazine ring, with two unsatisfied valencies, and includes 1,3-phenylene, 1,4-phenylene, and the following:

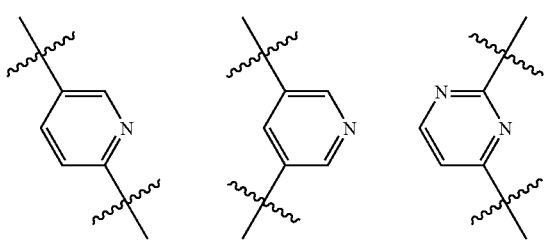

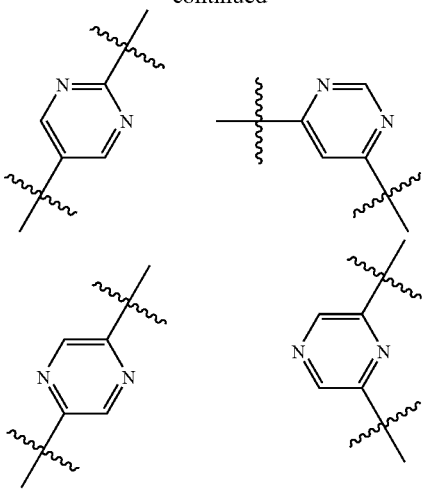

Unless otherwise specified in the context in which it occurs, the term "substituted" as applied to any moiety herein means substituted with up to four compatible substituents, each of which independently may be, for example, $(C_1-C_6)$alkyl, $(C_1-C_6)$alkoxy, hydroxy, hydroxy$(C_1-C_6)$alkyl, mercapto, mercapto$(C_1-C_6)$alkyl, $(C_1-C_6)$alkylthio, phenyl, halo (including fluoro, bromo and chloro), trifluoromethyl, trifluoromethoxy, nitro, nitrile (—CN), oxo, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OH, —NR$^B$SO$_2$OR$^A$, —NH-CONH$_2$, —NR$^A$CONH$_2$, —NHCONHR$^B$, —NR$^A$CONHR$^B$, —NHCONR$^A$R$^B$, or —NR$^A$CONR$^A$R$^B$ wherein R$^A$ and R$^B$ are independently a $(C_1-C_6)$alkyl, $(C_3-C_6)$cycloalkyl, phenyl or monocyclic heteroaryl having 5 or 6 ring atoms, or R$^A$ and R$^B$ when attached to the same nitrogen atom form a cyclic amino group (for example morpholino, piperidinyl, piperazinyl, or tetrahydropyrrolyl). An "optional substituent" may be one of the foregoing substituent groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (IA) and (IB) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like.

It is expected that compounds of the invention may be recovered in hydrate or solvate form. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds of the invention which contain one or more actual or potential chiral centres, because of the presence of asymmetric carbon atoms, can exist as a number of diastereoisomers with R or S stereochemistry at each chiral centre. The invention includes all such diastereoisomers and mixtures thereof.

The term "ester" or "ester group" or "esterified carboxyl group" in connection with substituent R$_1$ above means a group R$_x$O(C=O)— in which R$_x$ is the group characterising the ester, notionally derived from the alcohol R$_x$OH.

In the compounds of the invention, the variable substituents and groups will now be discussed in more detail:
The Substituent R$_7$
R$_7$ is hydrogen or optionally substituted $(C_1-C_6)$alkyl, such as methyl, ethyl or n- or iso-propyl. Currently preferred is when R$_7$ is hydrogen.
The Ring A
Ring A is an optionally substituted divalent aryl or heteroaryl ring of 5-13 atoms such as a monocyclic 5- or 6-membered ring or a bicyclic 5,6-, 6,6-, or 5,5-ring system. Examples include divalent phenylene, pyridinylene, pyrimidinylene, and pyrazinylene radicals. Currently preferred is 1,4-phenylene or 1,3-phenylene. Optional substituents in ring A may be selected from, for example fluoro, chloro, methyl, and trifluoromethyl.
The radical Z of formula —(CH$_2$)$_3$—X$^1$-L$^1$-Y—NHCHR$_1$R$_2$
The group R$_1$ in Z
R$_1$ is a carboxylic acid group or an ester group which is hydrolysable by one or more intracellular carboxylesterase enzymes to a carboxylic acid group. Intracellular carboxylesterase enzymes capable of hydrolysing the ester group of a compound of the invention to the corresponding acid include the three known human enzyme isotypes hCE-1, hCE-2 and hCE-3. Although these are considered to be the main enzymes, other enzymes such as biphenylhydrolase (BPH) may also have a role in hydrolysing the ester. In general, if the carboxylesterase hydrolyses the free amino acid ester to the parent acid it will also hydrolyse the ester motif when covalently conjugated to the IKK inhibitor. Hence, the broken cell assay described herein provides a straightforward, quick and simple first screen for esters which have the required hydrolysis profile. Ester motifs selected in that way may then be re-assayed in the same carboxylesterase assay when conjugated to the modulator via the chosen conjugation chemistry, to confirm that it is still a carboxylesterase substrate in that background.

Subject to the requirement that they be hydrolysable by intracellular carboxylesterase enzymes, examples of particular ester groups R$_1$ include those of formula —(C=O)OR$_{14}$ wherein R$_{14}$ is R$_8$R$_9$R$_{10}$C— wherein
(i) R$_8$ is hydrogen or optionally substituted $(C_1-C_3)$alkyl-$(Z^1)_a$—[$(C_1-C_3)$alkyl]$_b$- or $(C_2-C_3)$alkenyl-$(Z^1)_a$-[$(C_1-C_3)$alkyl]$_b$— wherein a and b are independently 0 or 1 and Z$^1$ is —O—, —S—, or wherein R$_{11}$ is hydrogen or $(C_1-C_3)$alkyl; and R$_9$ and R$_{10}$ are independently hydrogen or $(C_1-C_3)$alkyl-;
(ii) R$_8$ is hydrogen or optionally substituted R$_{12}$R$_{13}$N—$(C_1-C_3)$alkyl- wherein R$_{12}$ is hydrogen or $(C_1-C_3)$alkyl and R$_{13}$ is hydrogen or $(C_1-C_3)$alkyl; or R$_{12}$ and R$_{13}$ together with the nitrogen to which they are attached form an optionally substituted monocyclic heterocyclic ring of 5- or 6-ring atoms or bicyclic heterocyclic ring system of 8 to 10 ring atoms, and R$_9$ and R$_{10}$ are independently hydrogen or $(C_1-C_3)$alkyl-; or
(iii) R$_8$ and R$_9$ taken together with the carbon to which they are attached form an optionally substituted monocyclic carbocyclic ring of from 3 to 7 ring atoms or bicyclic carbocyclic ring system of 8 to 10 ring atoms, and $R_{10}$ is hydrogen.

Within these classes, $R_{10}$ is often hydrogen. Specific examples of $R_{14}$ include methyl, ethyl, n- or iso-propyl, n-, sec- or tert-butyl, cyclohexyl, allyl, phenyl, benzyl, 2-, 3- or 4-pyridylmethyl, N-methylpiperidin-4-yl, tetrahydrofuran-3-yl, methoxyethyl, indanyl, norbornyl, dimethylaminoethyl, or morpholinoethyl. Currently preferred is where $R_{14}$ is cyclopentyl or tert-butyl.

Macrophages are known to play a key role in inflammatory disorders through the release of cytokines in particular TNFα and IL-1 (van Roon et al., *Arthritis and Rheumatism*, 2003, 1229-1238). In rheumatoid arthritis they are major contributors to the maintenance of joint inflammation and joint destruction. Macrophages are also involved in tumour growth and development (Naldini and Carraro, *Curr Drug Targets Inflamm Allergy*, 2005, 3-8). Hence agents that selectively target macrophage cell proliferation and function could be of value in the treatment of cancer and autoimmune disease. Targeting specific cell types would be expected to lead to reduced side-effects. The inventors have discovered a method of targeting inhibitors to cells that express hCE-1, in particular, macrophages and other cells derived from the myelomonocytic lineage such as monocytes, osteoclasts and dendritic cells. This is based on the observation that the way in which the esterase motif is linked to the inhibitor determines whether it is hydrolysed by all three human carboxylesterases or just by hCE-1, and hence whether or not it accumulates in different cell types. Specifically it has been found that macrophages and other cells derived from the myelo-monocytic lineage, both normal and cancerous, contain the human carboxylesterase hCE-1 whereas other cell types do not. In the general formula (IA) and (IB) when the nitrogen of the esterase motif $R_1CH(R_2)NH$— is not directly linked to a carbonyl (—C(=O)—), i.e. when Y is not a —C(=O), —C(=O)O— or —C(=O)NR$_3$— radical, the ester will only be hydrolysed by hCE-1 and hence the inhibitors selectively accumulate in macrophage-related cells.

The Amino Acid Side Chain $R_2$ in Z

Subject to the requirement that the ester group $R_1$ be hydrolysable by intracellular carboxylesterase enzymes, the identity of the side chain group $R_2$ is not critical for non-macrophage selective compounds. For macrophage selective compounds, side chains such as valine, cyclohexylglycine, t-butylserine, t-butylcysteine, proline, phenylalanine, leucine and phenylglycine are preferred.

Examples of amino acid side chains include
($C_1$-$C_6$)alkyl, phenyl, 2-, 3-, or 4-hydroxyphenyl, 2-, 3-, or 4-methoxyphenyl, 2-, 3-, or 4-pyridylmethyl, benzyl, phenylethyl, 2-, 3-, or 4-hydroxybenzyl, 2-, 3-, or 4-benzyloxybenzyl, 2-, 3-, or 4-($C_1$-$C_6$)alkoxybenzyl, and benzyloxy($C_1$-$C_6$alkyl)- groups;
the characterising group of a natural α amino acid, in which any functional group may be protected;
groups -[Alk]$_n$R$_{16}$ where Alk is a ($C_1$-$C_6$)alkyl or ($C_2$-$C_6$) alkenyl group optionally interrupted by one or more —O—, or —S— atoms or —N(R$_{17}$)— groups [where R$_{17}$ is a hydrogen atom or a ($C_1$-$C_6$)alkyl group], n is 0 or 1, and R$_{16}$ is an optionally substituted cycloalkyl or cycloalkenyl group;
a benzyl group substituted in the phenyl ring by a group of formula —OCH$_2$COR$_{18}$ where R$_{18}$ is hydroxyl, amino, ($C_1$-$C_6$)alkoxy, phenyl($C_1$-$C_6$)alkoxy, ($C_1$-$C_6$)alkylamino, di(($C_1$-$C_6$)alkyl)amino, phenyl($C_1$-$C_6$)alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid;
a heterocyclic($C_1$-$C_6$)alkyl group, either being unsubstituted or mono- or di-substituted in the heterocyclic ring with halo, nitro, carboxy, ($C_1$-$C_6$)alkoxy, cyano, ($C_1$-$C_6$)alkanoyl, trifluoromethyl ($C_1$-$C_6$)alkyl, hydroxy, formyl, amino, ($C_1$-$C_6$) alkylamino, di-($C_1$-$C_6$)alkylamino, mercapto, ($C_1$-$C_6$)alkylthio, hydroxy($C_1$-$C_6$)alkyl, mercapto($C_1$-$C_6$)alkyl or ($C_1$-$C_6$)alkylphenylmethyl; and
a group —CR$_a$R$_b$R$_c$ in which:
each of $R_a$, $R_b$ and $R_c$ is independently hydrogen, ($C_1$-$C_6$) alkyl, ($C_2$-$C_6$)alkenyl, ($C_2$-$C_6$)alkynyl, phenyl($C_1$-$C_6$) alkyl, ($C_3$-$C_8$)cycloalkyl; or
$R_c$ is hydrogen and $R_a$ and $R_b$ are independently phenyl or heteroaryl such as pyridyl; or
$R_c$ is hydrogen, ($C_1$-$C_6$)alkyl, ($C_2$-$C_6$)alkenyl, ($C_2$-$C_6$) alkynyl, phenyl($C_1$-$C_6$)alkyl, or ($C_3$-$C_8$)cycloalkyl, and $R_a$ and $R_b$ together with the carbon atom to which they are attached form a 3 to 8 membered cycloalkyl or a 5- to 6-membered heterocyclic ring; or
$R_a$, $R_b$ and $R_c$ together with the carbon atom to which they are attached form a tricyclic ring (for example adamantyl); or
$R_a$ and $R_b$ are each independently ($C_1$-$C_6$)alkyl, ($C_2$-$C_6$) alkenyl, ($C_2$-$C_6$)alkynyl, phenyl($C_1$-$C_6$)alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —CO$_2$H, ($C_1$-$C_4$)perfluoroalkyl, —CH$_2$OH, —SO$_2$($C_1$-$C_6$)alkyl, —O($C_1$-$C_6$)alkyl, —O($C_2$-$C_6$)alkenyl, —S($C_1$-$C_6$) alkyl, —SO($C_1$-$C_6$)alkyl, —SO$_2$($C_1$-$C_6$)alkyl, —S($C_2$-$C_6$)alkenyl, —SO($C_2$-$C_6$)alkenyl, —SO$_2$($C_2$-$C_6$)alkenyl or a group -Q-W wherein Q represents a bond or —O—, —S—, —SO— or —SO$_2$— and W represents a phenyl, phenylalkyl, ($C_3$-$C_8$)cycloalkyl, ($C_3$-$C_8$)cycloalkylalkyl, ($C_4$-$C_8$)cycloalkenyl, ($C_4$-$C_8$)cycloalkenylalkyl, heteroaryl or heteroarylalkyl group, which group W may optionally be substituted by one or more substituents independently selected from, hydroxyl, halogen, —CN, —CO$_2$H, —SO$_2$($C_1$-$C_6$)alkyl, —CONH$_2$, —CONH($C_1$-$C_6$)alkyl, —CONH($C_1$-$C_6$) alkyl)$_2$, —CHO, —CH$_2$OH, ($C_1$-$C_4$)perfluoroalkyl, —O($C_1$-$C_6$)alkyl, —S($C_1$-$C_6$)alkyl, —SO($C_1$-$C_6$)alkyl, —SO$_2$($C_1$-$C_6$)alkyl, —NO$_2$, —NH$_2$, —NH($C_1$-$C_6$) alkyl, —N(($C_1$-$C_6$)alkyl)$_2$, —NHCO($C_1$-$C_6$)alkyl, ($C_1$-$C_6$)alkyl, (O$_2$—$C_6$)alkenyl, (O$_2$—$C_6$)alkynyl, ($C_3$-$C_8$) cycloalkyl, ($C_4$-$C_8$)cycloalkenyl, phenyl or benzyl.

Examples of particular $R_2$ groups include hydrogen (the glycine "side chain"), benzyl, phenyl, cyclohexylmethyl, cyclohexyl, pyridin-3-ylmethyl, tert-butoxymethyl, iso-butyl, sec-butyl, tert-butyl, 1-benzylthio-1-methylethyl, 1-methylthio-1-methylethyl, 1-mercapto-1-methylethyl, and phenylethyl. Presently preferred $R_2$ groups include phenyl, benzyl, iso-butyl, cyclohexyl and t-butoxymethyl.

For compounds of the invention which are to be administered systemically, esters with a slow rate of carboxylesterase cleavage are preferred, since they are less susceptible to pre-systemic metabolism. Their ability to reach their target tissue intact is therefore increased, and the ester can be converted inside the cells of the target tissue into the acid product. However, for local administration, where the ester is either directly applied to the target tissue or directed there by, for example, inhalation, it will often be desirable that the ester has a rapid rate of esterase cleavage, to minimise systemic exposure and consequent unwanted side effects. In the compounds of this invention, if the carbon adjacent to the alpha carbon of the alpha amino acid ester is mono-substituted, i.e. $R_2$ is —$CH_2R^z$ ($R^z$ being the mono-substituent) then the esters tend to be cleaved more rapidly than if that carbon is di- or tri-substituted, as in the case where $R_2$ is, for example, phenyl or cyclohexyl.

The Radical —$(CH_2)_z$—$X^1$-$L^1$-$Y$— in Z

This radical (or bond) arises from the particular chemistry strategy chosen to link the amino acid ester motif $R_1CH(R_2)$ NH— to the rest of the molecule. Clearly the chemistry strategy for that coupling may vary widely, and thus many combinations of the variables z, $L^1$, $X^1$ and Y are possible. The precise combination of variables making up the linking chemistry between the amino acid ester motif and the rest of the molecule will often be irrelevant to the primary binding mode of the compound as a whole. On the other hand, that linkage chemistry may in some cases pick up additional binding interactions with the enzyme, thereby enhancing binding.

It should also be noted that the benefits of the amino acid ester motif described above (facile entry into the cell, carboxylesterase hydrolysis within the cell, and accumulation within the cell of active carboxylic acid hydrolysis product) are best achieved when the linkage between the amino acid ester motif and the rest of the molecule is not a substrate for peptidase activity within the cell, which might result in cleavage of the amino acid from the molecule. Of course, stability to intracellular peptidases is easily tested by incubating the compound with disrupted cell contents, and analysing for any such cleavage.

With the foregoing general observations in mind, taking the variables making up the radical —$(CH_2)_z$—$X^1$-$L^1$-$Y$— in turn:

z may be 0 or 1;

In the radical $L^1$, examples of $Alk^1$ and $Alk^2$ radicals, when present, include —$CH_2$—, —$CH_2CH_2$—, —$CH_2CH_2CH_2$—, —$CH_2CH_2CH_2CH_2$—, —$CH=CH$—, —$CH=CHCH_2$—, —$CH_2CH=CH$—, $CH_2CH=CHCH_2$—$C\equiv C$—, —$C\equiv CCH_2$—, $CH_2C\equiv C$—, and $CH_2C\equiv CCH_2$. Additional examples of $Alk^1$ and $Alk^2$ include —$CH_2W$—, —$CH_2CH_2W$—, —$CH_2CH_2WCH_2$—, —$CH_2CH_2WCH(CH_3)$—, —$CH_2WCH_2CH_2$—, —$CH_2WCH_2CH_2WCH_2$—, and —$WCH_2CH_2$— where W is —O—, —S—, —NH—, —$N(CH_3)$—, or —$CH_2CH_2N(CH_2CH_2OH)CH_2$—. Further examples of $Alk^1$ and $Alk^2$ include divalent cyclopropyl, cyclopentyl and cyclohexyl radicals.

$Alk^1$ and $Alk^2$ when present may also be branched chain alkyl such as —$CH(CH_3)$—, —$C(CH_3)_2$—, or in either orientation —$CH_2CH(CH_3)$—, —$CH_2C(CH_3)_2$—.

In $L^1$, when n is 0, and at least one of m and p is 1, the radical is a hydrocarbon chain (optionally substituted and perhaps having an ether, thioether or amino linkage). Presently it is preferred that there be no optional substituents in $L^1$. When both m and p are 0, $L^1$ is a divalent mono- or bicyclic carbocyclic or heterocyclic radical with 5-13 ring atoms (optionally substituted, but presently preferred to be unsubstituted, and perhaps linked to an adjacent atom through an ether, thioether or amino link (Note: this is when Q is -$Q^2$-$X^2$—, if applicable in this application). When n is 1 and at least one of m and p is 1, $L^1$ is a divalent radical including a hydrocarbon chain or chains (optionally substituted and perhaps having an ether, thioether or amino linkage) and a mono- or bicyclic carbocyclic or heterocyclic radical with 5-13 ring atoms (optionally substituted, but presently preferred to be unsubstituted, and perhaps linked to an adjacent atom through an ether, thioether or amino link.

When present, Q may be, for example, a divalent phenyl, naphthyl, cyclopropyl, cyclopentyl, or cyclohexyl radical, or a mono-, or bi-cyclic heterocyclic radical having 5 to 13 ring members, such as piperidinyl, piperazinyl, indolyl, pyridyl, thienyl, or pyrrolyl radical.

In some embodiments of the invention, $L^1$, m and p may be 0 with n being 1. In other embodiments, n and p may be 0 with m being 1. In further embodiments, m, n and p may be all 0. In still further embodiments m may be 0, n may be 1 with Q being a monocyclic heterocyclic radical, and p may be 0 or 1. Specifically, $Alk^1$ and $Alk^2$, when present, may be selected from —$CH_2$—, —$CH_2CH_2$—, and —$CH_2CH_2CH_2$— and Q when present may be selected from:

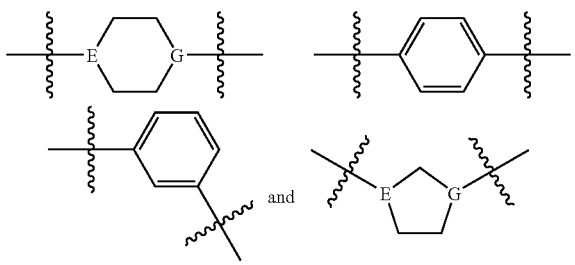

wherein E and G are independently CH or N.

The linkage $X^1$ represents a bond, —$(C=O)$—, —$S(O_2)$—, —$NR_4C(=O)$—, —$C(=O)NR_4$—, —$NR_4C(=O)$—$NR_5$—, —$NR_4S(=O)_2$—, or —$S(=O)_2NR_4$— wherein $R_4$ and $R_5$ are independently hydrogen or optionally substituted $C_1$-$C_6$ alkyl such as methyl or ethyl.

The linkage Y is a bond, —$C(=O)$—, —$S(=O)_2$—, —$C(=O)O$—, —$C(=O)NR_3$—, —$C(=S)$—$NR_3$, —$C(=NH)$—$NR_3$ or —$S(=O)_2NR_3$— wherein $R_3$ is hydrogen or optionally substituted $C_1$-$C_6$ alkyl such as methyl or ethyl.

Often z will be 0 and $X^1$ and Y will each simply be a bond, so that the amino acid esterase motif $R_1R_2CHNH$— is linked to the ring containing X by the radical $L^1$ as defined and discussed above.

In particular examples compounds of the invention, the radical $R_1R_2CHNH$—Y-$L^1X^1$—$(CH_2)_z$— is selected from $R_1R_2CHNH$—$(CH_2)_a$—, $R_1R_2CHNH$—$(CH_2)_a$O—, and $R_1R_2CHNH$—$CH_2CH=CHCH_2$—, wherein a is 1, 2, 3, 4 or 5.

In other compounds of the invention $R_1R_2CHNH$—Y-$L^1X^1$—$(CH_2)_z$—, is selected from: $R_1R_2CHNHSO_2$—, $R_1R_2CHNHCO$—,

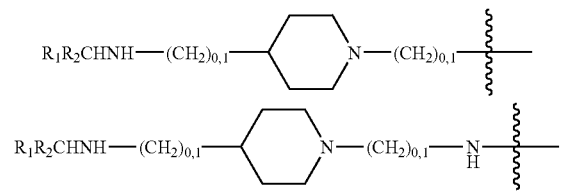

-continued

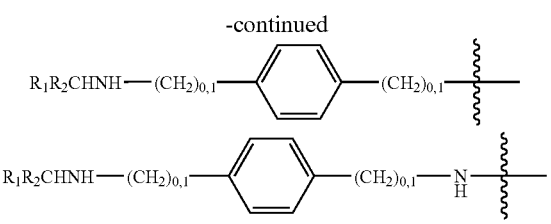

Specific compounds of the invention include those of the examples herein, their salts, N-oxides, hydrates and solvates.

As mentioned above, the compounds with which the invention is concerned are inhibitors of IKK, especially IKKβ kinase activity, and are therefore of use in the treatment of diseases modulated by IKK activity and the NF-kB cascade. Such diseases include neoplastic/proliferative, immune and inflammatory disease. In particular, uses of the compounds include treatment of cancers such as hepatocellular cancer or melanoma, but also including bowel cancer, ovarian cancer, head and neck and cervical squamous cancers, gastric or lung cancers, anaplastic oligodendrogliomas, glioblastoma multiforme or medulloblastomas; and treatment of rheumatoid arthritis, psoriasis, inflammatory bowel disease, Crohn's disease, ulcerative colitis, chronic obstructive pulmonary disease, asthma, multiple sclerosis, diabetes, atopic dermatitis, graft versus host disease, or systemic lupus erythematosus.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The compounds of the invention may be administered in inhaled form. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active compounds may be dosed as described depending on the inhaler system used. In addition to the active compounds, the administration forms may additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321).

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The compounds of the invention may be used in conjunction with a number of known pharmaceutically active substances. For example, the compounds of the invention may be used with cytotoxics, HDAC inhibitors, kinase inhibitors, aminopeptidase inhibitors, protease inhibitors, bcl-2 antagonists, inhibitors of mTor and monoclonal antibodies (for example those directed at growth factor receptors). Preferred cytotoxics include, for example, taxanes, platins, anti-metabolites such as 5-fluoracil, topoisomerase inhibitors and the like. The medicaments of the invention comprising amino acid derivatives of formula (IA) or (IB), tautomers thereof or pharmaceutically acceptable salts, N-oxides, hydrates or solvates thereof therefore typically further comprise a cytotoxic, an HDAC inhibitor, a kinase inhibitor, an aminopeptidase inhibitor and/or a monoclonal antibody.

Further, the present invention provides a pharmaceutical composition comprising:
  (a) an amino acid derivative of formula (IA) or (IB), or a pharmaceutically acceptable salt, N-oxide, hydrate or solvate thereof;
  (b) a cytotoxic agent, an HDAC inhibitor, a kinase inhibitor, an aminopeptidase inhibitor, a protease inhibitor, a bcl-2 antagonist, an inhibitor of mTor and/or a monoclonal antibody; and
  (c) a pharmaceutically acceptable carrier or diluent.

Also provided is a product comprising:
  (a) an amino acid derivative of formula (IA) or (IB), or a pharmaceutically acceptable salt, N-oxide, hydrate or solvate thereof; and (b) a cytotoxic agent, an HDAC inhibitor, a kinase inhibitor, an aminopeptidase inhibitor, a protease inhibitor, a bcl-2 antagonist, an inhibitor of mTor and/or a monoclonal antibody, for the separate, simultaneous or sequential use in the treatment of the human or animal body.

Synthesis

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to those skilled in the art. Typical literature sources are "Advanced organic chemistry", 4$^{th}$ Edition (Wiley), J March, "Comprehensive Organic Transformation", 2$^{nd}$ Edition (Wiley), R. C. Larock, "Handbook of Heterocyclic Chemistry", 2$^{nd}$ Edition (Pergamon), A. R. Katritzky), review, articles such as found in "Synthesis", "Acc. Chem. Res.", "Chem. Rev", or primary literature sources identified by standard literature searches online or from secondary sources such as "Chemical Abstracts" or "Beilstein".

The compounds of the invention may be prepared by a number of processes generally described below and more specifically in the Examples hereinafter. In the reactions described below, it may be necessary to protect reactive functional groups, for example hydroxyl, amino and carboxy groups, where these are desired in the final product, to avoid their unwanted participation in the reactions [see for example Greene, T. W., "Protecting Groups in Organic Synthesis", John Wiley and Sons, 1999]. Conventional protecting groups may be used in conjunction with standard practice. In some instances deprotection may be the final step in the synthesis of a compound of general formula (IA) or (IB), and the processes according to the invention described herein after are understood to extend to such removal of protecting groups.

As mentioned above, the compounds with which the invention is concerned are inhibitors of the IkB family, namely IKK-α and IKK-β, and are therefore of use in the treatment of cell proliferative disease, such as cancer, and in treatment of inflammation, in humans and other mammals.

ABBREVIATIONS

| | |
|---|---|
| MeOH = | methanol |
| EtOH = | ethanol |
| EtOAc = | ethyl acetate |
| DCM = | dichloromethane |
| DIBAL = | Di-isobutylaluminium hydride |
| DMF = | dimethylformamide |
| DME = | dimethyl etherLV |
| DMSO = | dimethyl sulfoxide |
| DMAP = | dimethylamino pyridine |
| TFA = | trifluoroacetic acid |
| THF = | tetrahydrofuran |
| Na$_2$CO$_3$ = | sodium carbonate |
| HCl = | hydrochloric acid |
| DIPEA = | diisopropylethylamine |
| LiHMDS = | lithium bis(trimethylsilyl)amide |
| MP-CNBH$_3$ = | macroporous triethylammonium methylpolystyrene cyanoborohydride |
| NaH = | sodium hydride |
| NaOH = | sodium hydroxide |
| NaHCO$_3$ = | sodium hydrogen carbonate |
| HCl = | hydrochloric acid |
| Pd/C = | palladium on carbon |

-continued

| | |
|---|---|
| PdCl$_2$(dppf) = | [1,1'-Bis(diphenylphosphino)ferrocene] dichloropalladium(II). |
| EDC = | 1-ethyl-3-(3-dimethylaminopropyl)carbodiimide |
| KOAc = | potassium acetate |
| TBAI = | tetrabutyl ammonium iodide |
| ml = | millilitre(s) |
| g = | gram(s) |
| mg = | milligram(s) |
| mol = | mole(s) |
| mmol = | millimole(s) |
| Sat = | saturated |
| LCMS = | high performance liquid chromatography/mass spectrometry |
| NMR = | nuclear magnetic resonance |

Commercially available reagents and solvents (HPLC grade) were used without further purification. Solvents were removed using a Buchi rotary evaporator. Microwave irradiation was carried out using a CEM Discovery model set at 300 W. Purification of compounds by flash chromatography column was performed using silica gel, particle size 40-63μ μm (230-400 mesh) obtained from Fluorochem. Purification of compounds by preparative HPLC was performed on a Agilent prep system using reverse phase Agilent prep-C18 columns (5 μm, 50×21.2 mm), gradient 0-100% B (A=water/0.1% ammonia or 0.1% formic acid and B=acetonitrile/0.1% ammonia or 0.1% formic acid) over 10 min, flow=28 ml/min, UV detection at 254 nm.

$^1$H NMR spectra were recorded on a Bruker 400 or 300 MHz AV spectrometer in deuterated solvents. Chemical shifts (δ) are in parts per million. Thin-layer chromatography (TLC) analysis was performed with Kieselgel 60 F$_{254}$ (Merck) plates and visualized using UV light.

Analytical HPLC/MS were obtained as follows: Agilent Prep-C18 Scalar column, 5 μm (4.6×50 mm, flow rate 2.5 ml/min) eluting with a H$_2$O-MeCN gradient containing 0.1% v/v formic acid over 7 minutes with UV detection at 254 nm. Gradient information: 0.0-0.5 min: 95% H$_2$O-5% MeCN; 0.5-5.0 min; Ramp from 95% H$_2$O-5% MeCN to 5% H$_2$O-95% MeCN; 5.0-5.5 min: Hold at 5% H$_2$O-95% MeCN; 5.5-5.6 min: Hold at 5% H$_2$O-95% MeCN, flow rate increased to 3.5 ml/min; 5.6-6.6 min: Hold at 5% H$_2$O-95% MeCN, flow rate 3.5 ml/min; 6.6-6.75 min: Return to 95% H$_2$O-5% MeCN, flow rate 3.5 ml/min; 6.75-6.9 min: Hold at 95% H$_2$O-5% MeCN, flow rate 3.5 ml/min; 6.9-7.0 min: Hold at 95% H$_2$O-5% MeCN, flow rate reduced to 2.5 ml/min. Mass spectra were obtained using an Agilent multimode source in either the positive (APCI+ESI$^+$) or negative (APCI+ESI$^-$) mode.

Examples of such methods that may be employed to the synthesis of compounds of general formula (IA) and (IB) are set out, but not limited to the reactions shown in Schemes 1-9 below.

Scheme 1 illustrates the general synthetic route for the preparation of the examples described below, using traditional Suzuki chemistry to couple the relevant boronate ester (or acid) intermediates (4-11) with the central thiophene core (Intermediate 1).

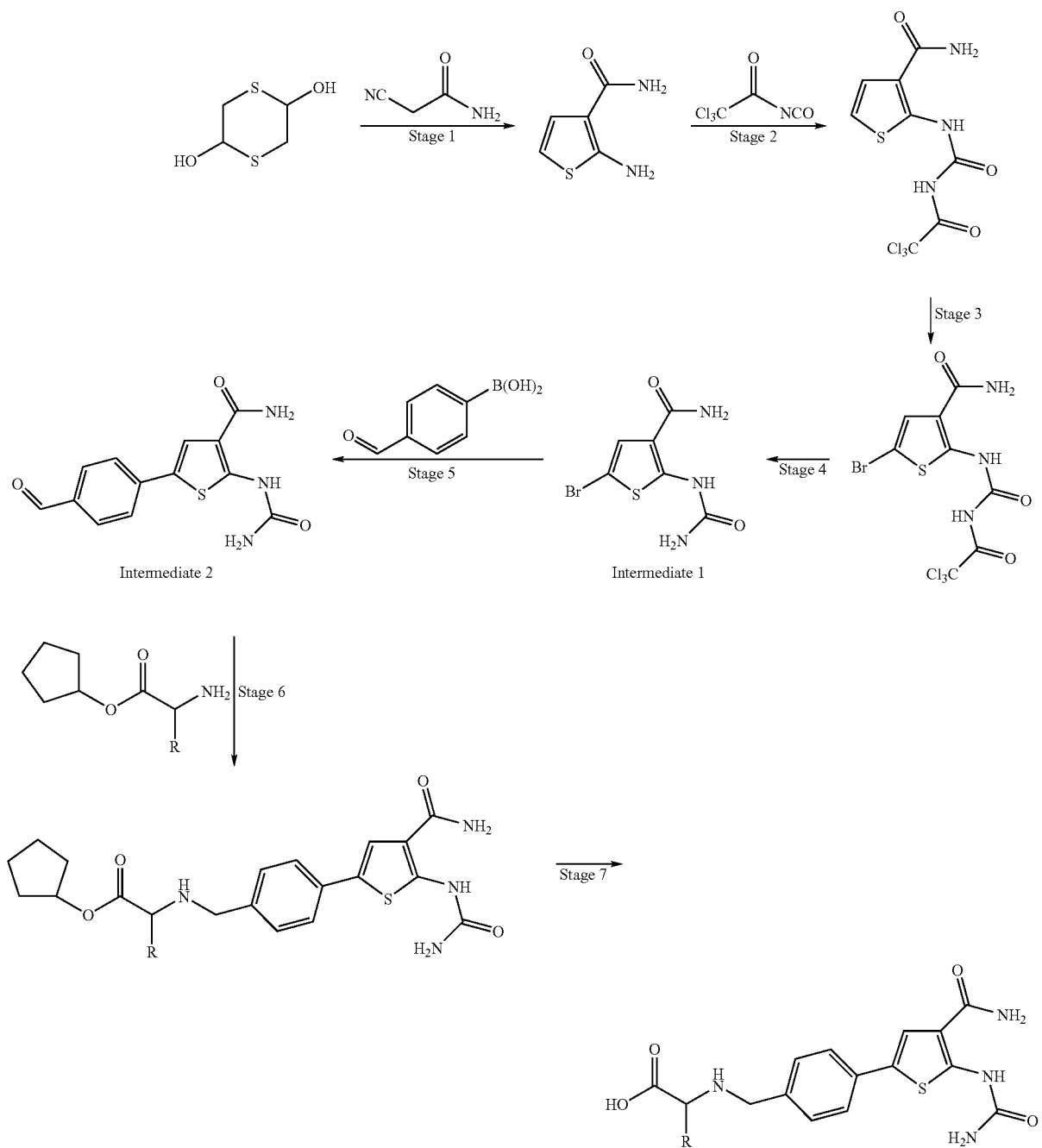
Scheme 1
Scheme 2 illustrates an alternative synthesis to these phenyl substituted thiophene analogues.
Scheme 2
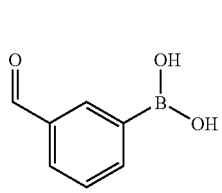
+
-continued
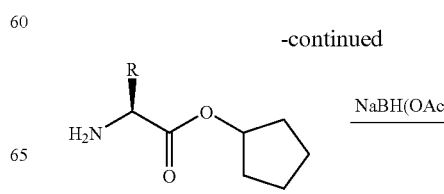

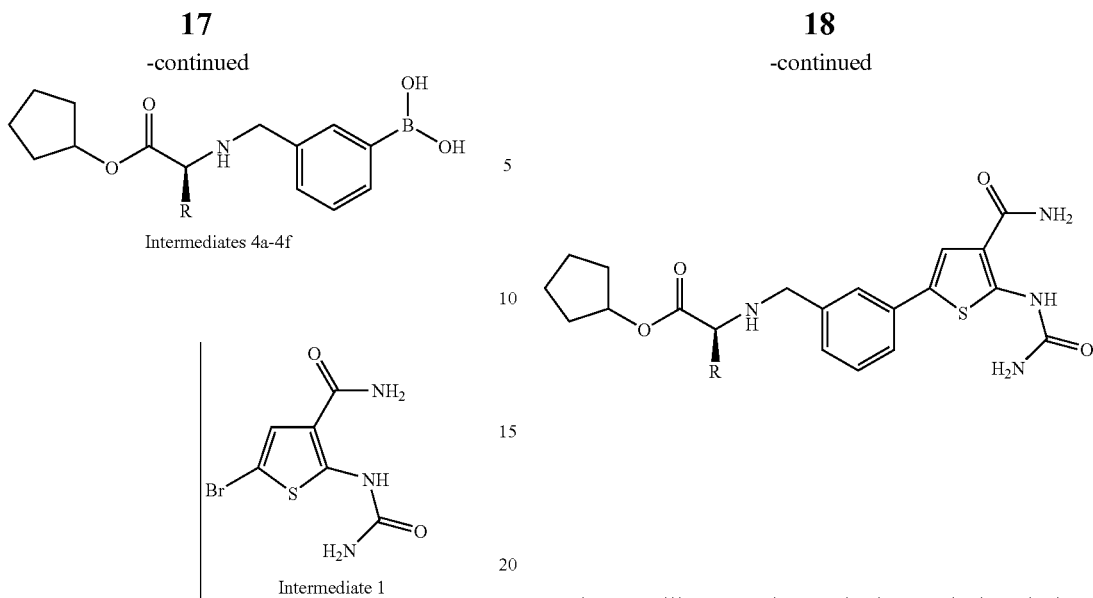
Scheme 3 illustrates the synthesis to substituted phenyl linker thiophene analogues.
Scheme 3
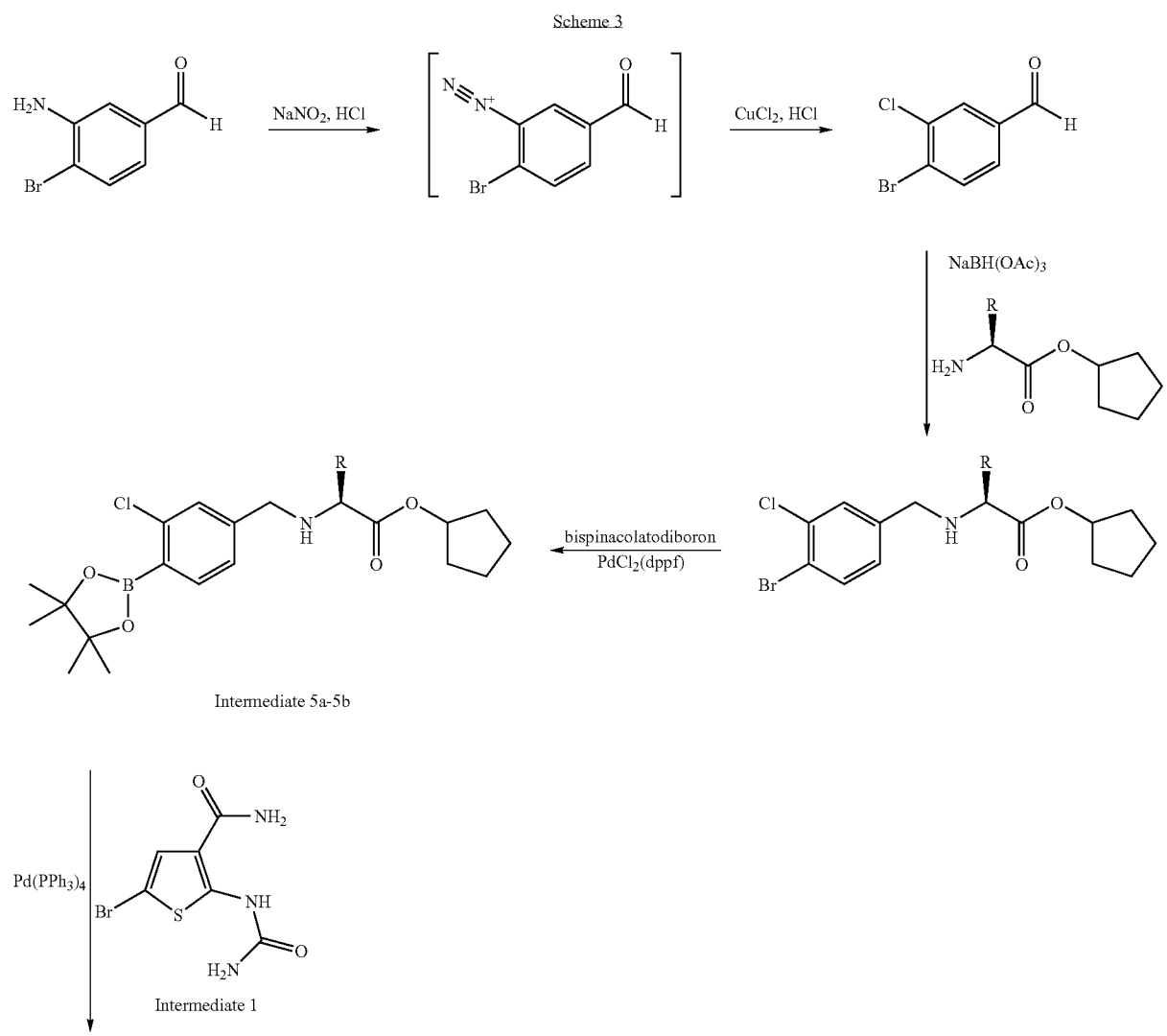

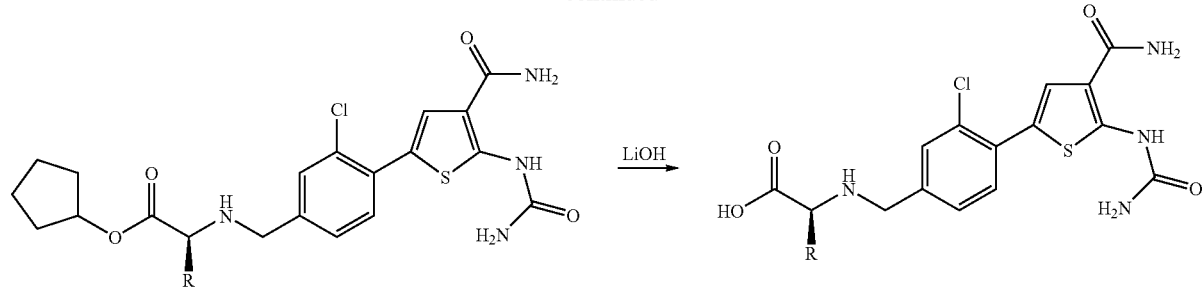
Scheme 4 illustrates the synthesis to extended linker $^{15}$ thiophene analogues.
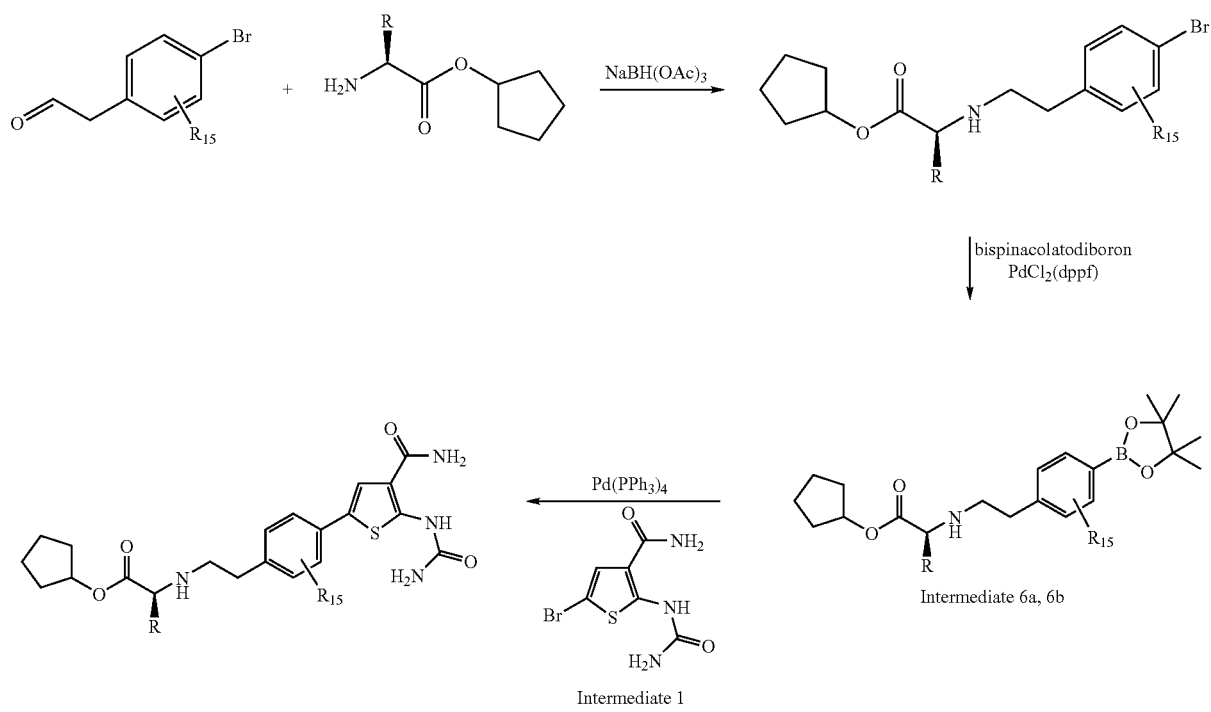
Schemes 5 and 6 illustrate the synthesis to extended oxygen linked thiophene analogues.
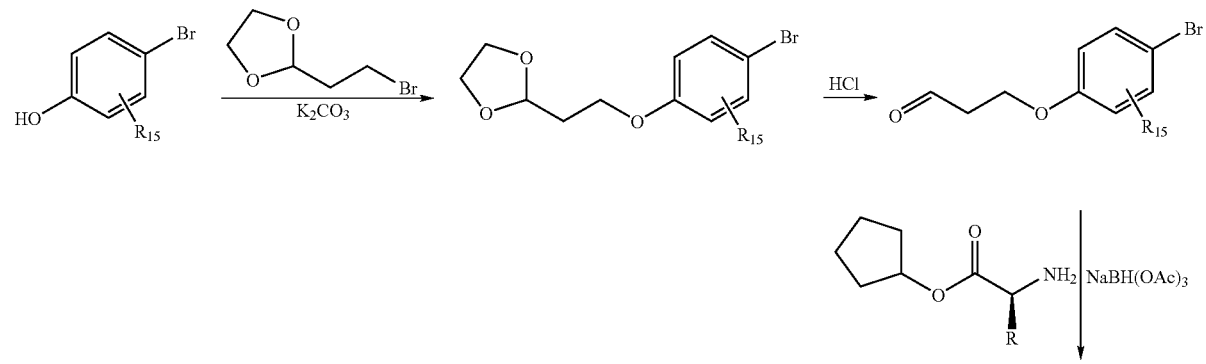

-continued
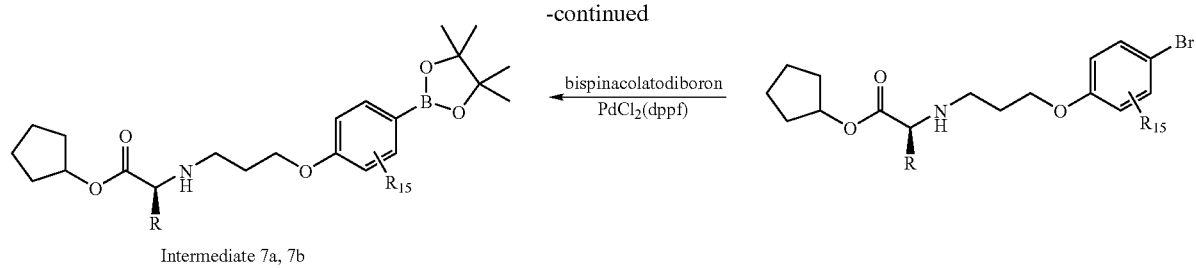
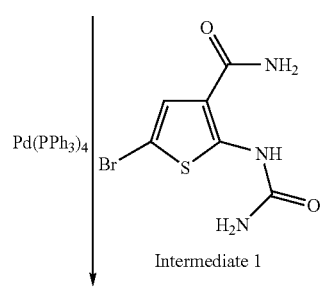
Intermediate 1
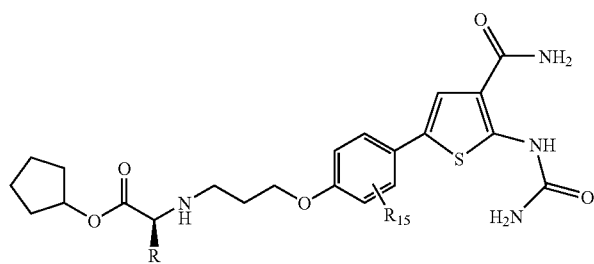
Scheme 6
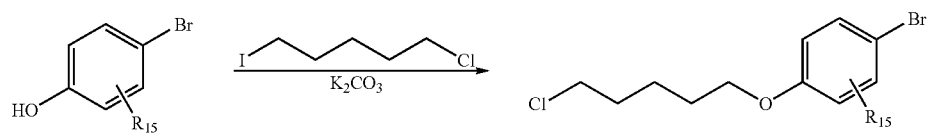
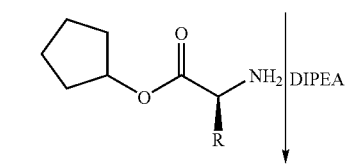

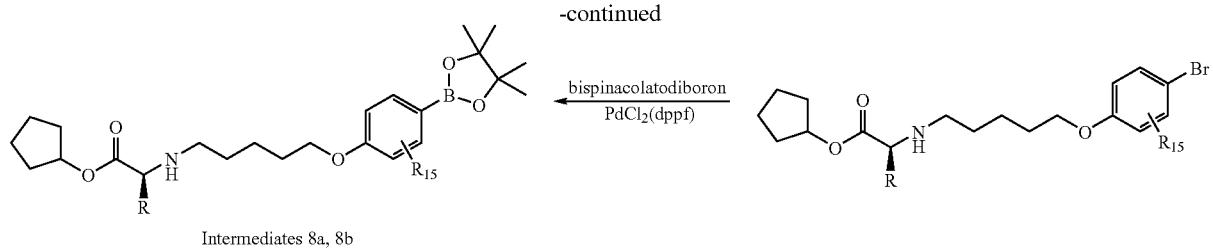
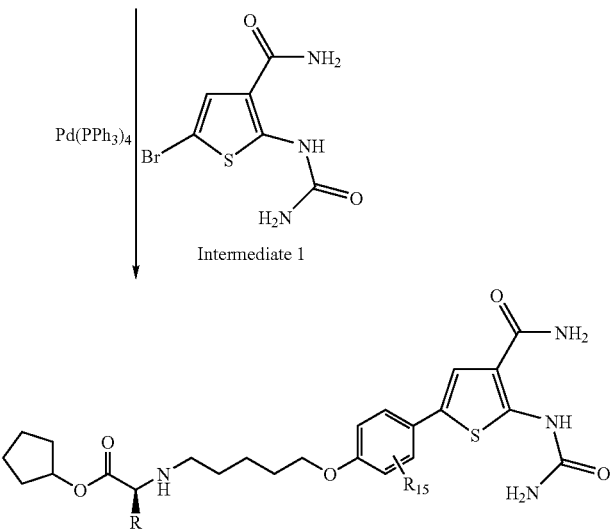
Scheme 7 illustrates the synthesis of alternative alkene linker thiophene analogues
Scheme 7
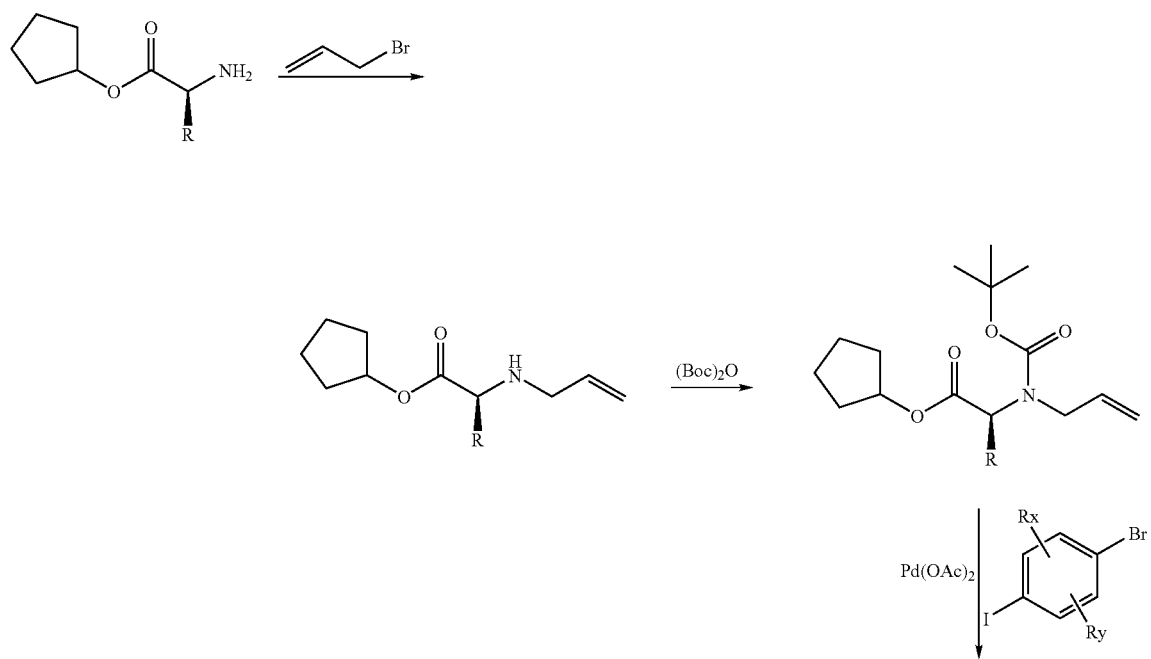

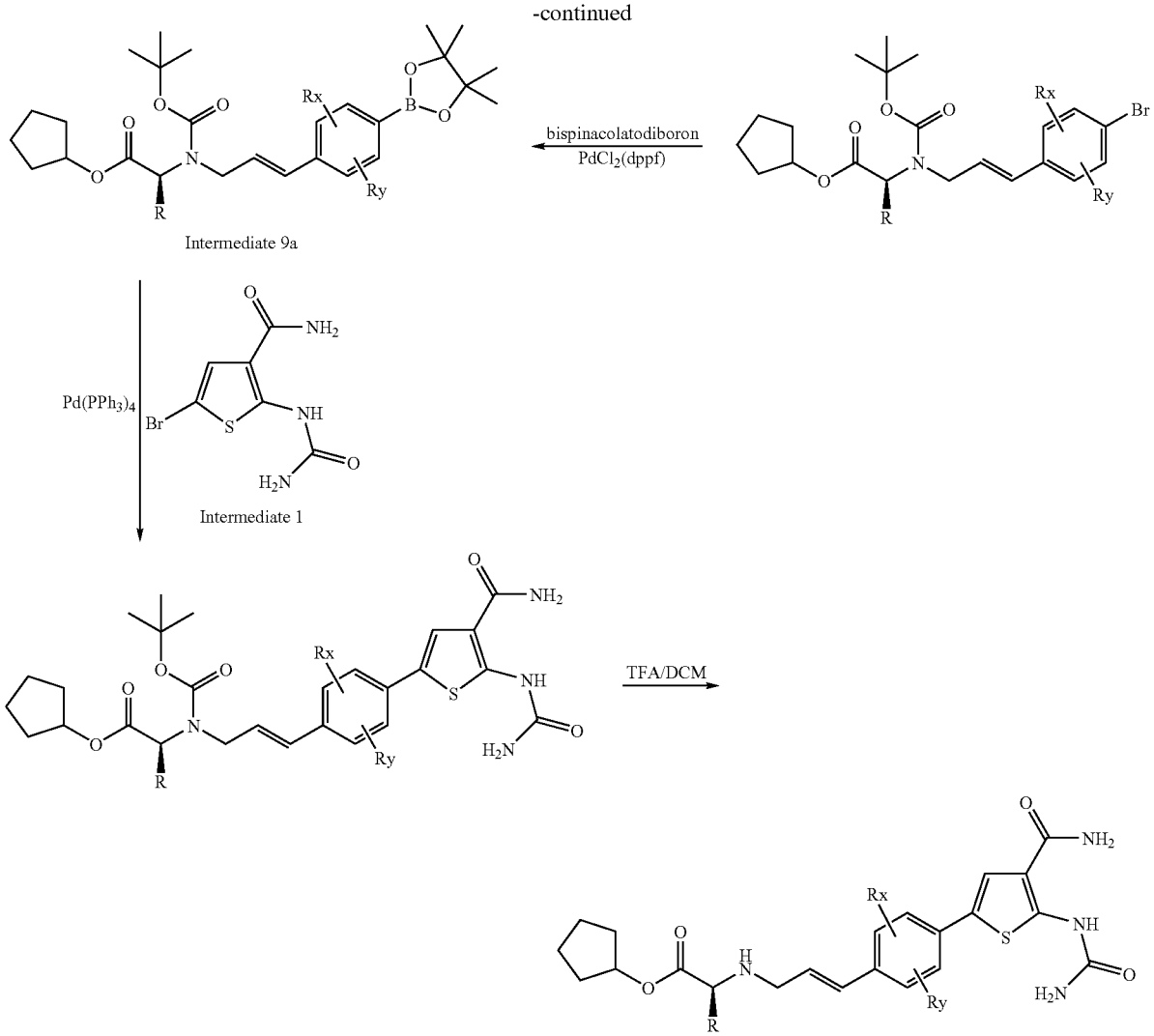
Scheme 8 illustrates an alternative synthesis to the alkene linker thiophene analogues.
Scheme 8
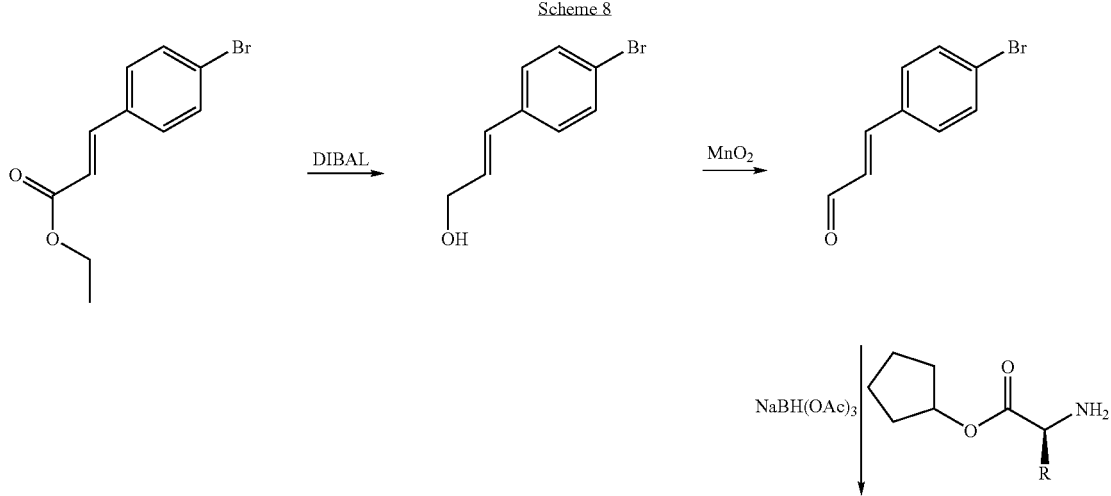

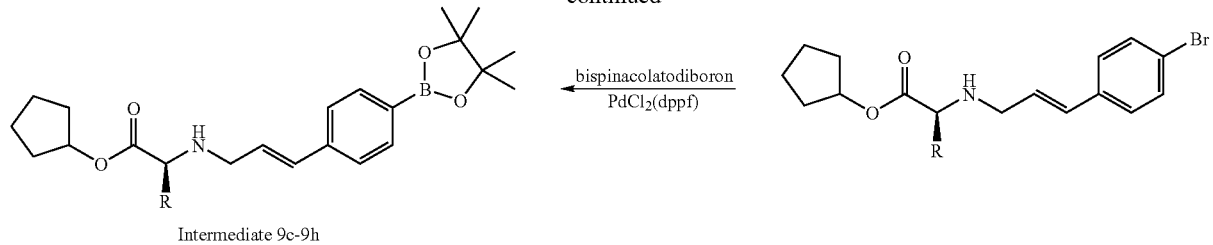
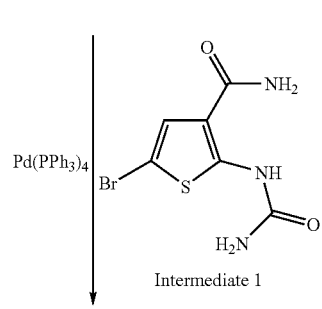
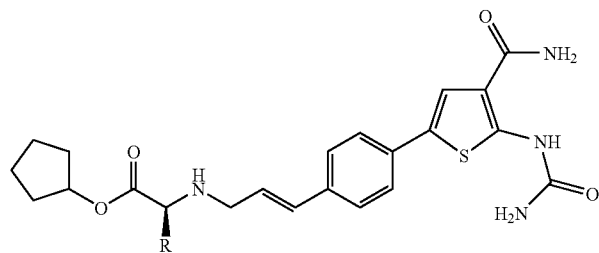
Scheme 9 illustrates the synthesis of phenyl substituted extended linker thiophene analogues.
Scheme 9
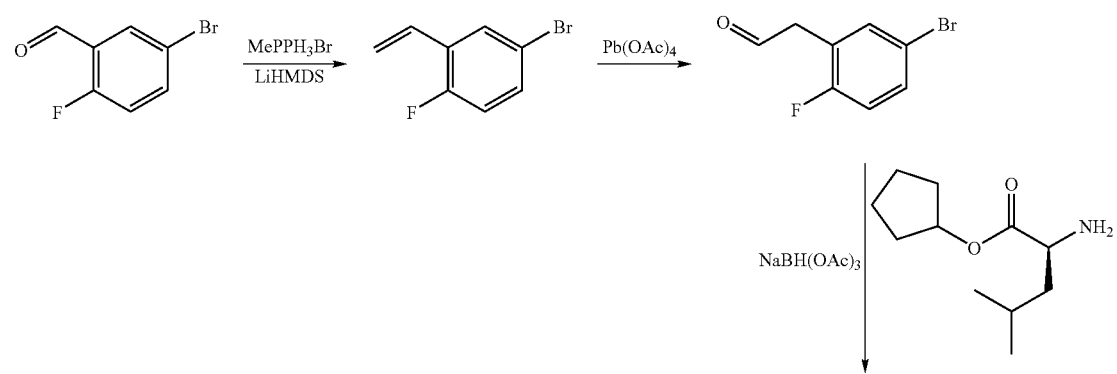

-continued

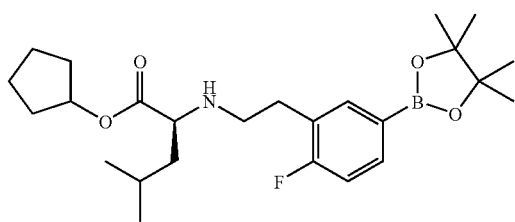

Intermediate 11a

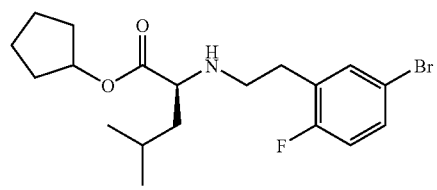

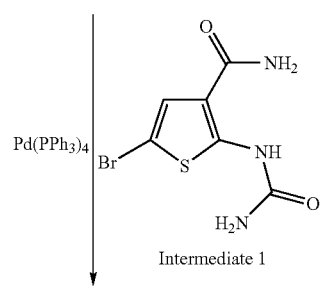

Intermediate 1

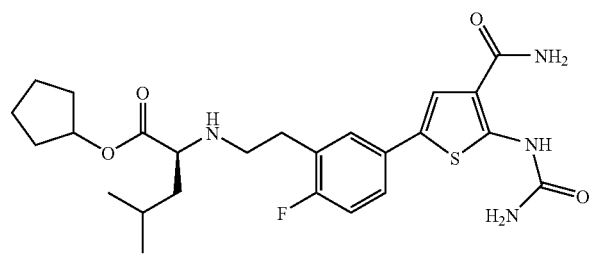

Example 22

INTERMEDIATES

Intermediate 1
5-Bromo-2-(carbamoylamino)thiophene-3-carboxamide

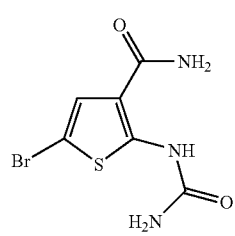

The synthesis of Intermediate 1 highlighted by Stages 1-4 in Scheme 1 is detailed within WO03104218.

Intermediate 2 2-(Carbamoylamino)-5-(4-formylphenyl)thiophene-3-carboxamide

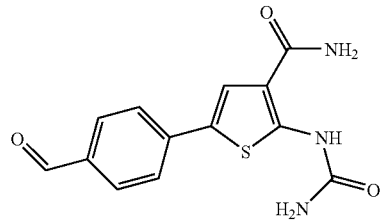

To a mixture of 5-bromo-2-(carbamoylamino)thiophene-3-carboxamide (1.0 g, 3.79 mmol), 4-formylphenylboronic acid (0.625 g, 4.17 mmol) and tetrakis(triphenylphosphine) Pd catalyst (0.438 g, 0.379 mmol) in DME (50 ml) was added a saturated aqueous solution of sodium hydrogen carbonate (10 ml). The reaction vessel was flushed with nitrogen and heated to 90° C. overnight. LCMS indicated complete consumption of the starting material. The reaction mixture was concentrated using a rotary evaporator. The resultant dark brown residue was dissolved in DCM (17 ml) and stirred with aqueous 2M sodium hydroxide solution (8.5 ml) for 20 minutes. Diethyl ether (20 ml) was added and the mixture stirred for a further 30 minutes. The resultant suspension was sonicated for 2 minutes. Filtration gave a precipitate, which was washed with hot diethyl ether to give a coloured solid (440 mg).

LCMS: m/z 288 [M−H]$^+$; m/z 290 [M+H]$^+$.

Intermediates 3a-3i Preparation of Amino Acid Esters

Route I.

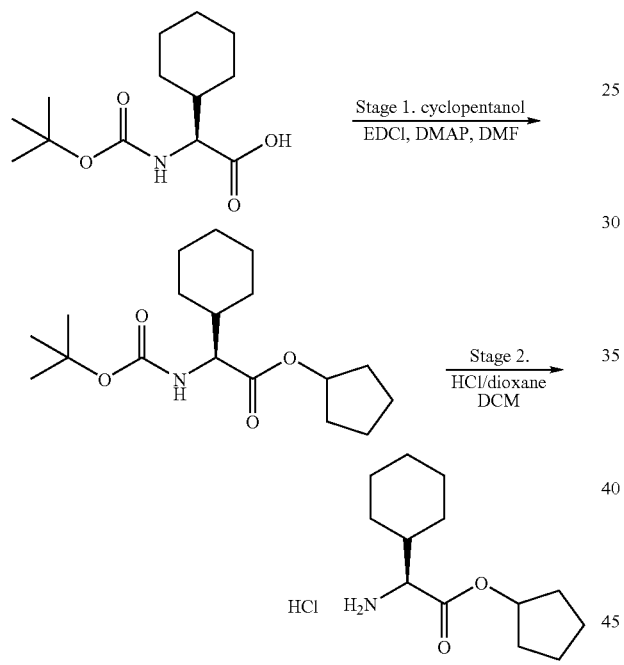

Route II.

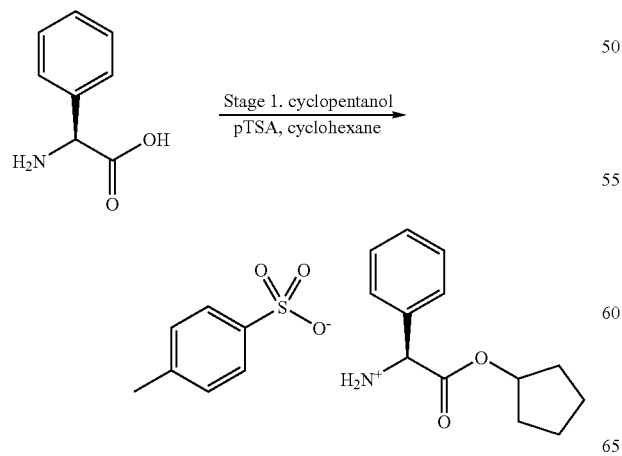

Intermediates Prepared:

List 1

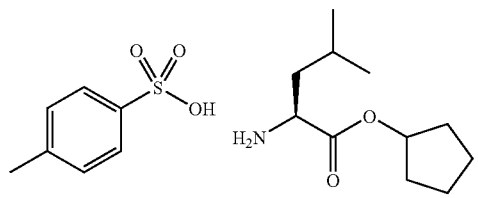

Intermediate 3a

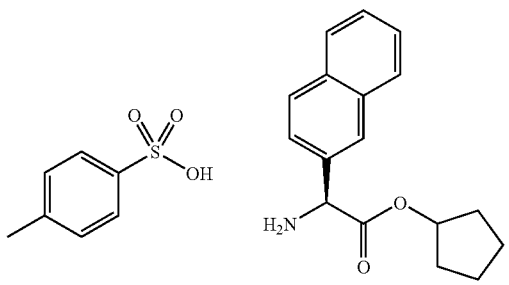

Intermediate 3b

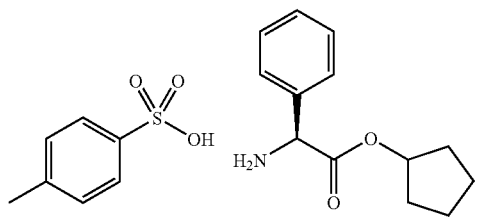

Intermediate 3c

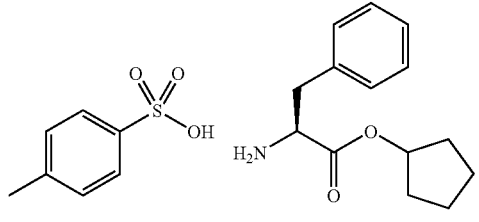

Intermediate 3d

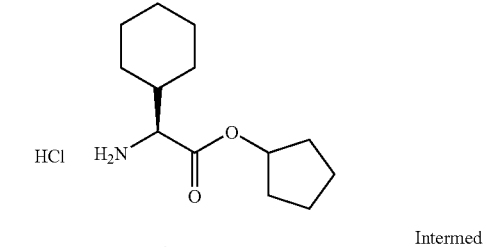

Intermediate 3e

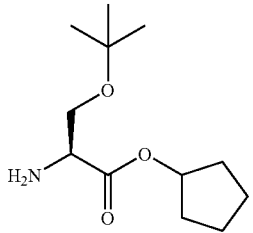

Intermediate 3f

Intermediate 3g

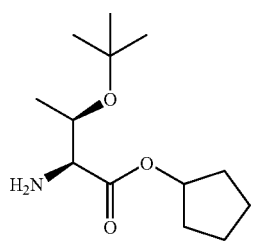

Intermediate 3h

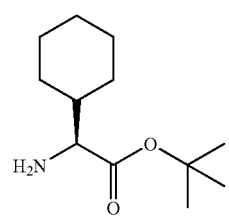

Intermediate 3i

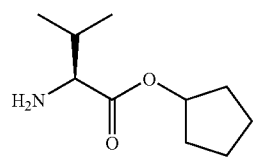

Synthesis of Compounds Outlined in List 1

Route I (Exemplified for Intermediate 3e)

Stage 1—Ester Formation

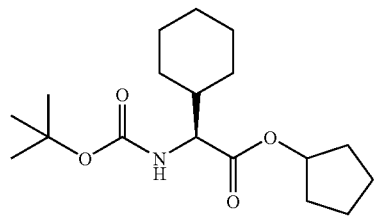

To a solution of (S)-2-tert-butoxycarbonylamino-3-cyclohexyl-propionic acid (5 g, 19.4 mmol) in DMF (50 ml) at 0° C. was added cyclopentanol (8.8 ml, 97.15 mmol), EDCI (4.09 g, 21.37 mmol) and finally DMAP (237 mg, 1.94 mmol). The reaction mixture was warmed to RT and stirred for 18 hr. The DMF was removed in vacuo to give a clear oil. This was separated between water and EtOAc. The organic phase was dried (MgSO$_4$) and concentrated in vacuo. The crude extract was purified by column chromatography (25% EtOAc in heptane) to yield the desired product as a clear oil (14.87 g, 55%). $^1$H NMR (300 MHz, d$_6$-DMSO) δ; 7.09 (1H, d), 5.08 (1H, t), 3.76 (1H, t), 1.50-1.85 (10H, br m), 1.39 (9H, s), 1.00-1.25 (9H, br m).

Stage 2 —Cyclopentyl (2S)-amino(cyclohexyl)acetate hydrochloride (Intermediate 3e)

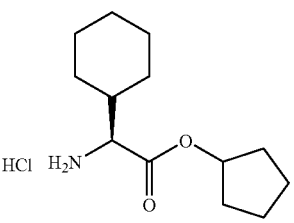

Stage 1 product (14.87 g, 45.69 mmol) was dissolved in DCM (100 ml) and treated with 4M HCl/dioxane (22.8 ml, 91.38 mmol) and the reaction mixture was stirred at RT for 24 hr. The crude mixture was concentrated under reduced pressure to give an orange oil. This was triturated with Et$_2$O to give a white precipitate. This was further washed with Et$_2$O to give the desired product as a white powder (7.78 g, 65%). $^1$H NMR (300 MHz, d$_6$-DMSO) δ; 8.45 (3H, br s), 5.22 (1H, t), 3.28 (1H, d), 1.95-1.50 (10H, br m), 1.30-0.90 (9H, br m).

Route II (Exemplified for Intermediate 3c)

Stage 1—(1S)-2-(cyclopentyloxy)-2-oxo-1-phenylethanaminium 4-methylbenzenesulfonate (Intermediate 3c)

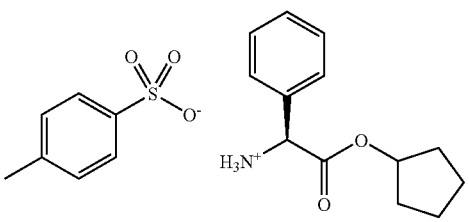

To a slurry of (S)-phenylglycine (5 g, 33.1 mmol) in cyclohexane (150 ml) was added cyclopentanol (29.84 ml, 331 mmol) and p-toluene sulfonic acid (6.92 g, 36.4 mmol). The reaction was fitted with a Dean-Stark receiver and heated to 135° C. for complete dissolution. After 12 hr, the reaction was cooled to RT leading to the precipitation of a white solid. The solid was filtered and washed with EtOAc before drying under reduced pressure to give the required product as a white powder (11.01 g, 85%). $^1$H NMR (300 MHz, d$_6$-DMSO) δ; 8.82 (2H, br s), 8.73 (1H, br s), 7.47 (7H, m), 7.11 (2H, d), 5.25 (1H, br s), 5.18 (1H, m), 2.29 (3H, s), 1.87-1.36 (8H, m).

The corresponding (R)-amino acid esters of the above intermediates can be prepared in a similar manner to shown above, starting from the relevant commercially available (R)-amino acids. In addition, the corresponding Leucine and Phenylglycine tert-butyl esters are commercially available and are used directly where appropriate.

Intermediate 4a Cyclopentyl N-[3-(dihydroxyboryl)benzyl]-L-leucinate

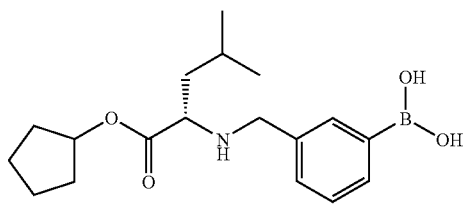

The synthesis of Intermediate 4a follows the synthetic route shown in Scheme 2.

To a solution of Intermediate 3a (244.6 mg, 1.227 mmol) and (3-formylphenyl) boronic acid (184 mg, 1.227 mmol) in DCM (10 ml) was added NaBH(OAc)$_3$ (780 mg, 3.68 mmol) in portions over 20 minutes. The reaction was stirred at RT for 2 hr after which time the reaction mixture was poured into 1M HCl (50 ml) and was washed with DCM (50 ml). The aqueous phase was neutralised to pH 7 with NaHCO$_3$ and extracted with DCM (2×50 ml). The combined organic extracts were dried over magnesium sulphate and the solvent removed. The product (270.3 mg, 0.811 mmol, 66.1% yield) was isolated as a colourless foamy solid and was used directly. LCMS: m/z 334 [M+H]$^+$.

Intermediate 4b [3-({[(1S)-2-(cyclopentyloxy)-2-oxo-1-phenylethyl]amino}methyl)phenyl]boronic acid

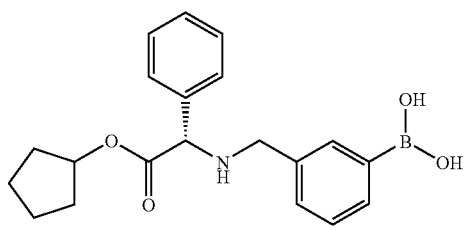

The synthesis to Intermediate 4b follows a similar synthetic route for Intermediate 4a using Intermediate 3c in Scheme 2.

LCMS: m/z 354 [M+H]$^+$.

Intermediate 4c [3-({[(1S)-1-cyclohexyl-2-(cyclopentyloxy)-2-oxoethyl]amino}methyl)phenyl]boronic acid

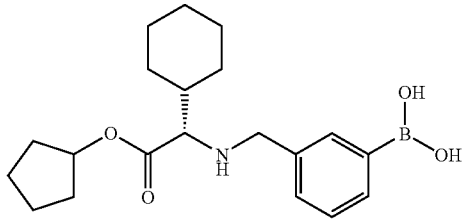

The synthesis to Intermediate 4c follows a similar synthetic route for Intermediate 4a using Intermediate 3e in Scheme 2.

LCMS: m/z 360 [M+H]$^+$.

Intermediate 4d Cyclopentyl O-tert-butyl-N-[3-(dihydroxyboranyl)benzyl]-L-serinate

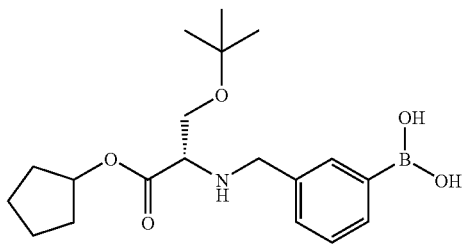

The synthesis to Intermediate 4d follows a similar synthetic route for Intermediate 4a using Intermediate 3f in Scheme 2.

LCMS: m/z 364 [M+H]$^+$.

Intermediate 4e Cyclopentyl O-tert-butyl-N-[3-(dihydroxyboranyl)benzyl]-L-threoninate

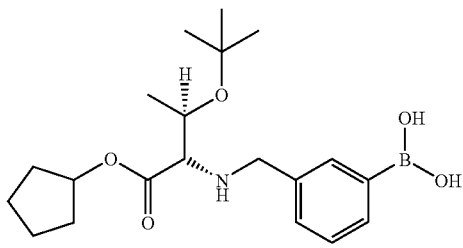

The synthesis to Intermediate 4e follows a similar synthetic route for Intermediate 4a using Intermediate 3 g in Scheme 2.

LCMS: m/z 322 [M+H]$^+$.

Intermediate 4f Cyclopentyl N-[3-(dihydroxyboranyl)benzyl]-L-valinate

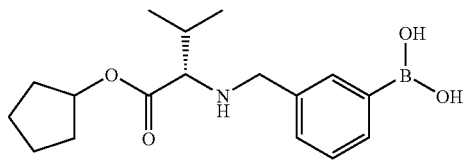

The synthesis to Intermediate 4f follows a similar synthetic route for Intermediate 4a using Intermediate 3i in Scheme 2.
LCMS: m/z 320 [M+H]$^+$.

Intermediate 5a Cyclopentyl N-[3-chloro-4-(4,4,5,5-tetramethyl-1,3,2-dioxaborolan-2-yl)benzyl]-L-leucinate

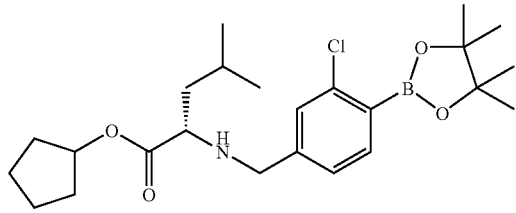

The synthesis to Intermediate 5a follows the synthetic route shown in Scheme 3.

To a flask containing (S)-2-(4-Bromo-3-chloro-benzylamino)-4-methyl-pentanoic acid cyclopentyl ester (715 mg, 1.775 mmol), Bis[pinacolato]diboron (90 mg, 3.55 mmol), PdCl$_2$(dppf) (130 mg, 0.178 mmol) and potassium acetate (348 mg, 3.55 mmol) was added DMSO (10 ml, dry) and the reaction vessel purged thoroughly with N$_2$. The reaction mixture was placed in a preheated oil bath at 80° C. Analysis after 2 hours showed the desired product in addition to residual starting material. The reaction was left at 80° C. for a further 3 hrs. The reaction mixture was cooled to RT and poured into water (10 ml). The product was extracted into Et$_2$O and the combined organic extracts were washed with water and brine, dried over magnesium sulphate and the solvent removed. The residue was purified by column chromatography eluting with 10-20% EtOAc in hexanes to yield 150 mg of a colourless oil. Further purification by capture and release on SCX gave 62 mg, 0.131 mmol, 7.4% yield. LCMS: m/z 450 [M+H]$^+$.

The (S)-2-(4-Bromo-3-chloro-benzylamino)-4-methyl-pentanoic acid cyclopentyl ester was prepared as shown below.

To a vial containing 4-bromo-3-chloro-benzaldehyde (0.5 g, 2.278 mmol) and Intermediate 3a (0.537 g, 2.278 mmol) was added DCM (10 ml) and stirred at RT for 20 minutes, after which time NaBH(OAc)$_3$ (1.45 g, 6.83 mmol) was added portion wise. The reaction was stirred at RT for 2 hrs. The reaction mixture was poured into 2M HCl and extracted with DCM. The aqueous layer was neutralised with NaHCO$_3$ and re-extracted into DCM. The combined organic extracts were washed with water, dried over magnesium sulphate and solvent removed in vacuo to give 900 mg of a colourless oil. Analysis by LCMS showed the desired product together with unreacted Intermediate 3a. The product was purified by column chromatography eluting with 50-100% DCM in hexanes to give 715 mg, 1.243 mmol, 54.5% yield as a colourless oil. LCMS: m/z 401.8/403.8 [M+H]$^+$.

The 4-bromo-3-chloro-benzaldehyde was prepared as shown below.

4-Bromo-3-amino-benzaldehyde (1.39 g, 6.95 mmol) was dissolved in HCl (conc) (15 ml) and treated with sodium nitrite (0.504 g, 7.30 mmol) at 0° C. The reaction was stirred for 30 minutes, then left to warm to RT for 30 minutes. The mixture was added cold to a stirred solution of copper chloride (0.964 g, 9.74 mmol) in HCl (conc) (10 ml) at RT. The green solution was heated to 60° C. for 45 minutes then allowed to cool. The reaction mixture was poured into water and extracted into EtOAc. The combined organic layers were washed with water, NaHCO$_3$ and brine, dried over magnesium sulphate and solvent removed in vacuo to give 1.2 g of a brown oil. The product was purified by column chromatography eluting with 10% EtOAc in hexanes. Product isolated as a colourless waxy solid (1.061 g, 4.50 mmol, 64.7% yield).

Intermediate 5b Cyclopentyl N-[2-methyl-4-(4,4,5,5-tetramethyl-1,3,2-dioxaborolan-2-yl)benzyl]-L-leucinate

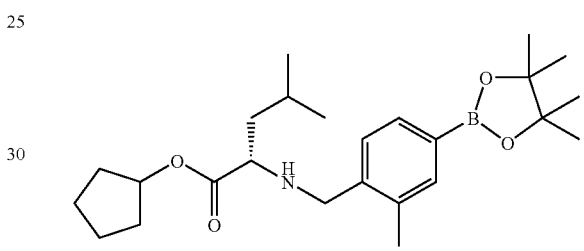

Synthesised via analogous methods to Intermediate 5a, using 4-bromo-2-methyl-benzaldehyde in Scheme 3.
LCMS: m/z 430 [M+H]$^+$.

Intermediate 6a Cyclopentyl N-{2-[4-(4,4,5,5-tetramethyl-1,3,2-dioxaborolan-2-yl)phenyl]ethyl}-L-leucinate

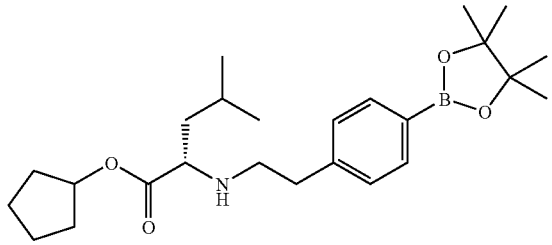

The synthesis to Intermediate 6a follows the synthetic route shown in Scheme 4.

A vial charged with (S)-2-[2-(4-Bromo-phenyl)-ethylamino]-4-methyl-pentanoic acid cyclopentyl ester (320 mg, 0.837 mmol), Bis[pinacolato]diboron (319 mg, 1.255 mmol), PdCl$_2$(dppf) (30 mg, 5 mol %) and KOAc (123 mg, 1.255 mmol) was flushed with nitrogen and DMSO (dry, 2 ml) was added. The reaction mixture was stirred at 80° C. for 5 hrs and was judged to be complete by LCMS. The mixture was cooled to RT, poured onto water and extracted with ether. The combined organic layers were washed with water (×3) and brine, dried (MgSO$_4$), filtered and evaporated in vacuo to give a dark oily residue 467.2 mg. The dark residue was purified by column chromatography eluting with 10% EtOAc in hexanes to give the product as a colourless oil 223 mg (62%). LCMS: m/z 430 [M+H]+.

The (S)-2-[2-(4-Bromo-phenyl)-ethylamino]-4-methyl-pentanoic acid cyclopentyl ester was prepared as detailed below.

To a stirred solution of Intermediate 3a (500 mg, 2.509 mmol) and 4-bromophenylacetaldehyde (510 mg, 2.56 mmol) in DCM (15 ml) under an inert atmosphere at RT, was added NaBH(OAc)$_3$ (1.595 g, 7.53 mmol) over a period of 20 minutes and stirred at RT for 30 minutes. To the reaction mixture was added 2M HCl (50 ml) and extracted with DCM (50 ml×2). The DCM layer was dried over MgSO$_4$ and the solvent removed to give 994 mg of an oily colourless solid, capture and release on SCX gave the product as a pale yellow oil (320 mg, 33%). LCMS: m/z 384 [M+H].

Intermediate 6b Cyclopentyl N-{2-[3-chloro-4-(4,4,5,5-tetramethyl-1,3,2-dioxaborolan-2-yl)phenyl]ethyl}-L-leucinate

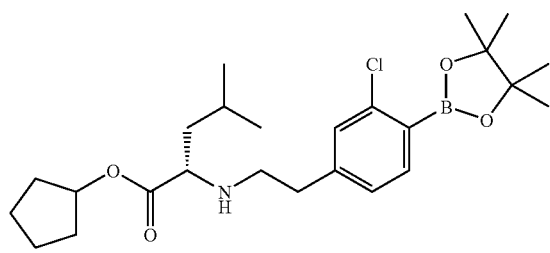

Synthesised via analogous methods to Intermediate 6a, using 4-bromo-3-chloro-phenylacetaldehyde in Scheme 4.
LCMS: m/z 464 [M+H]+.

Intermediate 6c Cyclopentyl N-{2-[3-(4,4,5,5-tetramethyl-1,3,2-dioxaborolan-2-yl)phenyl]ethyl}-L-leucinate

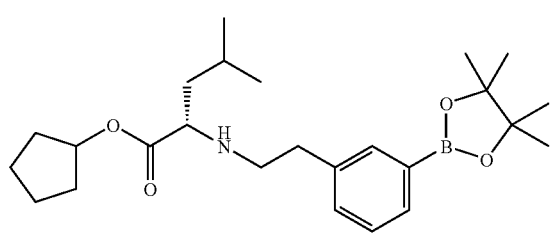

Synthesised via analogous methods to Intermediate 6a, using 3-bromophenylacetaldehyde in Scheme 4.
LCMS: m/z 430 [M+H]+.

Intermediate 6d Cyclopentyl (2S)-phenyl({2-[3-(4,4,5,5-tetramethyl-1,3,2-dioxaborolan-2-yl)phenyl]ethyl}amino)acetate

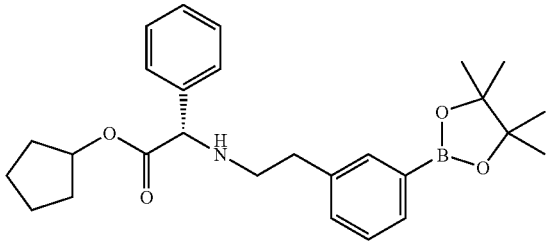

Synthesised via analogous methods to Intermediate 6a, using 3-bromophenylacetaldehyde and Intermediate 3c in Scheme 4.
LCMS: m/z 450 [M+H]+.

Intermediate 6e Cyclopentyl O-tert-butyl-N-{2-[3-(4,4,5,5-tetramethyl-1,3,2-dioxaborolan-2-yl)phenyl]ethyl}-L-serinate

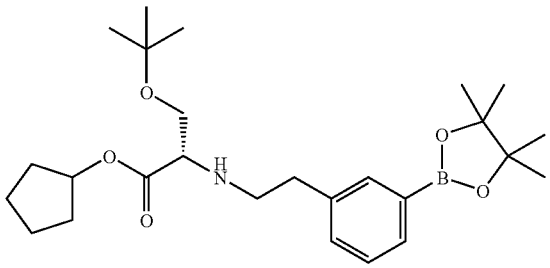

Synthesised via analogous methods to Intermediate 6a, using 3-bromophenylacetaldehyde and Intermediate 3f in Scheme 4.
LCMS: m/z 460 [M+H]+.

Intermediate 6f Cyclopentyl O-tert-butyl-N-{2-[3-(4,4,5,5-tetramethyl-1,3,2-dioxaborolan-2-yl)phenyl]ethyl}-L-threoninate

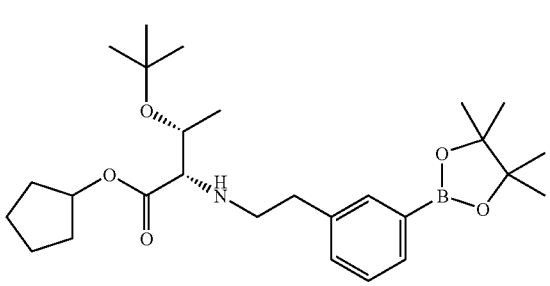

Synthesised via analogous methods to Intermediate 6a, using 3-bromophenylacetaldehyde and Intermediate 3 g in Scheme 4.
LCMS: m/z 474 [M+H]+.

Intermediate 7a Cyclopentyl N-{3-[4-(4,4,5,5-tetramethyl-1,3,2-dioxaborolan-2-yl)phenoxy]propyl}-L-leucinate

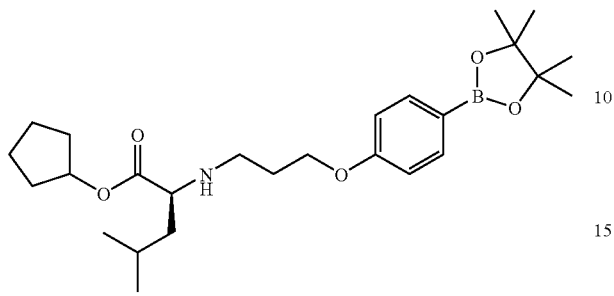

The synthetic route to Intermediate 7a is shown in Scheme 5.

To a mixture of (S)-2-[3-(4-Bromo-phenoxy)-propylamino]-4-methyl-pentanoic acid cyclopentyl ester (0.37 g, 0.897 mmol), Bis[pinacolato]diboron (0.684 g, 2.69 mmol), PdCl$_2$(dppf) (0.066 g, 0.090 mmol) and KOAc (0.264 g, 2.69 mmol) was added DMSO (2 ml). The mixture was purged with nitrogen and placed in a preheated oil bath at 80° C. After 4 hrs the reaction was judged to be complete by LC-MS. The mixture was cooled to RT and poured onto a mixture of ether and water. The aqueous phase was extracted with ether and the combined organics washed with water (×4) and brine. After drying and evaporating the residue was subjected to column chromatography eluting with 5 to 10% EtOAc in hexanes. Yield=0.2 g, 0.435 mmol, 48.5% yield. LCMS: m/z 460 [M+H]$^+$.

The (S)-2-[3-(4-Bromo-phenoxy)-propylamino]-4-methyl-pentanoic acid cyclopentyl ester was prepared as shown below.

To a solution of Intermediate 3a (0.365 g, 1.833 mmol) and 3-(4-bromo-phenoxy)-propionaldehyde (0.6 g, 1.833 mmol) in DCM (15 ml) was added NaBH(OAc)$_3$ (1.166 g, 5.50 mmol). Upon stirring at RT for 2 hrs the reaction was judged to be complete by LC-MS. 1M HCl (10 ml) was added to the reaction mixture and stirred rapidly for 10 minutes. The mixture was poured onto sat. NaHCO$_3$ and extracted with DCM. The combined organic layers were dried over magnesium sulphate, filtered and evaporated. The residue was subjected to column chromatography eluting with 10% EtOAc in hexanes. Yield=0.375 g, 0.818 mmol, 44.6% yield. LCMS: m/z 412 and 414 [M+H]$^+$.

The 3-(4-Bromo-phenoxy)-propionaldehyde was prepared as shown below.

2-[3-(4-Bromo-phenoxy)-propyl]-[1,3]dioxolane (1.5 g, 5.49 mmol) was dissolved in acetone (15 ml) and treated with water (10 ml). HCl (14.98 ml, 165 mmol) was added to the solution. Upon stirring at RT for 1 hr the reaction was judged to be complete by TLC (20% EtOAc in hexanes). The mixture was poured onto water and extracted with ether. The combined organic layers were washed with 2M NaOH, water and brine, dried over magnesium sulphate, filtered and evaporated in vacuo. Yield=0.6 g, 1.833 mmol, 33.4% yield.

The 2-[3-(4-Bromo-phenoxy)-propyl]-[1,3]dioxolane was prepared as shown below.

To a mixture of 4-bromophenol (10 g, 57.8 mmol), TBAI (0.813 g, 5.78 mmol) and K$_2$CO$_3$ (7.99 g, 57.8 mmol) in DMF (50 ml) was added 2-(3-bromo-propyl)-[1,3]dioxolane (10.19 ml, 87 mmol). The mixture was placed in a preheated oil bath at 50° C. for 3 hrs. The mixture was cooled to RT, poured onto 2M NaOH and extracted with ether. The combined organic layers were washed with further 2M NaOH, 1M HCl (×2), water (×2) and brine. After drying over magnesium sulphate, filtration and evaporation in vacuo, the residue was absorbed onto silica and subjected to column chromatography eluting with 6% EtOAc in hexanes to give a white solid. Yield=12.5 g, 43.5 mmol, 75% yield.

Intermediate 7b Cyclopentyl N-{3-[3-chloro-4-(4,4,5,5-tetramethyl-1,3,2-dioxaborolan-2-yl)phenoxy]propyl}-L-leucinate

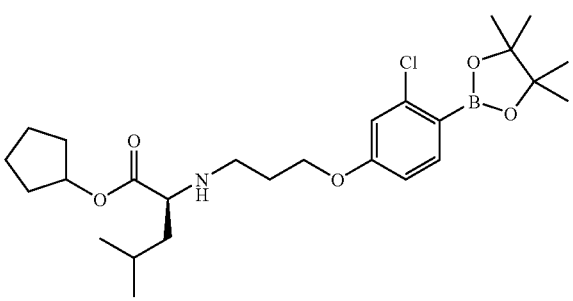

Synthesised via analogous methods to Intermediate 7a, using 4-bromo-3-chlorophenol in Scheme 5.
LCMS: m/z 494 [M+H]$^+$.

Intermediate 8a Cyclopentyl N-{5-[4-(4,4,5,5-tetramethyl-1,3,2-dioxaborolan-2-yl)phenoxy]pentyl}-L-leucinate

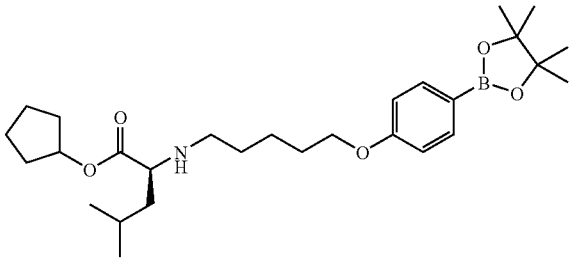

The synthetic route to Intermediate 8a is shown in Scheme 6.

To a mixture of (S)-2-[5-(4-Bromo-phenoxy)-pentylamino]-4-methyl-pentanoic acid cyclopentyl ester (0.63 g, 1.430 mmol), Bis[pinacolato]diboron (0.908 g, 3.58 mmol), PdCl$_2$(dppf) (0.105 g, 0.143 mmol) and KOAc (0.351 g, 3.58 mmol) was added DMSO (5 ml). The mixture was purged with nitrogen and placed in a preheated oil bath at 80° C. After heating for 4 hrs the reaction was judged to be complete by LC-MS. The mixture was poured onto water and extracted with ether. The combined organics were washed with water (×3) and brine, dried (MgSO$_4$), filtered and evaporated under reduced pressure, and subjected to column chromatography eluting with 10% EtOAc in hexanes. Yield=0.61 g, 1.214 mmol, 85% yield. LCMS purity 97%: m/z 488 [M+H]$^+$.

The (S)-2-[5-(4-Bromo-phenoxy)-pentylamino]-4-methyl-pentanoic acid cyclopentyl ester was prepared as shown below.

DIPEA (2.2 ml, 13.01 mmol) was added to a mixture of Intermediate 3a (2.3 g, 9.76 mmol) and TBAI (0.458 g, 3.25 mmol) in DMF (5 ml). A solution of 1-Bromo-4-(5-chloro-pentyloxy)-benzene (0.903 g, 3.25 mmol) in DMF (2 ml) was added to the mixture and placed in a preheated oil bath at 95° C. The mixture was stirred overnight. LC-MS indicated ~60% conversion. The mixture was poured onto water and extracted with ether and the combined organic layers washed with sat. NaHCO$_3$, water (×2) and brine. After drying (MgSO$_4$) and evaporation under reduced pressure, the residue was subjected to column chromatography eluting with 10 to 15% EtOAc in hexanes. Yield=0.64 g, 1.381 mmol, 42.5% yield.

The 1-Bromo-4-(5-chloro-pentyloxy)-benzene was prepared via a similar procedure to the synthesis of 2-[3-(4-Bromo-phenoxy)-propyl]-[1,3]dioxolane already described above. LCMS purity 95%: m/z 440 and 442 [M+H]$^+$.

Intermediate 8b Cyclopentyl N-{5-[3-chloro-4-(4,4,5,5-tetramethyl-1,3,2-dioxaborolan-2-yl)phenoxy]pentyl}-L-leucinate

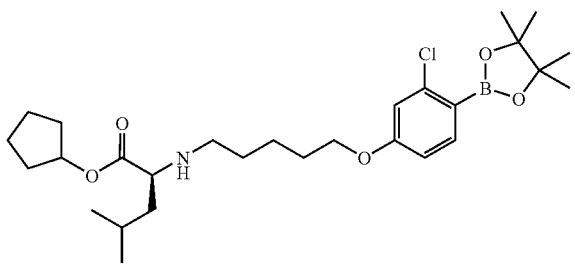

Synthesised via analogous methods to Intermediate 8a, using 1-Bromo-2-chloro-4-(5-chloro-pentyloxy)-benzene in Scheme 6.

LCMS purity 98%: m/z 522 [M+H]$^+$.

Intermediate 9a Cyclopentyl N-(tert-butoxycarbonyl)-N-{(2E)-3-[4-(4,4,5,5-tetramethyl-1,3,2-dioxaborolan-2-yl)phenyl]prop-2-en-1-yl}-L-leucinate

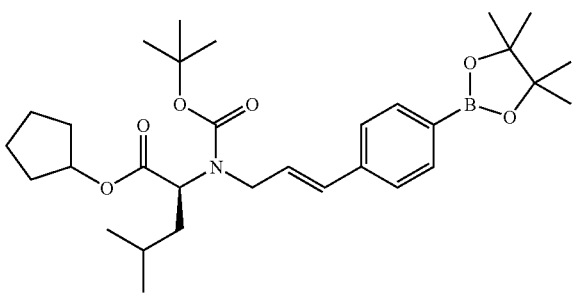

The synthetic route to Intermediate 9a is shown in Scheme 7.

A mixture of cyclopentyl N-[(2E)-3-(4-bromophenyl)prop-2-en-1-yl]-N-(tert-butoxycarbonyl)-L-leucinate (204 mg, 0.413 mmol), Bis[pinacolato]diboron (157 mg, 0.619 mmol), potassium acetate (60.7 mg, 0.619 mmol) and PdCl$_2$(dppf) (16.85 mg, 0.021 mmol) were suspended in DMSO (1.6 ml) and purged with nitrogen. The reaction mixture was heated to an oil bath temperature of 50° C. and left to stir overnight. The reaction mixture was partitioned between ether and water. The aqueous layer was extracted with a further portion of ether. The combined organic layers were washed with brine, dried over MgSO$_4$ and concentrated in vacuo to afford a brown residue. The residue was purified by column chromatography, eluting with 5% ethyl acetate in isohexane. The required product was isolated as a clear colourless oil (102 mg, 0.188 mmol, 46%). LCMS purity 100%: m/z 542.1 [M+H]$^+$.

The cyclopentyl N-[(2E)-3-(4-bromophenyl)prop-2-en-1-yl]-N-(tert-butoxycarbonyl)-L-leucinate was prepared as shown below.

A mixture of cyclopentyl N-allyl-N-(tert-butoxycarbonyl)-L-leucinate (1 g, 2.95 mmol), 4-Bromo-iodobenzene (0.917 g, 3.24 mmol), palladium(II) acetate (0.066 g, 0.295 mmol), TBAI (1.197 g, 3.24 mmol) and sodium bicarbonate (0.742 g, 8.84 mmol) was suspended in dry acetonitrile (10 ml). The mixture was purged with nitrogen and placed in a preheated oil bath at 70° C. The reaction was left to stir for 2 hrs. LCMS confirmed incomplete reaction so a further 3 mg of palladium(11) acetate was added to the reaction mixture. After a further 3 hrs, the reaction mixture was left to stand and cool to RT. The crude reaction mixture was diluted with acetonitrile and adsorbed onto silica before column chromatography, eluting with 5% ethyl acetate in isohexane. The required product was isolated as a colourless oil (220 mg, 0.445 mmol, 15% yield). LCMS purity 100%: m/z 494.0, 496.0 [M+H]$^+$.

The cyclopentyl N-allyl-N-(tent-butoxycarbonyl)-L-leucinate was prepared as shown below.

Cyclopentyl N-allyl-L-leucinate (2 g, 8.36 mmol) and Boc-anhydride (1.824 g, 8.36 mmol) were added together in a vial which was then capped with a septum. The reaction mixture was left to stir overnight. The reaction mixture was partitioned between ether and water. The organic phase was washed sequentially with 1M HCl, saturated NaHCO$_3$ and brine, dried over MgSO$_4$ and concentrated in vacuo to afford a colourless oil (2.66 g, 7.84 mmol, 94%). LCMS purity 100%: m/z 340.2 [M+H]$^+$.

The cyclopentyl N-allyl-L-leucinate was prepared as shown below.

A suspension of lithium hydroxide hydrate (2.72 g, 64.7 mmol) and 4 Å sieve dust (15 g) were stirred in DMF (150 ml) for 20 minutes. Intermediate 3a (free base) (6 g, 30.1 mmol) was added and stirring continued for 40 minutes. Allyl bromide (3.13 ml, 36.1 mmol) was then added and the mixture stirred overnight at RT. LCMS showed the formation of product with some di-alkylated product. The mixture was filtered, poured onto water and extracted (×3) with ether. The combined organic layers were washed with water (×3) and brine, dried over magnesium sulphate, filtered and evaporated in vacuo. The residue was subjected to column chromatography eluting with 5% EtOAc in hexanes. The product was isolated as a colourless oil. Yield=4.34 g, 18.13 mmol, 60.2% yield. LCMS: m/z 240.1 [M+H]$^+$.

Intermediate 9b tert-butyl N-{(2E)-3-[4-(4,4,5,5-tetramethyl-1,3,2-dioxaborolan-2-yl)phenyl]prop-2-en-1-yl}-L-leucinate

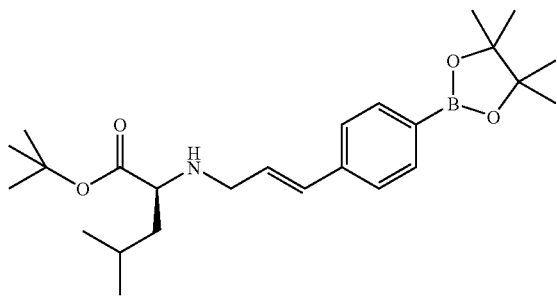

The synthetic route to Intermediate 9b is shown in Scheme 8.

Bispinacolatodiboron (0.897 g, 3.53 mmol), PdCl₂(dppf) (0.120 g, 0.165 mmol) and KOAc (0.347 g, 3.53 mmol) were added to a solution of tert-butyl N-[(2E)-3-(4-bromophenyl)prop-2-en-1-yl]-leucinate (0.9 g, 2.354 mmol) in DMSO (5 ml) and the flask evacuated, and refilled with nitrogen. The reaction was then heated at 80° C. for 3 hours. The reaction was poured onto water (50 ml) and the product extracted with EtOAc (2×50 ml). The combined organics were then washed with water (2×25 ml) and brine (25 ml), dried (MgSO₄) and concentrated in vacuo to give a black oil. The crude material was purified by column chromatography and the product eluted with 10% EtOAc in i-hexane to give a yellow oil. (0.62 g, 1.444 mmol, 61.3% yield). LCMS: m/z 430 [M+H]⁺.

The tert-butyl N-[(2E)-3-(4-bromophenyl)prop-2-en-1-yl]-L-leucinate was prepared as shown below.

To a mixture of (E)-3-(4-Bromo-phenyl)-propenal (0.75 g, 3.20 mmol) and t-butyl-L-leucinate (1.073 g, 4.80 mmol) was added THF (20 ml) followed by ~5 g of 4 Å sieve dust. The vessel was flushed with nitrogen and placed in a preheated oil bath at 60° C. for 70 minutes after which time the reaction was complete. The mixture was cooled in an ice bath and treated with Na(OAc)₃BH (3.39 g, 15.99 mmol) in a single portion. After stirring for 30 minutes, water (1 ml) and MOH (3 ml) was added to aid solubility. After stirring for another 40 minutes the reaction was judged to be complete by TLC (20% EtOAc in hexanes). 1M HCl (50 ml) was added to the mixture and the mixture was then poured onto sat. NaHCO₃ and extracted with ether. The combined organic extracts were dried over magnesium sulphate, filtered and evaporated in vacuo before purification by column chromatography eluting with 10 to 20% EtOAc in hexanes. Yield=1 g, 2.354 mmol, 73.6% yield. LCMS: m/z 382 [M+H]⁺.

The (E)-3-(4-Bromo-phenyl)-propenal was prepared as shown below.

To a solution of (E)-3-(4-Bromo-phenyl)-prop-2-en-1-ol (1 g, 4.69 mmol) in DME (20 ml) was added manganese dioxide (8.16 g, 94 mmol). After stirring at RT for 1 hr the reaction was judged to be complete by TLC (20% EtOAc in hexanes). The mixture was filtered through a pad of celite, washing with DME (2×15 ml). After evaporation in vacuo a colourless solid was obtained. Yield=0.95 g, 4.50 mmol, 96% yield.

The (E)-3-(4-Bromo-phenyl)-prop-2-en-1-ol was prepared as shown below.

To a solution of (E)-3-(4-Bromo-phenyl)-acrylic acid ethyl ester (13.5 g, 52.9 mmol) under nitrogen at −78° C. was added dropwise DIBAL in toluene (159 ml, 159 mmol) over 1 hr. After the addition, the solution was stirred for a further 1 hr at the same temperature and then allowed to warm to −50° C. for 5 minutes. 1M HCl (200 ml) was added dropwise while the reaction mixture warmed to RT. After rapidly stirring for 30 minutes at RT, EtOAc (500 ml) was added and the organic layer collected. The aqueous layer was extracted with further EtOAc. The combined organic phases were washed with further 1M HCl and brine, dried over magnesium sulphate, filtered and evaporated in vacuo. The residue was triturated from hexanes (100 ml) to give a white solid, collected by filtration and washed with hexanes (200 ml). Yield=9.8 g, 46.0 mmol, 87% yield.

Intermediate 9c Cyclopentyl (2S)-phenyl({(2E)-3-[4-(4,4,5,5-tetramethyl-1,3,2-dioxaborolan-2-yl)phenyl]prop-2-en-1-yl}amino)ethanoate

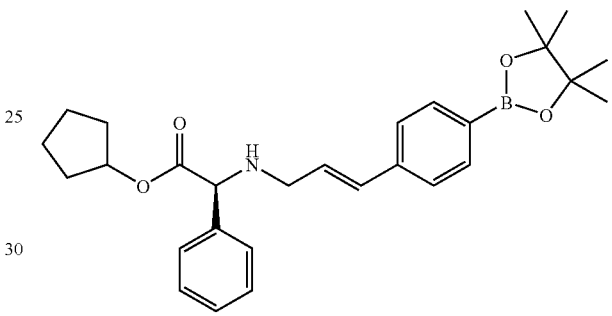

The synthetic route to Intermediate 9c is similar to Intermediate 9b using Intermediate 3c in Scheme 8.

LCMS: m/z 462 [M+H]⁺.

Intermediate 9d cyclopentyl (2S)-cyclohexyl({(2E)-3-[4-(4,4,5,5-tetramethyl-1,3,2-dioxaborolan-2-yl)phenyl]prop-2-en-1-yl}amino)ethanoate

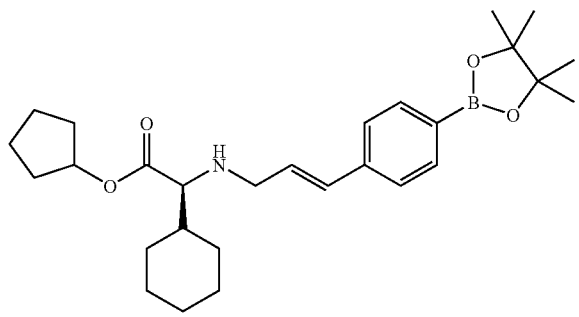

The synthetic route to Intermediate 9d is similar to Intermediate 9b using Intermediate 3e in Scheme 8.

LCMS: m/z 468 [M+H]⁺.

Intermediate 9e Cyclopentyl O-tert-butyl-N-{(2E)-3-[4-(4,4,5,5-tetramethyl-1,3,2-dioxaborolan-2-yl)phenyl]prop-2-en-1-yl}-L-serinate

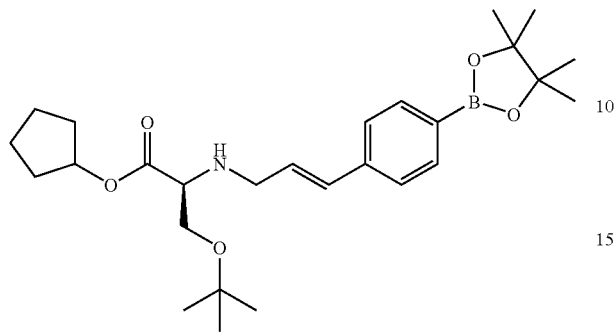

The synthetic route to Intermediate 9e is similar to Intermediate 9b using Intermediate 3f in Scheme 8.
LCMS: m/z 472 [M+H]$^+$.

Intermediate 9f tert-butyl N-{(2E)-3-[4-(4,4,5,5-tetramethyl-1,3,2-dioxaborolan-2-yl)phenyl]grog-2-en-1-yl}-D-leucinate

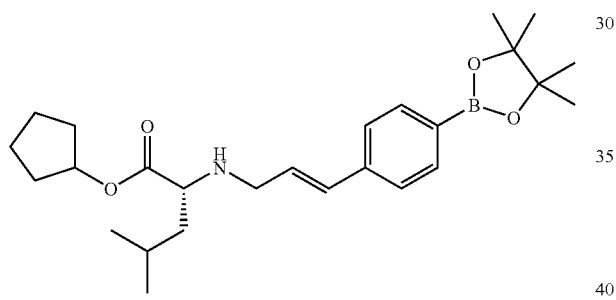

The synthetic route to Intermediate 9f is similar to Intermediate 9b using cyclopentyl-D-leucinate in Scheme 8.
LCMS: m/z 442 [M+H]$^+$.

Intermediate 9g tert-butyl(2S)-cyclohexyl({(2E)-3-[4-(4,4,5,5-tetramethyl-1,3,2-dioxaborolan-2-yl)phenyl]prop-2-en-1-yl}amino)ethanoate

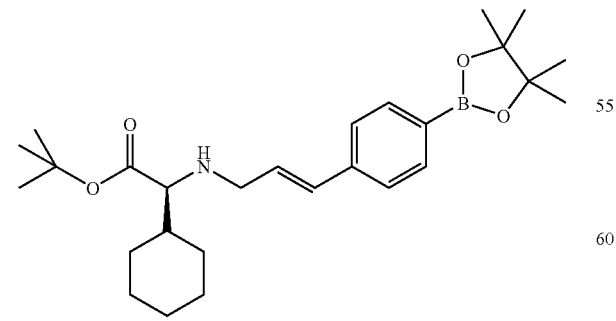

The synthetic route to Intermediate 9g is similar to Intermediate 9b using Intermediate 3h in Scheme 8.
LCMS: m/z 468 [M+H]$^+$.

Intermediate 9h Cyclopentyl O-tert-butyl-N-{(2E)-3-[4-(4,4,5,5-tetramethyl-1,3,2-dioxaborolan-2-yl)phenyl]prop-2-en-1-yl}-L-threoninate

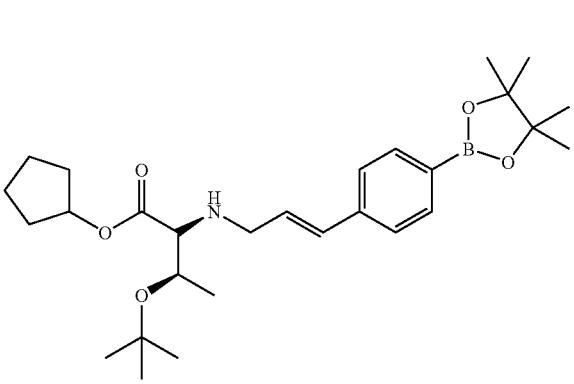

The synthetic route to Intermediate 9g is similar to Intermediate 9b using Intermediate 3g in Scheme 8.
LCMS: m/z 486 [M+H]$^+$.

Intermediate 10 Cyclopentyl N-{2E)-3-[3-(4,4,5,5-tetramethyl-1,3,2-dioxaborolan-2-yl)phenyl]prop-2-en-1-yl}-L-leucinate

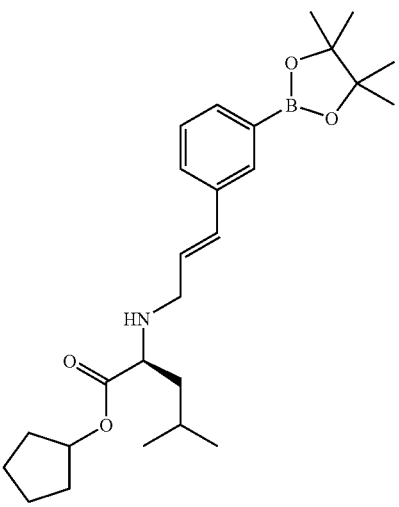

The synthetic route to Intermediate 10 is similar to Intermediate 9a using 3-bromo-iodobenzene in Scheme 7.
LCMS: m/z 442 [M+H]$^+$.

Intermediate 11a Cyclopentyl N-{2-[2-fluoro-5-(4,4,5,5-tetramethyl-1,3,2-dioxaborolan-2-yl)phenyl]ethyl}-L-leucinate

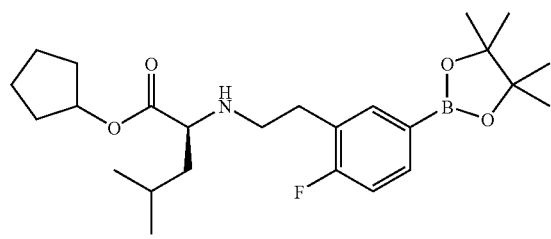

The synthetic route to Intermediate 11a is shown in Scheme 9.

Cyclopentyl N-{2-[2-fluoro-5-bromophenyl]ethyl}-L-leucinate (450 mg, 1.124 mmol), Bis-pinacolatodiboron (428 mg, 1.686 mmol), PdCl$_2$(dppf) (92 mg, 0.112 mmol) and potassium acetate (276 mg, 2.81 mmol) were combined in a dry vessel and purged with N$_2$. DMSO (3 ml) was added and the mixture heated at 80° C. for 18 hr for complete reaction. The mixture was partitioned between Et$_2$O (50 ml) and water (100 ml) and the phases separated. The aqueous phase was extracted with Et$_2$O (2×25 ml) and the combined organic phases washed with brine (3×100 ml), dried (MgSO$_4$) and evaporated in vacuo to afford the crude product as a yellow oil. Purification by column chromatography (5-10% EtOAc/isohexane) afforded the product (286 mg, 0.511 mmol, 45.5% yield) as a pale yellow oil. m/z 448 [M+H]$^+$.

Cyclopentyl N-{2-[2-fluoro-5-bromophenyl]ethyl}-L-leucinate was prepared as shown below.

(5-bromo-2-fluorophenyl)acetaldehyde (0.336 g, 1.548 mmol) was dissolved in DCM (12 ml) and treated with Intermediate 3a (0.719 g, 1.935 mmol). The resulting solution was stirred at RT for 20 min, and then treated with sodium triacetoxyborohydride (1.641 g, 7.74 mmol) portionwise. The mixture was stirred at room temperature for 2 hr for complete reaction. The mixture was quenched with 1 M HCl, then neutralised with NaHCO$_3$ solution. The mixture was diluted with DCM (75 ml) and the phases separated. The aqueous phase was extracted with DCM (25 ml) and the combined organic phases were washed with NaHCO$_3$ solution (100 ml) and brine (100 ml), dried (MgSO$_4$) and evaporated in vacuo to afford the crude product as a yellow oil. Purification by column chromatography (5% EtOAc/isohexane) afforded the product (450 mg, 0.877 mmol, 56.6% yield) as a pale yellow oil. m/z 400 [M+H]$^+$.

(5-bromo-2-fluorophenyl)acetaldehyde was prepared as shown below.

A solution of 4-bromo-2-ethenyl-1-fluorobenzene (1.3 g, 3.23 mmol) in DCM (10 ml) was added dropwise over 30 min to a solution of lead tetra-acetate (1.434 g, 3.23 mmol) in TFA (5 ml) at 0° C. The mixture was then allowed to warm to room temperature and stirred for 1.5 hr. TLC analysis suggested incomplete reaction so the mixture was stirred at RT for 18 hr. The mixture was poured onto water (50 ml) and stirred for 10 minutes, then extracted with DCM (50 ml). The organic phase was washed with NaHCO$_3$ solution (100 ml), brine (100 ml), dried (MgSO$_4$) and evaporated in vacuo to give the crude product as a yellow oil. Purification by column chromatography (0-5% EtOAc/isohexane) afforded the product (336 mg, 1.548 mmol, 47.9% yield) as a pale yellow oil.

4-bromo-2-ethenyl-1-fluorobenzene was prepared as shown below.

Methyl triphenylphosphonium bromide (6.60 g, 18.47 mmol) in THF (40 ml) was treated dropwise with 1M LiHMDS (18.47 ml, 18.47 mmol) at −10° C. and the resulting solution stirred at this temperature for 30 min, then cooled to −78° C. A solution of 5-bromo-2-fluorobenzaldehyde (2.5 g, 12.31 mmol) in THF (10 ml) was then added dropwise. The mixture was stirred at −78° C. for 10 min, then allowed to warm to room temperature and stirred for a further 3 hrs. The mixture was poured onto water (200 ml) and extracted into isohexane (2×200 ml). The combined organic phases were washed with brine (200 ml), dried (MgSO$_4$) and evaporated in vacuo to afford the crude product. Purification by column chromatography afforded the product (1.34 g, 3.33 mmol, 27.1% yield) as a clear colourless oil.

Intermediate 11b Cyclopentyl N-{2-[2-methyl-5-(4,4,5,5-tetramethyl-1,3,2-dioxaborolan-2-yl)phenyl]ethyl}-L-leucinate

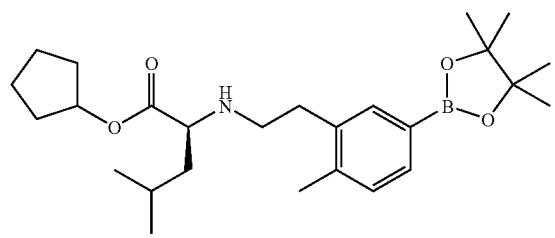

The synthesis of Intermediate 11b is similar to Intermediate 11a using 5-bromo-2-methylbenzaldehyde in Scheme 9. LCMS: m/z 444 [M+H]$^+$.

Intermediate 11c Cyclopentyl N-{2-[2-chloro-5-(4,4,5,5-tetramethyl-1,3,2-dioxaborolan-2-yl)phenyl]ethyl}-L-leucinate

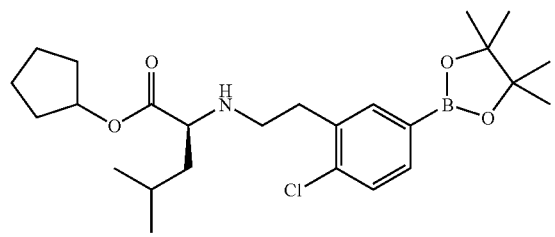

The synthesis of Intermediate 11c is similar to Intermediate 11a using 5-bromo-2-chlorobenzaldehyde in Scheme 9. LCMS: m/z 464 [M+H]$^+$.

EXAMPLES

The following examples illustrate the preparation of the specific compounds of the invention, and the IKK inhibitory properties thereof:

Example 1

Cyclopentyl (2S)-({-4-[4-carbamoyl-5-(carbamoylamino)-2-thienyl]benzyl}amino)(phenyl)acetate

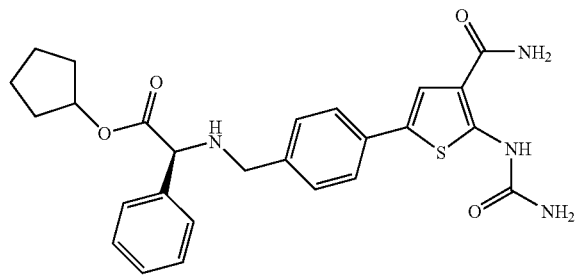

LC/MS purity 95%, m/z 493 [M+H]+, $^1$H NMR (400 MHz, DMSO-$d_6$), δ: 11.0 (1H, s), 7.8 (1H, s), 7.72 (2H, br s), 7.6 (2H, d, J=8.8 Hz), 7.46 (2H, d, J=8.3 Hz), 7.5-7.3 (5H, m), 7.0 (2H, s), 5.1 (1H, m), 4.2 (1H, s), 3.6 (2H, s), 3.0 (1H, s), 1.9-1.4 (8H, m).

To a solution of 5-(4-Formyl-phenyl)-2-ureido-thiophene-3-carboxylic acid amide (Intermediate 2) (0.15 g, 0.518 mmol) and Intermediate 3c (0.227 g, 1.037 mmol) in tetrahydrofuran (4.5 ml) under nitrogen was added DIPEA (0.181 ml, 1.037 mmol) and the reaction left to stir for 5 minutes before the addition of acetic acid (1.5 ml). After stirring for a further 10 minutes, MP—CNBH$_3$ (0.665 g, 1.556 mmol) was added and the reaction left to stir at room temperature for 1.5 hours, then overnight. The MP—CNBH$_3$ was washed with dichloromethane and the combined washings and filtrate were concentrated in vacuo. The residue was taken up in the minimum volume of methanol and passed down a 5 g SCX column, eluting the product with 1% ammonia in methanol. The crude product was purified by column chromatography eluting with 3:2 ethyl acetate:isohexane (75 mg, 49%).

The following examples were prepared in a similar manner to Example 1.

Example 2

Cyclopentyl N-{4-[4-carbamoyl-5-(carbamoylamino)-2-thienyl]benzyl}-L-leucinate

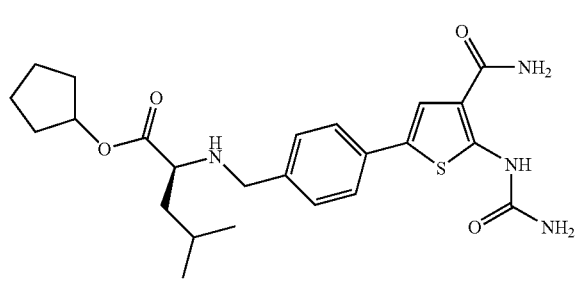

From Intermediate 2 and Intermediate 3a.

LC/MS purity 99%, m/z 473 [M+H]+. $^1$H NMR (400 MHz, DMSO-$d_6$), δ: 10.9 (1H, s), 7.7 (1H, s), 7.62 (2H, br s), 7.46 (2H, d, J=8.3 Hz), 7.25 (2H, d, J=8.3 Hz), 7.0 (2H, br s), 5.1 (1H, m), 3.72 (1H, d, J=13.7 Hz), 3.53 (1H, d, J=12.9 Hz), 3.10 (1H, t, J=7.1 Hz), 1.80-1.71 (3H, m), 1.68-1.33 (8H, m), 0.81 (3H, d, J=8.7 Hz), 0.78 (3H, d, J=8.8 Hz).

Example 3

Cyclopentyl N-{-4-[4-carbamoyl-5-(carbamoylamino)-2-thienyl]benzyl}-L-phenylalaninate

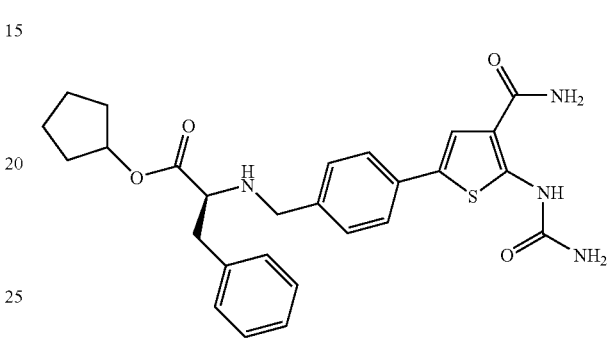

From Intermediate 2 and Intermediate 3d.

LC/MS purity 98%, m/z 507 [M+H]+. $^1$H NMR (400 MHz, DMSO-$d_6$), δ: 10.9 (1H, s), 7.7 (1H, s), 7.62 (2H, br s), 7.46 (2H, d, J=8.3 Hz), 7.25 (2H, d, J=8.3 Hz), 7.21 (5H, m), 7.0 (2H, br s), 5.0 (1H, m), 3.72 (1H, d, J=13.7 Hz), 3.58 (1H, d, J=12.9 Hz), 3.35 (1H, m), 2.90 (1H, dd, J=7.3 Hz), 2.79 (1H, dd, J=8.1 Hz), 1.80-1.71 (2H, m), 1.68-1.33 (6H, m).

Example 4

Cyclopentyl (2R)-({4-[4-carbamoyl-5-(carbamoylamino)-2-thienyl]benzyl}amino)(phenyl)acetate

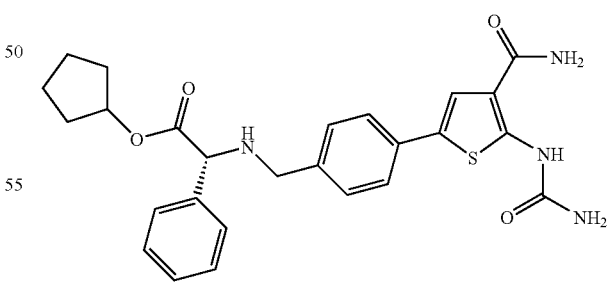

From Intermediate 2 and Intermediate 3c (R) isomer.

LC/MS purity 95%, m/z 493 [M+H]+. $^1$H NMR (400 MHz, DMSO-$d_6$), δ: 11.0 (1H, s), 7.8 (2H, d, J=8.4 Hz), 7.62 (2H, br s), 7.4 (2H, d, J=8.7 Hz), 7.5-7.3 (7H, m), 7.0 (2H, br s), 5.15 (1H, m), 4.43 (1H, s), 3.7 (2H, s), 3.1 (1H, s), 1.9-1.4 (8H, m).

Example 5

Cyclopentyl (2S)-({4-[4-carbamoyl-5-(carbamoylamino)-2-thienyl]benzyl}amino)(2-naphthyl)acetate

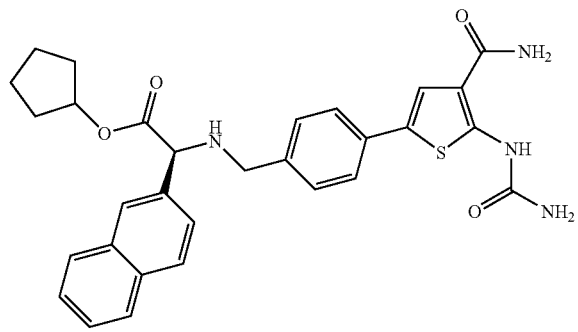

From Intermediate 2 and Intermediate 3b.
LC/MS purity 93%, m/z 543 [M+H]$^+$. $^1$H NMR (400 MHz, DMSO-d$_6$), δ: 11.0 (1H, s), 7.8 (4H, m), 7.69 (1H, s), 7.65 (2H, br s), 7.55-7.43 (5H, m), 7.3 (2H, d, J=13.4 Hz), 7.26 (1H, br s), 6.9 (2H, br s), 5.15 (1H, m), 4.43 (1H, s), 3.7 (2H, s), 3.1 (1H, s), 1.9-1.4 (8H, m).

Example 6

Cyclopentyl N-{4-[4-carbamoyl-5-(carbamoylamino)-2-thienyl]-3-chlorobenzyl}-L-leucinate

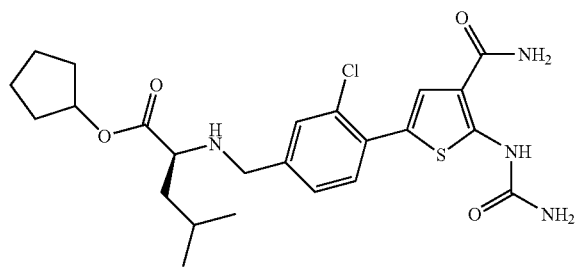

To a vial containing Intermediate 5a (62 mg, 0.138 mmol), Intermediate 1 (33.1 mg, 0.125 mmol) and tetrakis(triphenylphosphine)palladium (14.48 mg, 0.013 mmol) was added DME under N$_2$. The reaction mixture was stirred and 1 ml of an aqueous sodium bicarbonate solution added. The reaction vial was placed in a preheated oil bath at 80° C. After 2 hrs, analysis showed complete conversion to the desired product. Reaction mixture cooled to RT and poured into water, extracted into EtOAc and the combined organic extracts washed with water/brine before drying over magnesium sulphate. The product was purified by column chromatography eluting with 3-5% MeOH in DCM to give 37.5 mg, 0.072 mmol, 57.8% yield.
LCMS purity 98%: m/z 507/509 [M+H]$^+$. $^1$H NMR (400 MHz, DMSO-d$_6$), δ: 10.9 (1H, s), 7.7 (1H, s), 7.62 (2H, br s), 7.44 (2H, d, J=8.7 Hz), 7.29 (1H, s), 7.0 (2H, br s), 5.1 (1H, m), 3.72 (1H, d, J=13.7 Hz), 3.53 (2H, d, J=12.9 Hz), 3.10 (1H, t, J=7.1 Hz), 1.80-1.71 (2H, m), 1.68-1.33 (6H, m), 0.81 (3H, d, J=8.7 Hz), 0.78 (2H, d, J=8.8 Hz).

Example 7

Cyclopentyl N-{4-[4-carbamoyl-5-(carbamoylamino)-2-thienyl]-2-methylbenzyl}-L-leucinate

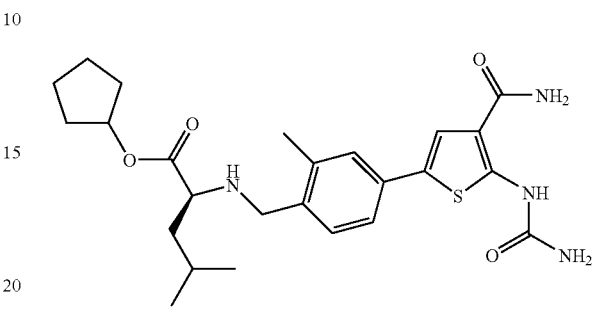

Synthesised via a similar procedure to Example 6 using Intermediate 5b. LCMS purity 99%, m/z 487 [M+H]$^+$. $^1$H NMR (400 MHz, DMSO), δ: 11.0 (1H, s), 7.7 (1H, s), 7.7 (1H, br s), 7.3 (3H, m), 7.2 (1H, d, J=7.7 Hz), 7.0 (2H, br s), 5.1 (1H, m), 3.7 (1H, d, J=13.1 Hz), 3.5 (1H, d, J=13.1 Hz), 3.1 (1H, br s), 3.0 (1H, br s), 2.3 (3H, s), 1.8 (2H, m), 1.6 (7H, m), 1.4 (2H, m), 0.9 (3H, d J=6.6 Hz), 0.8 (3H, d J=6.6 Hz).

Example 8

Cyclopentyl N-{3-[4-carbamoyl-5-(carbamoylamino)-2-thienyl]benzyl}-L-leucinate

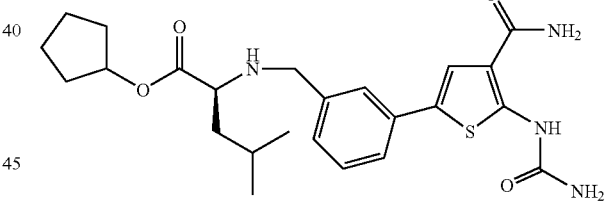

A vial containing tetrakis(triphenylphosphine)palladium (99 mg, 0.085 mmol), Intermediate 1 (22 mg, 0.854 mmol) and Intermediate 4a (313 mg, 0.939 mmol) was purged with N$_2$ and DME (dry, 12 ml) was added. To the mixture was added a saturated aqueous solution of sodium bicarbonate (2.5 ml) and the reaction mixture was heated to 90° C. in an oil bath for 4 hrs. The mixture was cooled to RT and poured into water (50 ml) and extracted with EtOAc (100 ml). The combined organic extracts were washed with brine, dried over magnesium sulphate and reduced to dryness under vacuum. The residue was purified by column chromatography eluting with 0-3% MeOH in DCM. The desired product (291 mg, 0.573 mmol, 67.1% yield) was isolated as a pale yellow solid.
LCMS purity 100%: m/z 473 [M+H]$^+$, 472 [M−H]$^-$. $^1$H NMR (400 MHz, DMSO-d$_6$), δ: 10.9 (1H, s), 7.7 (1H, s), 7.62 (2H, br s), 7.46 (1H, s), 7.25 (3H, m), 7.0 (2H, br s), 5.1 (1H, m), 3.72 (1H, d, J=13.7 Hz), 3.53 (2H, d, J=12.9 Hz), 3.10 (1H, t, J=7.1 Hz), 1.80-1.71 (2H, m), 1.68-1.33 (6H, m), 0.81 (3H, d, J=8.7 Hz), 0.78 (2H, d, J=8.8 Hz).

Examples 9-15

The following examples were synthesised in a similar manner to Example 8 using a variety of amino acid esters as detailed for Intermediates 4b-4-f.

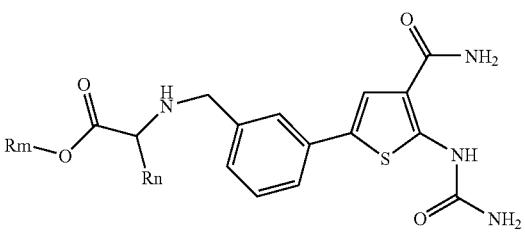

| Example Number | Intermediate used | $R_n$ | $R_m$ | Name | LCMS purity |
|---|---|---|---|---|---|
| 9 | 4b | (1-phenyl-1-methylethyl) | cyclopentyl | Cyclopentyl (2S)-({3-[4-carbamoyl-5-(carbamoylamino)-2-thienyl]benzyl}amino)(phenyl)acetate | 91% purity: m/z 493 [M + H]⁺ |
| 10 | 4c | (1-cyclohexyl-1-methylethyl) | cyclopentyl | Cyclopentyl (2S)-({3-[4-carbamoyl-5-(carbamoylamino)-2-thienyl]benzyl}amino)(cyclohexyl)acetate | 97% purity: m/z 499 [M + H]⁺ |
| 11 | 4d | (tert-butoxymethyl) | cyclopentyl | Cyclopentyl O-tert-butyl-N-{3-[4-carbamoyl-5-(carbamoylamino)thiophen-2-yl]benzyl}-L-serinate | 98% purity: m/z 503 [M + H]⁺ |
| 12* | Example 11 | (hydroxymethyl) | cyclopentyl | Cyclopentyl N-{3-[4-carbamoyl-5-(carbamoylamino)thiophen-2-yl]benzyl}-L-serinate | 98% purity: m/z 447 [M + H]⁺ |
| 13 | 4e | (1-hydroxyethyl) | cyclopentyl | Cyclopentyl N-{3-[4-carbamoyl-5-(carbamoylamino)thiophen-2-yl]benzyl}-L-threoninate | 97% purity: m/z 461 [M + H]⁺ |
| 14 | tert-butyl-L-leucinate | isobutyl | tbutyl | tert-Butyl N-{3-[4-carbamoyl-5-(carbamoylamino)-2-thienyl]benzyl}-L-leucinate | 96% purity: m/z 461 [M + H]⁺ |

-continued

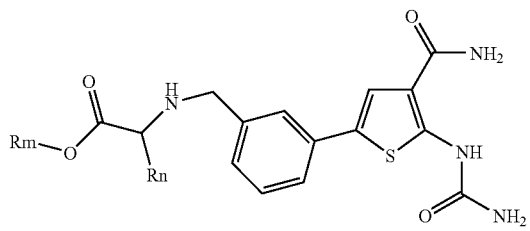

| Example Number | Intermediate used | $R_n$ | $R_m$ | Name | LCMS purity |
|---|---|---|---|---|---|
| 15 | 4f | ![tBu] | cyclopentyl | Cyclopentyl N-{3-[4-carbamoyl-5-(carbamoylamino)thiophen-2-yl]benzyl}-L-valinate | 96% purity: m/z 459.5 [M + H]+ |

*Example 12 was prepared from Example 11 using the experimental procedure shown below.

To a solution of Example 11 (40 mg, 0.080 mmol) in DCM (2 ml) was added trifluoroacetic acid (0.4 ml). The reaction mixture was left to stir overnight at RT. The solvent was removed in vacuo and to the residue was added methanol and 2 drops of acetic acid. The solution was loaded onto an SCX column and the product eluted with 1% ammonia in methanol. The ammonia fraction was concentrated in vacuo to afford an oil to which was added DCM and isohexane. A solid was obtained and collected by filtration (22 mg, 55% yield).

$^1$H NMR (400 MHz, DMSO-$d_6$), δ: 11.0 (1H, s), 7.7 (1H, s), 7.7 (1H, br s), 7.4 (1H, s), 7.4 (1H, d), 7.3 (2H, m), 7.1 (1H, d), 6.9 (2H, br s), 5.1 (1H, m), 4.8 (1H, br s), 3.8 (1H, d), 3.6 (3H, m), 3.2 (1H, br s), 1.8 (2H, m), 1.6-1.4 (6H, m).

Example 16

Cyclopentyl N-(2-{4-[4-carbamoyl-5-(carbamoylamino)-2-thienyl]phenyl}ethyl)-L-leucinate

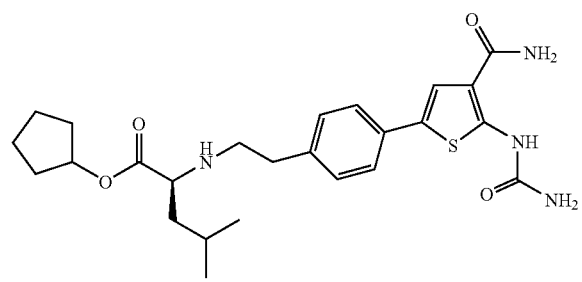

A vial charged with Intermediate 6a (153 mg, 0.356 mmol), Intermediate 1 (86 mg, 0.324 mmol) and Pd(PPh$_3$)$_4$ (37.4 mg, 0.032 mmol) was purged with nitrogen. DME (6 ml, dry) was added along with NaHCO$_3$ (1.0 ml, saturated aqueous solution) and the reaction heated at 80° C. for 3 hr. The reaction mixture was cooled to RT and poured into water (50 ml). Extraction of the product with EtOAc (2×40 ml) was followed by the washing of the organic layers with water (50 ml) and brine (50 ml) and drying over magnesium sulphate. Removal of the solvent under reduced pressure gave a brown oily solid that was contaminated with triphenylphosphine oxide. Purification by capture and release on SCX (eluting with MeOH) gave 53 mg of an orange oil that was only 70% pure. The product was purified by column chromatography eluting with EtOAc 50% in hexanes to give 42 mg (27%) of a pale orange powder.

LCMS purity 96%: m/z 487 [M+H]+; 485 [M−H]−. $^1$H NMR (400 MHz, DMSO-$d_6$), δ: 10.9 (1H, s), 7.8 (2H, s), 7.44 (2H, d, J=8.7 Hz), 7.29 (1H, s), 7.23 (2H, d, J=8.7 Hz), 6.9 (2H, br s), 5.1 (1H, m), 3.10 (1H, t, J=7.1 Hz), 2.6-2.79 (4H, m), 1.80-1.71 (3H, m), 1.68-1.33 (7H, m), 1.32 (1H, m), 0.81 (3H, d, J=8.7 Hz), 0.78 (2H, d, J=8.8 Hz).

Example 17

Cyclopentyl N-(2-{4-[4-carbamoyl-5-(carbamoylamino)-2-thienyl]-3-chlorophenyl}ethyl)-L-leucinate

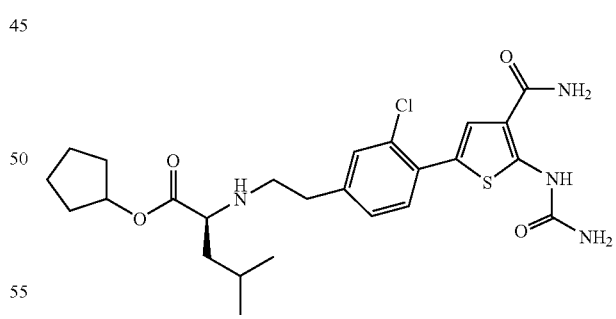

Synthesised via a similar procedure to Example 16 using Intermediate 6b.

LCMS purity 98%: m/z 522 [M+H]+. $^1$H NMR (400 MHz, DMSO-$d_6$), δ: 10.9 (1H, s), 7.8 (2H, s), 7.42 (1H, s), 7.29 (1H, s), 7.23 (2H, d, J=8.7 Hz), 6.9 (2H, br s), 5.1 (1H, m), 3.10 (1H, t, J=7.1 Hz), 2.6-2.79 (4H, m), 1.80-1.71 (3H, m), 1.68-1.33 (7H, m), 1.32 (1H, m), 0.81 (3H, d, J=8.7 Hz), 0.78 (2H, d, J=8.8 Hz).

Example 18

Cyclopentyl N-(2-{3-[4-carbamoyl-5-(carbamoylamino)-2-thienyl]phenyl}ethyl)-L-leucinate

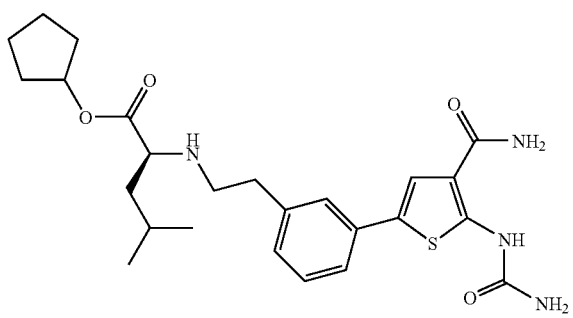

Synthesised via a similar procedure to Example 16 using Intermediate 6c.

LCMS purity 99%, m/z 487 [M+H]$^+$. $^1$H NMR (400 MHz, DMSO-d$_6$), δ: 11.0 (1H, s), 7.7 (1H, s), 7.7 (1H, br s), 7.3 (4H, m), 7.1 (1H, d, J=7.4 Hz), 7.0 (2H, br s), 5.1 (1H, m), 3.2 (1H, br s), 3.0 (1H, br s), 2.7 (4H, m), 1.8 (2H, m), 1.6 (7H, m), 1.3 (2H, m), 0.9 (3H, d J=6.6 Hz), 0.8 (3H, d J=6.6 Hz).

The following examples were synthesised in a similar manner to Example 18 using a variety of amino acid esters as detailed for Intermediate 6d-6f.

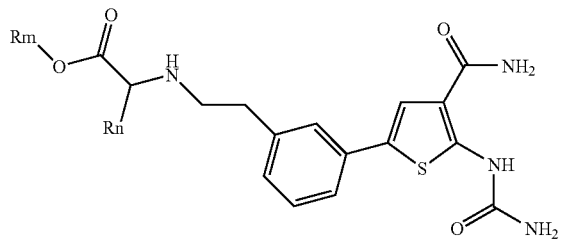

| Example Number | Intermediate used | R$_n$ | R$_m$ | Name | LCMS purity |
|---|---|---|---|---|---|
| 19 | 6d | (phenyl) | cyclopentyl | Cyclopentyl (2S)-[(2-{3-[4-carbamoyl-5-(carbamoylamino)-2-thienyl]phenyl}ethyl)amino](phenyl)acetate | 98% purity: m/z 507 [M + H]$^+$ |
| 20 | 6e | (CH$_2$-O-tBu) | cyclopentyl | Cyclopentyl O-tert-butyl-N-(2-{3-[4-carbamoyl-5-(carbamoylamino)-2-thienyl]phenyl}ethyl)-L-serinate | 95% purity: m/z 517 [M + H]$^+$ |
| 21 | 6f | (CH(CH$_3$)-O-tBu) | cyclopentyl | Cyclopentyl O-tert-butyl-N-(2-{3-[4-carbamoyl-5-(carbamoylamino)-2-thienyl]phenyl}ethyl)-L-threoninate | 96% purity: m/z 531 [M + H]$^+$ |

Example 22

Cyclopentyl N-(2-{5-[4-carbamoyl-5-(carbamoylamino)thiophen-2-yl]-2-fluorophenyl}ethyl)-L-leucinate

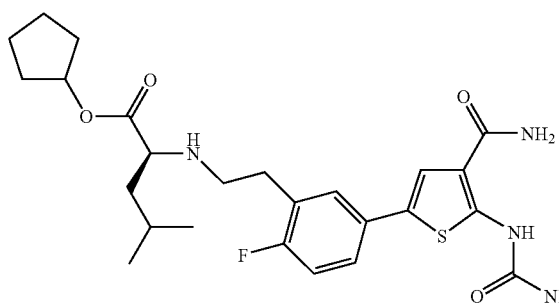

Synthesised via a similar procedure to Example 16 using Intermediate 11a.

LCMS purity 100%, m/z 505 [M+H]+, 1H NMR (400 MHz, DMSO-d6), δ: 11.0 (1H, s), 7.6 (2H, br s), 7.4 (1H, m), 7.3 (1H, m), 7.3 (1H, m), 7.1 (1H, t), 6.9 (2H, br s), 5.0 (1H, m), 3.1 (1H, s), 2.7-2.5 (4H, m), 1.9 (1H, br s), 1.7 (2H, m), 1.6-1.4 (7H, m), 0.8 (3H, d), 0.8 (3H, d).

Example 23

Cyclopentyl N-(2-{5-[4-carbamoyl-5-(carbamoylamino)thiophen-2-yl]-2-methylphenyl}ethyl)-L-leucinate

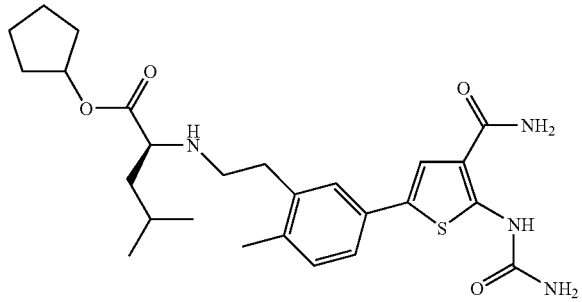

Synthesised via a similar procedure to Example 16 using Intermediate 11b.

LCMS purity 97%, m/z 499.4 [M−H]−, 1H NMR (400 MHz, DMSO-d6), ε: 11.0 (1H, s), 7.7 (2H, br s), 7.3 (2H, br s), 7.2 (1H, d), 7.1 (1H, d), 7.0 (2H, br s), 5.1 (1H, m), 3.2 (1H, m), 2.7 (4H, m), 2.2 (3H, s), 1.9 (1H, m), 1.8 (2H, m), 1.6 (7H, m), 1.4 (2H, m), 0.9 (3H, d), 0.8 (3H, d).

Example 24

Cyclopentyl N-(2-{5-[4-carbamoyl-5-(carbamoylamino)thiophen-2-yl]-2-chlorophenyl}ethyl)-L-leucinate

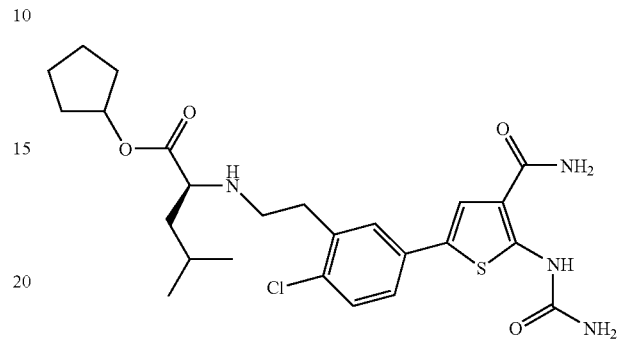

Synthesised via a similar procedure to Example 16 using Intermediate 11c.

LCMS purify 96%, m/z 519.5 [M−H]−, 1H NMR (400 MHz, DMSO-d6), δ: 11.0 (1H, s), 7.7 (1H, s), 7.7 (1H, br s), 7.5 (1H, d), 7.4 (1H, d), 7.4 (1H, dd), 7.3 (1H, br s), 7.0 (2H, br s), 5.1 (1H, M), 3.2 (1H, m), 2.8 (3H, m), 2.6 (1H, m), 2.0 (1H, br s), 1.8 (2H, m), 1.6 (7H, m), 1.3 (2H, m), 0.9 (3H, d), 0.8 (2H, m), 0.9 (3H, d).

Example 25

Cyclopentyl N-(3-{4-[4-carbamoyl-5-(carbamoylamino)-2-thienyl]phenoxy}propyl)-L-leucinate

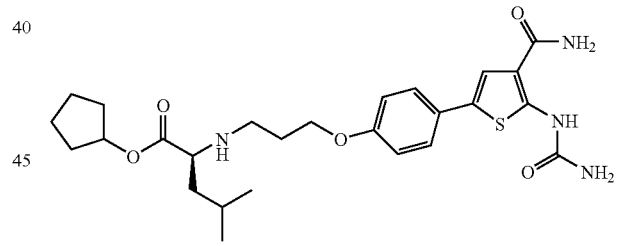

To a mixture of Intermediate 7a (0.2 g, 0.435 mmol), Intermediate 1 (0.126 g, 0.479 mmol) and Pd(PPh3)4 (0.050 g, 0.044 mmol) was added DME (5 ml) followed by 2 ml of a saturated solution of NaHCO3. The mixture was purged with nitrogen and placed in a pre-heated oil bath at 80° C. Upon stirring at this temperature for 3 hrs the reaction was judged to be complete by LC-MS. The mixture was cooled to RT, diluted with MeOH and absorbed onto silica. The residue was subjected to column chromatography eluting with 3 to 4% MeOH in DCM. The material was then subjected to SCX capture and release. Yield=0.11 g, 0.213 mmol, 48.9% yield. LCMS purity 100%: m/z 517 (M+H)+; 515 (M−H)−. 1H NMR (400 MHz, DMSO-d6), δ: 10.91 (1H, s), 7.61 (1H, br s), 7.52 (1H, s), 7.38 (2H, d, J=8.8 Hz), 7.24 (1H, br s), 6.90 (3H, d, J=8.8 Hz), 5.05 (1H, t, J=5.9 Hz), 3.98 (2H, t, J=6.4 Hz), 3.07 (1H, br s), 2.61 (1H, t, J=6.6 Hz), 1.70-1.83 (4H, m), 1.49-1.61 (6H, m), 1.32 (2H, t, J=7.1 Hz), 0.81 (6H, dd, J=12.0, 6.6 Hz).

Example 26

Cyclopentyl N-(3-{4-[4-carbamoyl-5-(carbamoylamino)-2-thienyl]-3-chlorophenoxy}propyl)-L-leucinate

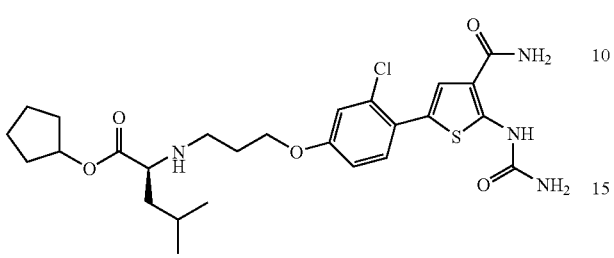

Synthesised via a similar procedure to Example 25 using Intermediate 7b.

LCMS purity 98%: m/z 552 (M+H)$^+$. $^1$H NMR (400 MHz, DMSO-d$_6$), δ: 10.98 (1H, s), 7.61 (1H, br s), 7.49 (1H, s), 7.41 (1H, d, J=8.8 Hz), 7.27 (1H, br s), 7.07 (1H, m), 6.9 (2H, m), 5.08 (1H, m), 4.07 (2H, m), 3.05 (1H, m), 2.6 (1H, m), 1.8 (4H, m), 1.60-1.49 (7H, m), 1.3 (2H, m), 0.81 (3H, d, J=8.4 Hz), 0.79 (3H, d, J=8.7 Hz).

Example 27

Cyclopentyl N-(5-{4-[4-carbamoyl-5-(carbamoylamino)-2-thienyl]phenoxy}pentyl)-L-leucinate

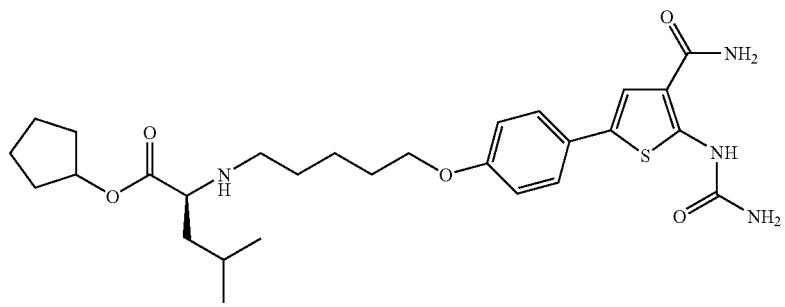

To a mixture of Intermediate 8a (600 mg, 1.231 mmol), Intermediate 1 (361 mg, 1.231 mmol) and Pd(PPh$_3$)$_4$ (142 mg, 0.123 mmol) was added DME (8 ml). After the addition of a saturated solution of NaHCO$_3$ (3 ml), the mixture was purged with nitrogen and placed in a preheated oil bath at 80° C. After 4 hrs the reaction was judged to be complete by LCMS. The mixture was diluted with MeOH, absorbed onto silica and subjected to column chromatography eluting with 3 to 5% MeOH in DCM. The product was isolated after evaporation (0.305 g, 0.543 mmol, 44.1% yield).

LCMS purity 100%: m/z 545 (M+H)$^+$. $^1$H NMR (400 MHz, DMSO-d$_6$), δ: 10.91 (1H, s), 7.60 (1H, br s), 7.52 (1H, s), 7.38 (2H, d, J=8.8 Hz), 7.23 (1H, br s), 6.91 (3H, m), 5.05 (1H, t, J=6.1 Hz), 3.92 (2H, t, J=6.4 Hz), 3.06 (1H, m), 2.34 (1H, m), 1.72-1.80 (2H, m), 1.65 (3H, dd, J=10.5, 6.1 Hz), 1.55 (3H, dd, J=10.5, 7 Hz), 1.50-1.61 (3H, m), 1.38 (4H, d, J=2.9 Hz), 1.30 (3H, t, J=7.3 Hz), 0.81 (6H, dd, J=11.0, 6.6 Hz).

Example 28

Cyclopentyl N-(5-{4-[4-carbamoyl-5-(carbamoylamino)-2-thienyl]-3-chlorophenoxy}pentyl)-L-leucinate

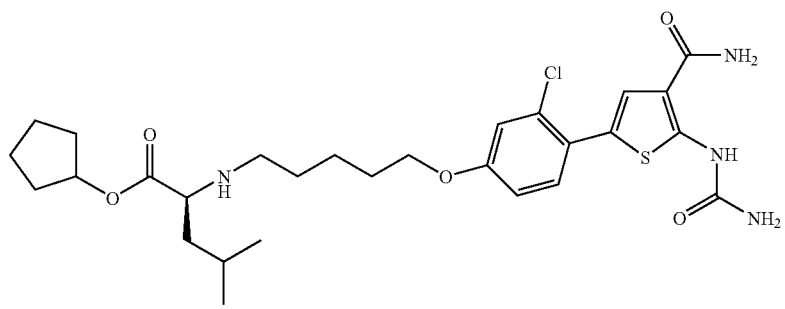

Synthesised via a similar procedure to Example 27 using Intermediate 8b.

LCMS purity 98%: m/z 580 (M+H)+. $^1$H NMR (400 MHz, DMSO-$d_6$), δ: 10.97 (1H, s), 7.69 (1 h, br s), 7.45 (1H, s), 7.4 (1H, d, J=13 Hz), 7.23 (1H, br s), 7.05 (1H, d, J=8.5 Hz), 6.9 (3H, m), 5.1 (1H, m), 4.0 (2H, m), 3.05 (1H, m), 2.3 (1H, m), 1.75 (2H, m), 1.69-1.45 (9H, m), 1.44-1.22 (6H, m), 0.81 (3H, d, J=8.4 Hz), 0.79 (3H, d, J=8.7 Hz).

Example 29

Cyclopentyl N-[(2E)-3-{4-[4-carbamoyl-5-(carbamoylamino)-2-thienyl]phenyl}Prop-2-en-1-yl]-L-leucinate

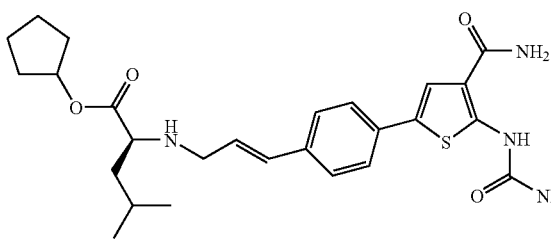

Synthesised via a similar procedure to Example 27 using Intermediate 9a.

To a solution of cyclopentyl N-(tert-butoxycarbonyl)-N-[(2E)-3-{-4-[4-carbamoyl-5-(carbamoylamino)thiophen-2-yl]phenyl}prop-2-en-1-yl]-leucinate (Intermediate 9a) (39 mg, 0.065 mmol) in dichloromethane (1 ml) was added trifluoroacetic acid (0.5 ml). The reaction mixture was left to stir at RT for 2 hrs. The reaction mixture was worked up by removal of the solvents in vacuo. The residue was diluted with methanol and captured by SCX chromatography, eluting the product with ammonia in methanol. The ammonia fractions were concentrated in vacuo to afford an oily residue. This was taken up in dichloromethane and isohexane added. After removal of the solvent in vacuo a pale orange solid was obtained (24.3 mg, 0.049 mmol, 75%).

LCMS purity 100%, m/z 499.0 [M+H]+, $^1$H NMR (400 MHz, DMSO-$d_6$), δ: 11.0 (1H, s), 7.7 (1H, s), 7.6 (1H, br s), 7.4 (2H, d, J=8.3 Hz), 7.3 (2H, d, J=8.8 Hz), 7.2 (1H, br s), 6.9 (2H, br s), 6.4 (1H, d, J=15.7 Hz), 6.2 (1H, m), 5.0 (1H, m), 3.3 (1H, H), 3.2 (2H, m), 1.8-1.7 (2H, m), 1.6-1.5 (7H, m), 1.3 (2H, m), 0.8 (6H, m).

Examples 30-40

The following examples were synthesised in a similar manner to Example 29 using a variety of commercially available mono and di-substituted 4-bromo-iodobenzenes as detailed for Intermediate 9a in Scheme 7.

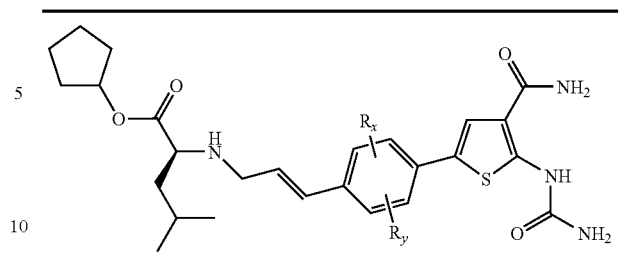

| Example Number | $R_x$ | $R_y$ | Name | LCMS purity |
|---|---|---|---|---|
| 30 | 2-methyl | H | Cyclopentyl N-[(2E)-3-{4-[4-carbamoyl-5-(carbamoylamino)thiophen-2-yl]-2-methylphenyl}prop-2-en-1-yl]-L-leucinate | 97% purity: m/z 511.2 [M − H]+ |
| 31 | 2-fluoro | H | Cyclopentyl N-[(2E)-3-{4-[4-carbamoyl-5-(carbamoylamino)thiophen-2-yl]-2-fluorophenyl}prop-2-en-1-yl]-L-leucinate | 98% purity: m/z 515.2 [M − H]+ |
| 32 | 2-chloro | H | Cyclopentyl N-[(2E)-3-{4-[4-carbamoyl-5-(carbamoylamino)thiophen-2-yl]-2-chlorophenyl}prop-2-en-1-yl]-L-leucinate | 99% purity: m/z 531 [M − H]+ |
| 33 | 3-methyl | H | Cyclopentyl N-[(2E)-3-{4-[4-carbamoyl-5-(carbamoylamino)thiophen-2-yl]-3-methylphenyl}prop-2-en-1-yl]-L-leucinate | 98% purity: m/z 531 [M + H]+ |
| 34 | 3-fluoro | H | Cyclopentyl N-[(2E)-3-{4-[4-carbamoyl-5-(carbamoylamino)thiophen-2-yl]-3-fluorophenyl}prop-2-en-1-yl]-L-leucinate | 94% purity: m/z 515.3 [M − H]+ |
| 35 | 3-chloro | H | Cyclopentyl N-[(2E)-3-{4-[4-carbamoyl-5-(carbamoylamino)thiophen-2-yl]-3-chlorophenyl}prop-2-en-1-yl]-L-leucinate | 96% purity: m/z 531.2 [M − H]+ |
| 36 | 2-CF$_3$ | H | Cyclopentyl N-[(2E)-3-{4-[4-carbamoyl-5-(carbamoylamino)thiophen-2-yl]-2-(trifluoromethyl)phenyl}prop-2-en-1-yl]-L-leucinate | 98% purity: m/z 565.4 [M − H]+ |
| 37 | 2-fluoro | 5-fluoro | Cyclopentyl N-[(2E)-3-{4-[4-carbamoyl-5-(carbamoylamino)thiophen-2-yl]-2,5-difluorophenyl}prop-2-en-1-yl]-L-leucinate | 98% purity: m/z 533.4 [M − H]+ |
| 38 | 2-fluoro | 6-fluoro | Cyclopentyl N-[(2E)-3-{4-[4-carbamoyl-5-(carbamoylamino)thiophen-2-yl]-2,6-difluorophenyl}prop-2-en-1-yl]-L-leucinate | 100% purity: m/z 533.4 [M − H]+ |
| 39 | 3-CF$_3$ | H | Cyclopentyl N-[(2E)-3-{4-[4-carbamoyl-5-(carbamoylamino)thiophen-2-yl]-3-(trifluoromethyl)phenyl}prop-2-en-1-yl]-L-leucinate | 97% purity: m/z 565.4 [M − H]+ |
| 40 | 2-methyl | 6-methyl | Cyclopentyl N-[(2E)-3-{4-[4-carbamoyl-5-(carbamoylamino)thiophen-2-yl]-2,6-dimethylphenyl}prop-2-en-1-yl]-L-leucinate | 96% purity: m/z 525 [M − H]+ |

Examples 41-48

The following examples were synthesised in a similar manner to Example 27 using a variety of amino acid esters as detailed for Intermediates 9b-9h in Scheme 8.

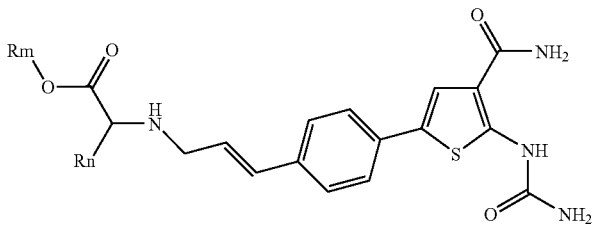

| Example Number | Intermediate used | $R_n$ | $R_m$ | Name | LCMS purity |
|---|---|---|---|---|---|
| 41 | 9c | (1-phenyl) | cyclopentyl | Cyclopentyl (2S)-{[(2E)-3-{4-[4-carbamoyl-5-(carbamoylamino)-2-thienyl]phenyl}prop-2-en-1-yl]amino}(phenyl)acetate | 97% purity: m/z 519 [M + H]⁺ |
| 42 | 9b | (isobutyl) | tbutyl | tert-Butyl N-[(2E)-3-{4-[4-carbamoyl-5-(carbamoylamino)-2-thienyl]phenyl}-prop-2-en-1-yl]-L-leucinate | 99% purity: m/z 487 [M + H]⁺ |
| 43 | 9e | (tert-butoxymethyl) | cyclopentyl | Cyclopentyl O-tert-butyl-N-[(2E)-3-{4-[4-carbamoyl-5-(carbamoylamino)thiophen-2-yl]phenyl}prop-2-en-1-yl]-L-serinate | 100% purity: m/z 529 [M + H]⁺ |
| 44 | 9d | (cyclohexyl) | cyclopentyl | Cyclopentyl (2S)-{[(2E)-3-{4-[4-carbamoyl-5-(carbamoylamino)thiophen-2-yl]phenyl}prop-2-en-1-yl]amino}(cyclohexyl)ethanoate | 99% purity: m/z 525 [M + H]⁺ |
| 45 | 9g | (cyclohexyl) | tbutyl | tert-butyl (2S)-{[(2E)-3-{4-[4-carbamoyl-5-(carbamoylamino)thiophen-2-yl]phenyl}prop-2-en-1-yl]amino}(cyclohexyl)ethanoate | 95% purity: m/z 511 [M − H]⁺ |
| 46 | 9f | (isobutyl, D-) | cyclopentyl | Cyclopentyl N-[(2E)-3-{4-[4-carbamoyl-5-(carbamoylamino)-2-thienyl]phenyl}prop-2-en-1-yl]-D-leucinate | 97% purity: m/z 497 [M − H]⁺ |

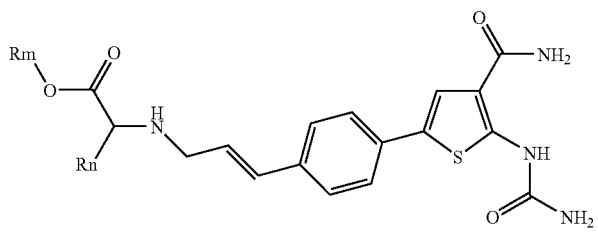

| Example Number | Intermediate used | $R_n$ | $R_m$ | Name | LCMS purity |
|---|---|---|---|---|---|
| 47 | 9h | ![structure with tBuO and H] | cyclopentyl | Cyclopentyl O-tert-butyl-N-[(2E)-3-{4-[4-carbamoyl-5-(carbamoylamino)thiophen-2-yl]phenyl}prop-2-en-1-yl]-L-threoninate | 97% purity: m/z 543 [M + H]$^+$ |
| 48 | Example 47 | ![structure with HO and H] | cyclopentyl | Cyclopentyl N-[(2E)-3-{4-[4-carbamoyl-5-(carbamoylamino)thiophen-2-yl]phenyl}prop-2-en-1-yl]-L-threoninate | 98% purity: m/z 485 [M − H]$^+$ |

Example 49

Cyclopentyl N-[(2E)-3-{3-[4-carbamoyl-5-(carbamoylamino)-2-thienyl]phenyl}prop-2-en-1-yl]-L-leucinate

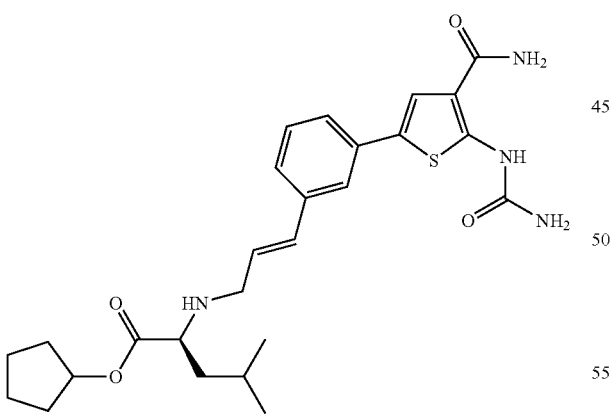

Synthesised via a similar procedure to Example 16 using Intermediate 10.

LCMS purity 98%, m/z 499.2 [M+H]$^+$, $^1$H NMR (400 MHz, DMSO-d$_5$), δ: 11.0 (1H, s), 7.7 (1H, s), 7.6 (1H, br s), 7.5 (1H, s), 7.3 (3H, m), 7.2 (1H, m), 6.9 (2H, br s), 6.5 (1H, d), 6.3 (1H, m), 5.0 (1H, m), 3.3 (1H, m), 3.2 (1H, m), 2.1 (1H, br s), 1.8 (2H, bm), 1.7-1.5 (7H, m), 1.4 (2H, m), 0.8 (6H, m).

NMR Data

| Example Number | NMR assignment |
|---|---|
| 9 | $^1$H NMR (400 MHz, DMSO-d$_6$), δ: 11.0 (1H, s), 7.7 (1H, s), 7.7 (1H, br s), 7.4 (1H, s), 7.4-7.2 (7H, m), 7.1 (1H, d), 6.9 (2H, br s), 5.0 (1H, m), 4.2 (1H, d), 3.6 (2H, bd), 3.0 (1H, m), 1.8-1.3 (8H, m). |
| 10 | $^1$H NMR (400 MHz, DMSO-d$_6$), δ: 11.0 (1H, s), 7.7 (1H, s), 7.7 (1H, br s), 7.4 (1H, s), 7.4 (1H, d), 7.3 (1H, t), 7.3 (1H, br s), 7.1 (1H, d), 6.9 (2H, br s), 5.0 (1H, m), 3.8 (1H, d), 3.5 (1H, d), 2.8 (1H, m), 2.3 (1H, m), 1.9-1.4 (12H, m), 1.2-0.9 (5H, m). |
| 11 | $^1$H NMR (400 MHz, DMSO-d$_6$), δ: 11.0 (1H, s), 7.7 (1H, s), 7.7 (1H, br s), 7.4 (1H, s), 7.4 (1H, d), 7.3 (2H, m), 7.1 (1H, d), 6.9 (2H, br s), 5.0 (1H, m), 3.8 (1H, d), 3.6 (1H, d), 3.4 (2H, m), 3.2 (1H, br s), 1.8 (2H, m), 1.7-1.5 (6H, m), 1.0 (9H, s). |
| 12 | $^1$H NMR (400 MHz, DMSO-d$_6$), δ: 11.0 (1H, s), 7.7 (1H, s), 7.7 (1H, br s), 7.4 (1H, s), 7.4 (1H, d), 7.3 (2H, m), 7.1 (1H, d), 6.9 (2H, br s), 5.1 (1H, m), 4.8 (1H, br s), 3.8 (1H, d), 3.6 (3H, m), 3.2 (1H, br s), 1.8 (2H, m), 1.6-1.4 (6H, m). |
| 13 | $^1$H NMR (400 MHz, DMSO-d$_6$), δ: 11.0 (1H, s), 7.7 (1H, s), 7.7 (1H, br s), 7.4 (1H, s), 7.4 (1H, d), 7.3 (2H, m), 7.1 (1H, d), 6.9 (2H, br s), 5.0 (1H, m), 4.8 (1H, br s), 3.8 (2H, m), 3.6 (1H, d), 2.9 (1H, br s), 1.8 (2H, m), 1.6-1.4 (6H, m), 1.1 (3H, d). |
| 14 | $^1$H NMR (400 MHz, DMSO-d$_6$), δ: 11.0 (1H, s), 7.7 (2H, s), 7.5 (1H, br s), 7.4 (1H, d, J = 7.8 Hz), 7.3 (2H, m), 7.2 (1H, d, J = 7.3 Hz), 7.0 (2H, br s), 3.8 (1H, d), 3.6 (1H, d), 3.0 (1H, t), 2.5 (2H, m), 1.8 (1H, septet), 1.4 (9H, s), 1.4 (1H, m), 0.9 (3H, d, J = 6.6 Hz), 0.8 (3H, d, J = 6.6 Hz). |
| 15 | $^1$H NMR (400 MHz, DMSO-d$_6$), δ: 11.0 (1H, s), 7.7 (2H, br s), 7.4 (1H, s), 7.3 (1H, d), 7.2 (1H, t), 7.1 (1H, d), 6.9 (2H, br s), 5.0 (1H, m), 3.7 (1H, d), 3.5 (1H, d), 2.8 (1H, br s), 2.3 (1H, br s), 1.8 (3H, m), 1.6-1.4 (6H, m), 0.8 (6H, m). |
| 19 | $^1$H NMR (400 MHz, DMSO-d$_6$), δ: 11.0 (1H, s), 7.7 (1H, s), 7.6 (1H, br s), 7.3-7.2 (8H, m), 7.0 (1H, d), 7.0 (2H, br s), 5.0 (1H, m), 4.3 (1H, s), 2.8-2.6 (4H, m), 1.8-1.6 (2H, m), 1.6-1.2 (6H, m). |
| 20 | $^1$H NMR (400 MHz, DMSO-d$_6$), δ: 11.0 (1H, s), 7.7 (1H, s), 7.7 (1H, br s), 7.3 (4H, m), 7.0 (1H, d), 6.9 (2H, br s), 5.0 (1H, m), 3.4 (1H, m), 3.3 (1H, m), 3.2 (1H, br s), 2.8 (1H, m), 2.6 (3H, m), 1.8 (1H, br s), 1.7 (2H, m), 1.6-1.4 (6H, m), 1.0 (9H, s). |
| 21 | $^1$H NMR (400 MHz, DMSO-d$_6$), δ: 11.0 (1H, s), 7.7 (1H, s), 7.6 (1H, br s), 7.3 (4H, m), 7.0 (1H, d), 6.9 (2H, br s), 5.0 (1H, m), 3.8 (1H, m), 3.0 (1H, br s), 2.7 (1H, m), 2.6 (2H, m), 2.5 (1H, m), 1.8 (2H, m), 1.6-1.4 (6H, m), 1.1 (3H, d), 1.0 (9H, s). |
| 30 | $^1$H NMR (400 MHz, DMSO-d$_6$), δ: 11.0 (1H, s), 7.7 (1H, s), 7.7 (1H, br s), 7.5 (1H, d), 7.3 (1H, d), 7.3 (2H, br s), 7.0 (2H, br s), 6.7 (1H, d), 6.1 (1H, m), 5.1 (1H, m), 3.4 (1H, m), 3.2 (2H, m), 3.0 (1H, br s), 2.3 (3H, s), 1.8 (2H, m), 1.6 (7H, m), 1.4 (2H, m), 0.9 (3H, d), 0.8 (3H, d). |
| 31 | $^1$H NMR (400 MHz, DMSO-d$_6$), δ: 11.0 (1H, s), 7.8 (1H, s), 7.7 (1H, br s), 7.6 (1H, m), 7.4 (2H, br s), 7.3 (1H, m), 7.0 (2H, br s), 6.6 (1H, d, J = 16.1 Hz), 6.4 (1H, m), 5.1 (1H, m), 3.4 (1H, m), 3.2 (2H, m), 2.2 (1H, br s), 1.8 (2H, m), 1.6 (7H, m), 1.4 (2H, m), 0.9 (3H, d), 0.8 (3H, d). |
| 32 | $^1$H NMR (400 MHz, DMSO-d$_6$), δ: 11.0 (1H, s), 7.8 (1H, s), 7.7 (1H, d), 7.7 (1H, br s), 7.5 (1H, d), 7.4 (1H, dd), 7.4 (1H, br s), 7.0 (2H, br s), 6.8 (1H, d), 6.3 (1H, m), 5.1 (1H, m), 3.4 (1H, m), 3.2 (2H, m), 2.2 (1H, br s), 1.8 (2H, m), 1.6 (7H, m), 1.4 (2H, m), 0.9 (3H, d), 0.8 (3H, d). |
| 34 | $^1$H NMR (400 MHz, DMSO-d$_6$), δ: 11.1 (1H, s), 7.8 (1H, s), 7.8 (1H, br s), 7.6 (1H, m), 7.3 (3H, m), 7.0 (2H, br s), 6.5 (1H, d), 6.4 (1H, m), 5.1 (1H, m), 3.4 (1H, m), 3.2 (2H, m), 2.1 (1H, br s), 1.8 (2H, m), 1.6 (7H, m), 1.4 (2H, m), 0.9 (3H, d), 0.8 (3H, d). |
| 35 | $^1$H NMR (400 MHz, DMSO-d$_6$), δ: 11.0 (1H, s), 7.8 (1H, br s), 7.7 (1H, s), 7.5 (2H, m), 7.4 (1H, d), 7.3 (1H, br s), 7.0 (2H, br s), 6.5 (1H, d), 6.4 (1H, m), 5.1 (1H, m), 3.4 (1H, m), 3.2 (2H, m), 2.1 (1H, br s), 1.8 (2H, m), 1.6 (7H, m), 1.4 (2H, m), 0.9 (3H, d), 0.8 (3H, d). |
| 36 | $^1$H NMR (400 MHz, DMSO-d$_6$), δ: 11.0 (1H, s), 7.9 (1H, s), 7.8 (1H, d), 7.8 (1H, s), 7.7 (1H, br s), 7.7 (1H, d), 7.4 (1H, br s), 7.0 (2H, br s), 6.7 (1H, d), 6.4 (1H, m), 5.1 (1H, m), 3.4 (1H, m), 3.2 (2H, m), 2.1 (1H, br s), 1.8 (2H, m), 1.6 (7H, m), 1.4 (2H, m), 0.9 (3H, d), 0.8 (3H, d). |
| 37 | $^1$H NMR (400 MHz, DMSO-d$_6$), δ: 11.1 (1H, s), 7.9 (1H, s), 7.7 (1H, br s), 7.6 (1H, dd), 7.4 (1H, dd), 7.4 (1H, br s), 7.0 (2H, br s), 6.6 (1H, d), 6.5 (1H, m), 5.1 (1H, m), 3.4 (1H, m), 3.2 (2H, m), 2.1 (1H, br s), 1.8 (2H, m), 1.6 (7H, m), 1.4 (2H, m), 0.9 (3H, d), 0.8 (3H, d). |

| Example Number | NMR assignment |
|---|---|
| 38 | ¹H NMR (400 MHz, DMSO-d₆), δ: 11.0 (1H, s), 7.9 (1H, s), 7.6 (1H, br s), 7.4 (1H, br s), 7.2 (2H, m), 7.1 (1H, br s), 7.0 (1H br s), 6.5 (2H, m), 5.1 (1H, m), 3.4 (1H, m), 3.2 (2H, m), 2.2 (1H, br s), 1.8 (2H, m), 1.6 (7H, m), 1.4 (2H, m), 0.9 (3H, d), 0.8 (3H, d). |
| 39 | ¹H NMR (400 MHz, DMSO-d₆), δ: 11.0 (1H, s), 7.8 (1H, s), 7.7 (1H, br s) 7.7 (1H, d), 7.5 (1H, d), 7.3 (1H, s), 7.3 (1H, br s), 7.0 (2H, br s), 6.6 (1H, d), 6.5 (1H, m), 5.1 (1H, m), 3.4 (1H, m), 3.2 (2H, m), 2.2 (1H, br s), 1.8 (2H, m), 1.6 (7H, m), 1.4 (2H, m), 0.9 (3H, d), 0.8 (3H, d). |
| 40 | ¹H NMR (400 MHz, DMSO-d₆), δ: 11.0 (1H, s), 7.7 (2H, br s), 7.3 (1H, br s), 7.2 (2H, s), 7.0 (2H, br s), 6.4 (1H, d), 5.7 (1H, m), 5.1 (1H, m), 3.4 (1H, m), 3.2 (2H, m), 2.3 (6H, s), 2.2 (1H, br s), 1.8 (2H, m), 1.6 (7H, m), 1.4 (2H, m), 0.9 (3H, d), 0.8 (3H, d). |
| 41 | ¹H NMR (400 MHz, DMSO-d₆), δ: 11.0 (1H, s), 7.7 (1H, s), 7.7 (1H, br s), 7.5-7.3 (10H, m), 7.0 (2H, br s), 6.5 (1H, d), 6.3 (1H, m), 5.07 (1H, m), 4.3 (1H, m), 3.3 (2H, br s), 1.8-1.4 (8H, m). |
| 43 | ¹H NMR (400 MHz, DMSO-d₆), δ: 11.0 (1H, s), 7.7 (1H, s), 7.6 (1H, br s), 7.5 (2H, d), 7.4 (2H, d), 7.3 (1H, br s), 7.0 (2H, br s), 6.5 (1H, d), 6.3 (1H, m), 5.1 (1H, m), 3.5 (1H, m), 3.4 (1H, m), 3.3 (1H, m), 3.2 (2H, m), 1.8-1.50 (8H, m), 1.09 (9H, s). |
| 44 | ¹H NMR (400 MHz, DMSO-d₆), δ: 11.0 (1H, s), 7.8 (1H, s), 7.7 (1H, br s), 7.5 (2H, d), 7.4 (2H, d), 7.3 (1H, br s), 7.0 (2H, br s), 6.5 (1H, d), 6.3 (1H, m), 5.1 (1H, m), 3.2 (1H, m), 2.9 (2H, br s), 1.9-1.5 (13H, m), 1.2-0.9 (6H, m). |
| 45 | ¹H NMR (400 MHz, DMSO-d₆), δ: 11.0 (1H, s), 7.3 (1H, s), 7.7 (1H, br s), 7.5 (2H, d), 7.4 (2H, d), 7.32 (1H, br s), 7.0 (2H, br s), 6.5 (1H, d), 6.2 (1H, m), 3.4 (1H, m), 3.2 (1H, m), 2.8 (1H, br s), 1.9 (1H, br s), 1.8-1.5 (10H, m), 1.4 (9H, s). |
| 46 | ¹H NMR (400 MHz, DMSO-d₆), δ: 11.0 (1H, s), 7.7 (1H, s), 7.6 (1H, br s), 7.5 (2H, d), 7.4 (2H, d), 7.3 (1H, br s), 7.0 (2H, br s), 6.5 (1H, d), 6.25 (1H, m), 5.1 (1H, m), 3.3 (1H, m), 3.2 (2H, m), 1.7 (1H, sep), 1.87-1.5 (8H, m), 1.4 (2H, m), 0.9 (3H, d), 0.8 (3H, d). |
| 47 | ¹H NMR (400 MHz, DMSO-d₆), δ: 11.0 (1H, s), 7.7 (1H, s), 7.6 (1H, br s), 7.5 (2H, d), 7.4 (2H, d), 7.32 (1H, br s), 7.0 (2H, br s), 6.5 (1H, d), 6.3 (1H, m), 5.1 (1H, m), 3.9 (1H, m), 3.3 (1H, m), 3.2 (1H, m), 3.1 (1H, br s), 1.8-1.5 (8H, m), 1.1 (3H, d), 1.09 (9H, s). |
| 48 | ¹H NMR (400 MHz, DMSO-d₆), δ: 11.0 (1H, s), 7.7 (1H, s), 7.6 (1H, br s), 7.5 (2H, d), 7.4 (2H, d), 7.3 (1H, br s), 7.0 (2H, br s), 6.5 (1H, d), 6.27 (1H, m), 5.1 (1H, m), 4.7 (1H, br s), 3.8 (1H, m), 3.4 (1H, m), 3.2 (1H, m), 3.0 (1H, m), 1.8-1.5 (8H, m), 1.1 (3H, d). |

Example 50

(2S)-({4-[4-carbamoyl-5-(carbamoylamino)-2-thienyl]benzyl}amino)(phenyl)acetic acid

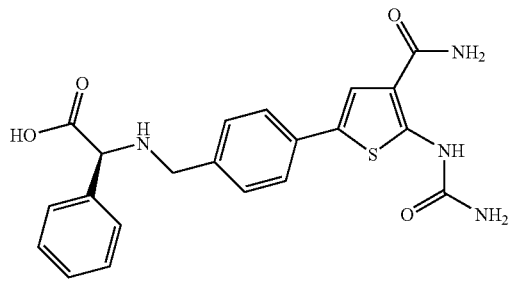

LC/MS purity 96%, m/z 425 [M+H]⁺, ¹H NMR (400 MHz, DMSO-d₆), δ: 11.0 (1H, br s), 7.7 (1H, s), 7.6 (1H, br s), 7.5 (2H, m), 7.4-7.3 (8H, m), 6.9 (2H, m), 4.2 (1H, s), 3.7 (2H, q, J=13.9 and 6.6 Hz).

To a solution of cyclopentyl (2S)-({-4-[4-carbamoyl-(carbamoylamino)-2-thienyl]benzyl}amino)(phenyl)acetate (Example 1) (50 mg, 102 μmol) in tetrahydrofuran (1 ml) was added 1.0M aq LiOH (0.508 ml, 508 μmol). The reaction was stirred at an oil bath temperature of 40° C. After 4 hours LCMS indicated 90% completion. The heating was removed and the reaction left to stir at room temperature overnight. The solvent was removed in vacuo and to the residue was added water (2 ml). 5 drops of acetic acid was added to the solution and a solid precipitated. The solid was collected by filtration and washed sequentially with water, ethanol and diethyl ether before drying under reduced pressure (26 mg, 60%).

The following examples were prepared in a similar manner to Example 50. Where necessary, the compounds were purified by preparative HPLC to achieve good purity.

Example 51

N-{4-[4-Carbamoyl-5-(carbamoylamino)-2-thienyl]benzyl}-L-leucine

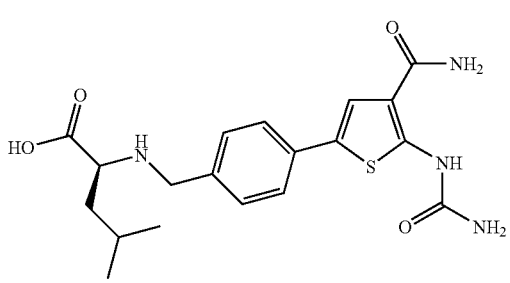

From Example 2. LC/MS purity 99%, m/z 405 [M+H]+.

Example 52

N-{-4-[4-Carbamoyl-5-(carbamoylamino)-2-thienyl]benzyl}-L-phenylalanine

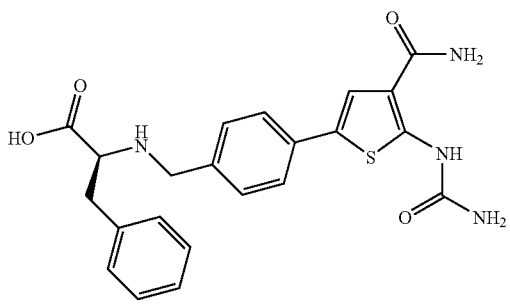

From Example 3. LC/MS purity 98%, m/z 439 [M+H]+.

Example 53

(2R)-({-4-[4-Carbamoyl-5-(carbamoylamino)-2-thienyl]benzyl}amino)(phenyl)acetic acid

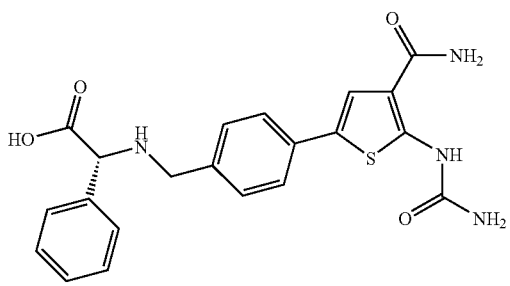

From Example 4. LC/MS purity 95%, m/z 425 [M+H]+.

Example 54

(2S)-({-4-[4-Carbamoyl-5-(carbamoylamino)-2-thienyl]benzyl}amino)(2-naphthyl)acetic acid

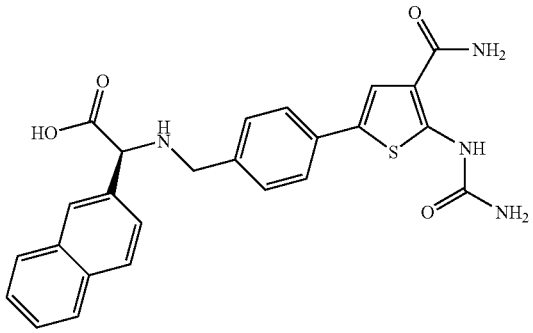

From Example 5. LC/MS purity 98%, m/z 475 [M+H]+.

Example 55

N{4-[4-carbamoyl-5-(carbamoylamino)-2-thienyl]-3-chlorobenzyl}-L-leucine

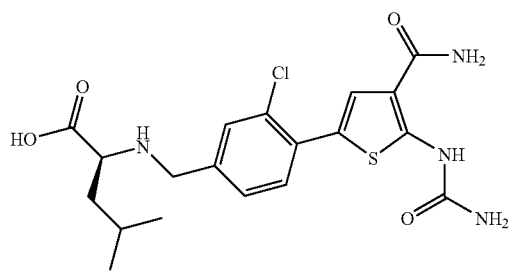

From Example 6. LC/MS purity 98%, m/z 508 [M+H]+.

Example 56

N-{4-[4-carbamoyl-5-(carbamoylamino)-2-thienyl]-2-methylbenzyl}-L-leucine

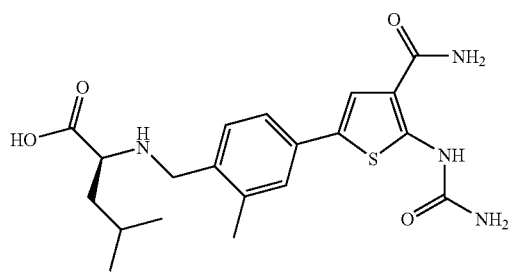

From Example 7. LCMS purity 92%, m/z 417 [M−H]+.

Example 57

N-{3-[4-Carbamoyl-5-(carbamoylamino)-2-thienyl]benzyl}-L-leucine

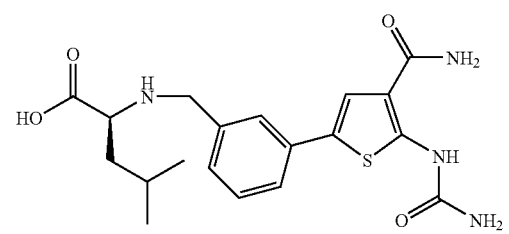

From Example 8. LC/MS purity 98%, m/z 405 [M+H]+.

The following examples were prepared in a similar manner to Example 50. Where necessary, the compounds were purified by preparative HPLC to achieve good purity.

| Example Number | Example used | $R_n$ | Name | LCMS purity |
|---|---|---|---|---|
| 58 | 9 | | (2S)-({3-[4-carbamoyl-5-(carbamoylamino)-2-thienyl]benzyl}amino)(phenyl)acetic acid | 96% purity: m/z 425 [M + H]+ |
| 59 | 10 | | (2S)-({3-[4-carbamoyl-5-(carbamoylamino)-2-thienyl]benzyl}amino)(cyclohexyl)acetic acid | 94% purity: m/z 431 [M + H]+ |
| 60 | 11 | | O-tert-butyl-N-{3-[4-carbamoyl-5-(carbamoylamino)thiophen-2-yl]benzyl}-L-serine | 100% purity: m/z 435 [M + H]+ |
| 61 | 13 | | N-{3-[4-carbamoyl-5-(carbamoylamino)thiophen-2-yl]benzyl}-L-threonine | 97% purity: m/z 393 [M + H]+ |
| 62 | 15 | | Cyclopentyl N-{3-[4-carbamoyl-5-(carbamoylamino)thiophen-2-yl]benzyl}-L-valine | 91% purity: m/z 391 [M + H]+ |

Example 63

N-(2-{4-[4-Carbamoyl-5-carbamoylamino)-2-thienyl]phenyl}ethyl)-L-leucine

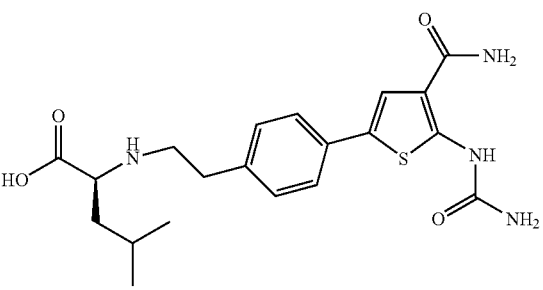

From Example 16. LC/MS purity 96%, m/z 487 [M+H]+.

Example 64

N-(2-{-4-[4-Carbamoyl-5-(carbamoylamino)-2-thienyl]-3-chlorophenyl}ethyl)-L-leucine

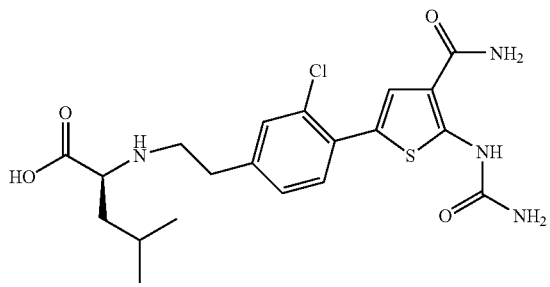

From Example 17. LC/MS purity 98%, m/z 522 [M+H]+.

Example 65

N-(3-{4-[4-Carbamoyl-5-(carbamoylamino)-2-thienyl]phenoxy}propyl)-L-leucine

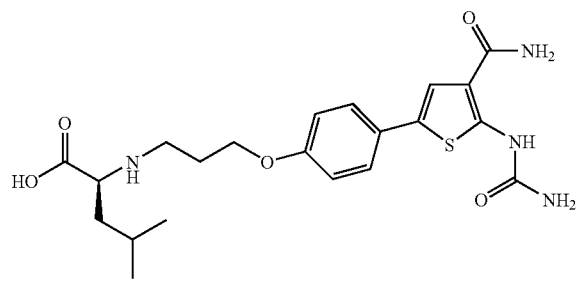

From Example 25. LC/MS purity 100%, m/z 517 [M+H]+.

Example 66

N-(3-{4-[4-Carbamoyl-5-(carbamoylamino)-2-thienyl]-3-chlorophenoxy}propyl)-L-leucine

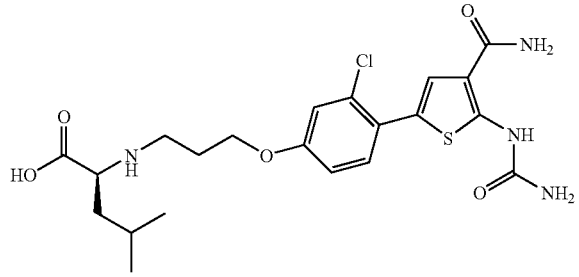

From Example 26. LC/MS purity 100%, m/z 552 [M+H]$^+$.

Example 67

N-(5-{4-[4-Carbamoyl-5-(carbamoylamino)-2-thienyl]phenoxy}pentyl-L-leucine

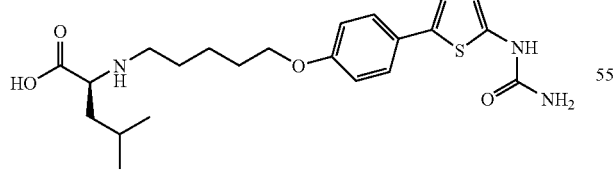

From Example 27. LC/MS purity 100%, m/z 545 [M+H]$^+$.

Example 68

N-(5-{4-[4-Carbamoyl-5-(carbamoylamino)-2-thienyl]-3-chlorophenoxy}pentyl)-L-leucine

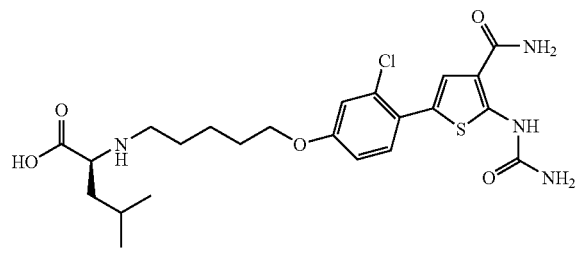

From Example 28. LC/MS purity 98%, m/z 580 [M+H]$^+$.

Example 69

N-[(2E)-3-{4-[4-Carbamoyl-5-(carbamoylamino)-2-thienyl]phenyl}prop-2-en-1-yl]-L-leucine

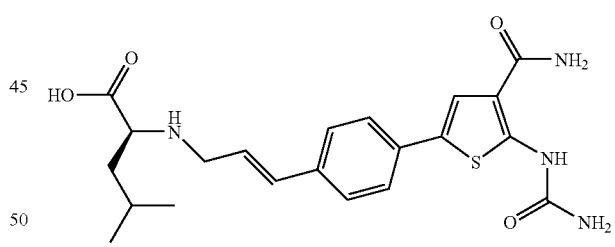

From Example 29. LCMS purity 100%, m/z 431.0 [M+H]$^+$, $^1$H NMR (400 MHz, DMSO-d$_6$), δ: 11.0 (1H, s), 7.7 (1H, s), 7.6 (1H, br s), 7.5 (2H, d, J=8.3 Hz), 7.4 (2H, d, J=8.3 Hz), 7.3 (1H, br s), 7.0 (2H, br s), 6.6 (1H, d, J=16.1 Hz), 6.2 (1H, m), 3.5 (1H, m), 3.3 (2H, m), 1.8 (1H, m), 1.4 (2H, m), 0.8 (6H, m).

The following examples were prepared in a similar manner to Example 50. Where necessary, the compounds were purified by preparative HPLC to achieve good purity.

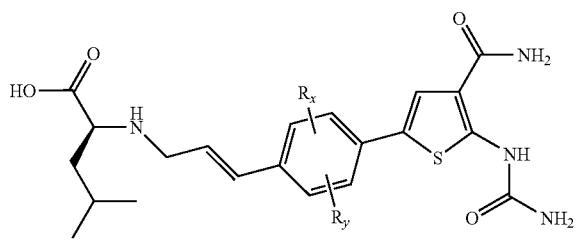

| Example Number | Example used | $R_x$ | $R_y$ | Name | LCMS purity |
|---|---|---|---|---|---|
| 70 | 30 | 2-methyl | H | N-[(2E)-3-{4-[4-carbamoyl-5-(carbamoylamino)thiophen-2-yl]-2-methylphenyl}prop-2-en-1-yl]-L-leucine | 93% purity: m/z 445 [M + H]$^+$ |
| 71 | 31 | 2-fluoro | H | N-[(2E)-3-{4-[4-carbamoyl-5-(carbamoylamino)thiophen-2-yl]-2-fluorophenyl}prop-2-en-1-yl]-L-leucine | 98% purity: m/z 449 [M + H]$^+$ |
| 72 | 32 | 2-chloro | H | N-[(2E)-3-{4-[4-carbamoyl-5-(carbamoylamino)thiophen-2-yl]-2-chlorophenyl}prop-2-en-1-yl]-L-leucine | 91% purity: m/z 466 [M + H]$^+$ |
| 73 | 33 | 3-methyl | H | N-[(2E)-3-{4-[4-carbamoyl-5-(carbamoylamino)thiophen-2-yl]-3-methylphenyl}prop-2-en-1-yl]-L-leucine | 98% purity: m/z 445 [M + H]$^+$ |
| 74 | 34 | 3-fluoro | H | N-[(2E)-3-{4-[4-carbamoyl-5-(carbamoylamino)thiophen-2-yl]-3-fluorophenyl}prop-2-en-1-yl]-L-leucine | 91% purity: m/z 449 [M + H]$^+$ |
| 75 | 35 | 3-chloro | H | N-[(2E)-3-{4-[4-carbamoyl-5-(carbamoylamino)thiophen-2-yl]-3-chlorophenyl}prop-2-en-1-yl]-L-leucine | 95% purity: m/z 466 [M + H]$^+$ |
| 76 | 36 | 2-CF$_3$ | H | N-[(2E)-3-{4-(4-carbamoyl-5-(carbamoylamino)thiophen-2-yl]-2-(trifluoromethyl)phenyl}prop-2-en-1-yl]-L-leucine | 95% purity: m/z 499 [M + H]$^+$ |
| 77 | 37 | 2-fluoro | 5-fluoro | N-[(2E)-3-{4-[4-carbamoyl-5-(carbamoylamino)thiophen-2-yl]-2,5-difluorophenyl}prop-2-en-1-yl]-L-leucine | 90% purity: m/z 467 [M + H]$^+$ |
| 78 | 38 | 2-fluoro | 6-fluoro | N-[(2E)-3-{4-[4-carbamoyl-5-(carbamoylamino)thiophen-2-yl]-2,6-difluorophenyl}prop-2-en-1-yl]-L-leucine | 93% purity: m/z 467 [M + H]$^+$ |
| 79 | 39 | 3-CF$_3$ | H | N-[(2E)-3-{4-[4-carbamoyl-5-(carbamoylamino)thiophen-2-yl]-3-(trifluoromethyl)phenyl}prop-2-en-1-yl]-L-leucine | 96% purity: m/z 499 [M + H]$^+$ |
| 80 | 40 | 2-methyl | 6-methyl | Cyclopentyl N-[(2E)-3-{4-[4-carbamoyl-5-(carbamoylamino)thiophen-2-yl]-2,6-dimethylphenyl}prop-2-en-1-yl]-L-leucine | 88% purity: m/z 459 [M + H]$^+$ |

The following examples were prepared in a similar manner to Example 50. Where necessary, the compounds were purified by preparative HPLC to achieve good purity.

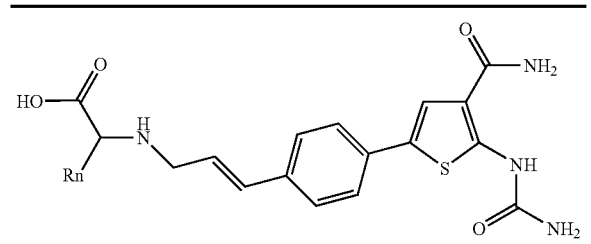

| Example Number | Example used | $R_n$ | Name | LCMS purity |
|---|---|---|---|---|
| 81 | 41 | | (2S)-{[(2E)-3-{4-[4-carbamoyl-5-(carbamoylamino)-2-thienyl]phenyl}prop-2-en-1-yl]amino}(phenyl)acetic acid | 90% purity: m/z 451 [M + H]$^+$ |
| 82 | 43 | | O-tert-butyl-N-[(2E)-3-{4-[4-carbamoyl-5-(carbamoylamino)thiophen-2-yl]phenyl}prop-2-en-1-yl]-L-serine | 98% purity: m/z 461 [M + H]$^+$ |
| 83 | 44 | | (2S)-{[(2E)-3-{4-[4-carbamoyl-5-(carbamoylamino)thiophen-2-yl]phenyl}prop-2-en-1-yl]amino}(cyclohexyl)ethanoic acid | 96% purity: m/z 456 [M + H]$^+$ |
| 84 | 46 | | N-[(2E)-3-{4-[4-carbamoyl-5-(carbamoylamino)-2-thienyl]phenyl}prop-2-en-1-yl]-D-leucine | 99% purity: m/z 431 [M + H]$^+$ |
| 85 | 47 | | Cyclopentyl O-tert-butyt-N-[(2E)-3-{4-[4-carbamoyl-5-(carbamoylamino)thiophen-2-yl]phenyl}prop-2-en-1-yl]-L-threonoine | 80% purity: m/z 475 [M + H]$^+$ |
| 86 | 48 | | Cyclopentyl N-[(2E)-3-{4-[4-carbamoyl-5-(carbamoylamino)thiophen-2-yl]phenyl}prop-2-en-1-yl]-L-threonine | 98% purity: m/z 419 [M − H]$^+$ |

Example 87

N-(2-{3-[4-carbamoyl-5-(carbamoylamino)-2-thienyl]phenyl}ethyl)-L-leucine

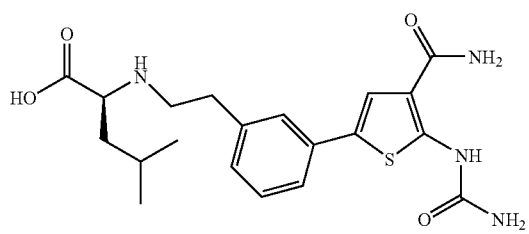

From Example 18. LCMS purity 98%, m/z 417 [M–H]$^+$.

The following examples were synthesised in a similar manner to Example 87.

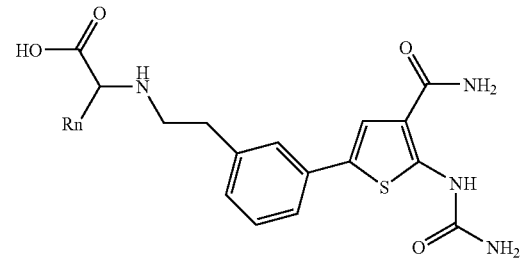

| Example Number | Example used | $R_n$ | Name | LCMS purity |
|---|---|---|---|---|
| 88 | 19 | | Cyclopentyl (2S)-[(2-{3-(4-carbamoyl-5-(carbamoylamino)-2-thienyl]phenyl}ethyl)amino](phenyl)acetic acid | 99% purity: m/z 437 [M − H]$^+$ |
| 89 | 20 | | Cyclopentyl O-tert-butyl-N-(2{3-[4-carbamoyl-5-(carbamoylamino)-2-thienyl]phenyl}ethyl)-L-serine | 91% purity: m/z 449 [M + H]$^+$ |

Example 90

N-(2-{5-[4-carbamoyl-5-(carbamoylamino)thiophen-2-yl]-2-fluorophenyl}ethyl)-L-leucine

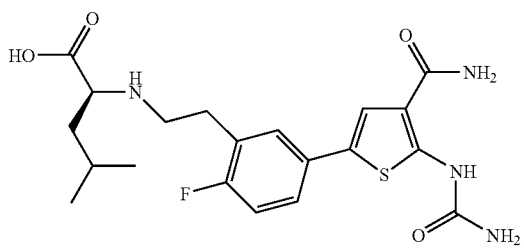

From Example 22. LCMS purity 97%, m/z 435 [M−H]+.

Example 91

Cyclopentyl N-(2-{5-[4-carbamoyl-5-(carbamoylamino)thiophen-2-yl]-2-methylphenyl}ethyl)-L-leucine

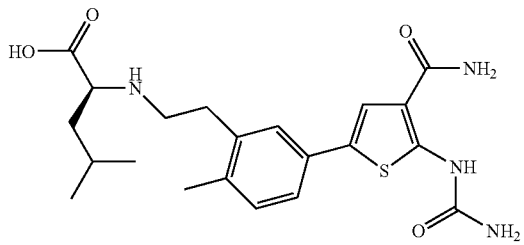

From Example 23. LCMS purity 98%, m/z 431 [M−H]+

Example 92

Cyclopentyl N-(2-{5-[4-carbamoyl-5-(carbamoylamino)thiophen-2-yl]-2-chlorophenyl}ethyl)-L-leucine

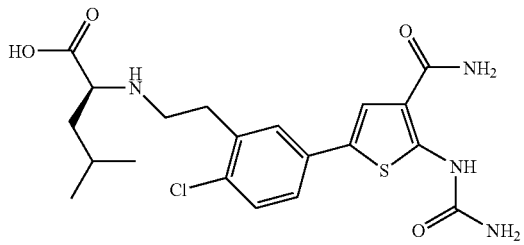

From Example 24. LCMS purity 97%, m/z 451 [M−H]+.

Example 93

N-[(2E)-3-{3-[4-carbamoyl-5-(carbamoylamino)-2-thienyl]phenyl}prop-2-en-1-yl]-L-leucine

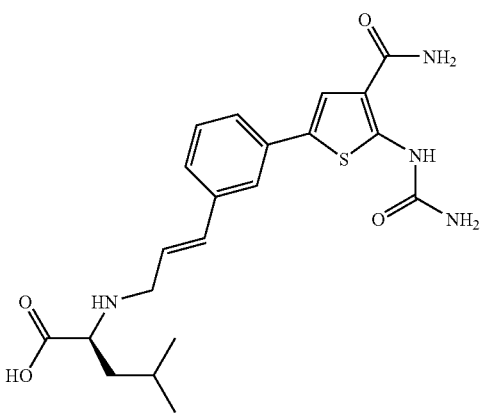

From Example 49. LC/MS purity 90%, m/z 431 [M+H]+.

Measurement of Biological Activity

IKKβ Enzyme Assay

The ability of compounds to inhibit IKKβ kinase activity was measured in an assay performed by Invitrogen (Paisley, UK). The Z'-LYTE™ biochemical assay employs a fluorescence-based, coupled-enzyme format and is based on the differential sensitivity of phosphorylated and non-phosphorylated peptides to proteolytic cleavage. The peptide substrate is labelled with two fluorophores—one at each end—that make up a FRET pair. In the primary reaction, the kinase transfers the gamma-phosphate of ATP to a single serine or threonine residue in a synthetic FRET-peptide. In the secondary reaction, a site-specific protease recognizes and cleaves non-phosphorylated FRET-peptides. Phosphorylation of FRET-peptides suppresses cleavage by the Development Reagent. Cleavage disrupts FRET between the donor (i.e., coumarin) and acceptor (i.e. fluorescein) fluorophores on the FRET-peptide, whereas uncleaved, phosphorylated FRET-peptides maintain FRET. A radiometric method, which calculates the ratio (the Emission Ratio) of donor emission to acceptor emission after excitation of the donor fluorophore at 400 nm, is used to quantitate reaction progress.

The final 10 μL Kinase Reaction consists of 0.9-8.0 ng IKBKB (IKKβ), 2 μM Ser/Thr 05 Peptide and ATP in 50 mM HEPES pH 7.5, 0.01% BRIJ-35, 10 mM MgCl$_2$, 1 mM EGTA. The assay is performed at an ATP concentration at, or close to the Km. After the 60 minute Kinase Reaction incubation at room temperature, 5 μL of a 1:128 dilution of Development Reagent is added. The assay plate is incubated for a further 60 minutes at room temperature and read on a fluorescence plate reader.

Duplicate data points are generated from a ⅓ log dilution series of a stock solution of test compound in DMSO. Nine dilutions steps are made from a top concentration of 10 μM, and a 'no compound' blank is included. Data is collected and analysed using XLfit software from IDBS. The dose response curve is curve fitted to model number 205 (sigmoidal dose-response model). From the curve generated, the concentration giving 50% inhibition is determined and reported.

LPS-Stimulation of THP-1 Cells

THP-1 cells were plated in 100 µl at a density of $4\times10^4$ cells/well in V-bottomed 96 well tissue culture treated plates and incubated at 37° C. in 5% $CO_2$ for 16 hrs. 2 hrs after the addition of the inhibitor in 100 µl of tissue culture media, the cells were stimulated with LPS (*E. coli* strain 005:85, Sigma) at a final concentration of 1 µg/ml and incubated at 37° C. in 5% $CO_2$ for 6 hrs. TNF-α levels were measured from cell-free supernatants by sandwich ELISA (R&D Systems #QTA00B)

LPS-Stimulation of Human Whole Blood

Whole blood was taken by venous puncture using heparinised vacutainers (Becton Dickinson) and diluted in an equal volume of RPMI1640 tissue culture media (Sigma). 100 µl was plated in V-bottomed 96 well tissue culture treated plates. 2 hrs after the addition of the inhibitor in 100 µl of RPMI1640 media, the blood was stimulated with LPS (*E. coli* strain 005:B5, Sigma) at a final concentration of 100 ng/ml and incubated at 37° C. in 5% $CO_2$ for 6 hrs. TNF-α levels were measured from cell-free supernatants by sandwich ELISA (R&D Systems #QTA00B)

$IC_{50}$ values were allocated to one of three ranges as follows:

Range A: IC50<1000 nM
Range B: 1000 nM<IC50<5000 nM
Range C: IC50>5000 nM
NT=not tested Results Table

| Example Number | Inhibitor activity versus IKKβ | Inhibitor activity versus THP-1 TNFα release | Inhibitor activity versus human whole blood TNFα release |
|---|---|---|---|
| 1 | B | B | B |
| 2 | A | C | B |
| 3 | C | C | NT |
| 4 | A | C | B |
| 5 | C | C | NT |
| 6 | A | C | NT |
| 7 | A | B | NT |
| 8 | A | A | B |
| 9 | A | A | B |
| 10 | B | A | B |
| 11 | A | B | B |
| 12 | A | NT | A |
| 13 | A | A | A |
| 14 | A | A | B |
| 15 | NT | NT | B |
| 16 | B | B | NT |
| 17 | B | C | NT |
| 18 | B | A | B |
| 19 | A | A | A |
| 20 | NT | NT | B |
| 21 | NT | NT | C |
| 22 | B | B | B |
| 23 | NT | NT | C |
| 24 | NT | NT | C |
| 25 | B | B | NT |
| 26 | B | B | NT |
| 27 | A | B | NT |
| 28 | C | B | NT |
| 29 | A | A | A |
| 30 | B | B | NT |
| 31 | B | B | B |
| 32 | B | A | B |
| 33 | C | A | B |
| 34 | A | B | NT |
| 35 | B | B | NT |
| 36 | B | C | NT |
| 37 | B | B | NT |
| 38 | C | NT | B |
| 39 | C | NT | B |
| 40 | NT | NT | NT |
| 41 | A | B | B |
| 42 | A | B | C |
| 43 | A | NT | B |
| 44 | A | NT | C |
| 45 | A | NT | C |
| 46 | A | NT | B |
| 47 | NT | NT | C |
| 48 | NT | NT | B |
| 49 | A | A | A |
| 50 | A | NT | NT |
| 51 | A | NT | NT |
| 52 | A | NT | NT |
| 53 | A | NT | NT |
| 54 | A | NT | NT |
| 55 | A | NT | NT |
| 56 | A | NT | NT |
| 57 | A | NT | NT |
| 58 | A | NT | NT |
| 59 | A | NT | NT |
| 60 | A | NT | NT |
| 61 | A | NT | NT |
| 62 | NT | NT | NT |
| 63 | A | NT | NT |
| 64 | A | NT | NT |
| 65 | A | NT | NT |
| 66 | A | NT | NT |
| 67 | A | NT | NT |
| 68 | A | NT | NT |
| 69 | A | NT | NT |
| 70 | A | NT | NT |
| 71 | A | NT | NT |
| 72 | A | NT | NT |
| 73 | A | NT | NT |
| 74 | A | NT | NT |
| 75 | A | NT | NT |
| 76 | A | NT | NT |
| 77 | A | NT | NT |
| 78 | A | NT | NT |
| 79 | B | NT | NT |
| 80 | A | NT | NT |
| 81 | A | NT | NT |
| 82 | A | NT | NT |
| 83 | A | NT | NT |
| 84 | A | NT | NT |
| 85 | NT | NT | NT |
| 86 | NT | NT | NT |
| 87 | A | NT | NT |
| 88 | A | NT | NT |
| 89 | NT | NT | NT |
| 90 | A | NT | NT |
| 91 | NT | NT | NT |
| 92 | NT | NT | NT |
| 93 | A | NT | NT |

Broken Cell Carboxylesterase Assay

Any given compound of the present invention wherein $R_1$ is an ester group, may be tested to determine whether it meets the requirement that it be hydrolysed by intracellular esterases, by testing in the following assay.

Preparation of Cell Extract

U937 or HCT 116 tumour cells ($\sim10^9$) were washed in 4 volumes of Dulbeccos PBS (~1 litre) and pelleted at 525 g for 10 min at 4° C. This was repeated twice and the final cell pellet was resuspended in 35 ml of cold homogenising buffer (Trizma 10 mM, NaCl 130 mM, $CaCl_2$ 0.5 mM pH 7.0 at 25° C.). Homogenates were prepared by nitrogen cavitation (700 psi for 50 min at 4° C.). The homogenate was kept on ice and supplemented with a cocktail of inhibitors at final concentrations of:

Leupeptin 1 µM
Aprotinin 0.1 µM
E64 8 µM

Pepstatin 1.5 μM
Bestatin 162 μM
Chymostatin 33 μM

After clarification of the cell homogenate by centrifugation at 525 g for 10 min, the resulting supernatant was used as a source of esterase activity and was stored at −80° C. until required.

Measurement of Ester Cleavage

Hydrolysis of esters to the corresponding carboxylic acids can be measured using the cell extract, prepared as above. To this effect cell extract (~30 μg/total assay volume of 0.5 ml) was incubated at 37° C. in a Tris-HCl 25 mM, 125 mM NaCl buffer, pH 7.5 at 25° C. At zero time the ester (substrate) was then added at a final concentration of 2.5 μM and the samples were incubated at 37° C. for the appropriate time (usually 0 or 80 min). Reactions were stopped by the addition of 3× volumes of acetonitrile. For zero time samples the acetonitrile was added prior to the ester compound. After centrifugation at 12000 g for 5 min, samples were analysed for the ester and its corresponding carboxylic acid at room temperature by LCMS (Sciex API 3000, HP1100 binary pump, CTC PAL). Chromatography was based on an AcCN (75×2.1 mm) column and a mobile phase of 5-95% acetonitrile in water/0.1% formic acid.

Table 1 presents data showing that several amino acid ester motifs, conjugated to various intracellular enzyme inhibitors by several different linker chemistries are all hydrolysed by intracellular carboxyesterases to the corresponding acid.

TABLE 1

| Structure of amino acid ester conjugate | R | Linker | Hydrolysis Rate Range U937 Cells (pg/mL/min) | Preparation of amino ester conjugate |
|---|---|---|---|---|
| [structure] | [cyclopentyl ester structure] | —CH2CH2O— | 100-1000 | WO2006117552 |
| [structure] | [cyclopentyl ester structure] | —(CH2)3O—[phenyl]—CH2NHCH2— | 1000-50000 | WO2006117548 |
| [structure] | [cyclopentyl ester with leucine structure] | —CH2—[phenyl]—CH2NHCH2— | >50000 | WO2006117549 |
| [structure] | [cyclopentyl ester structure] | —CH2CH2O— | >500000 | WO2006117567 |
| [structure] | [cyclopentyl ester with cyclohexylamino structure] | —CH2CH2O— | 1000-50000 | WO2006117567 |

TABLE 1-continued

| Structure of amino acid ester conjugate | R | Linker | Hydrolysis Rate Range of U937 Cells (pg/mL/min) | Preparation of amino ester conjugate |
|---|---|---|---|---|
| (structure) | (structure) | —CH2— | 1000-50000 | WO2006117567 |
| (structure) | (structure) | —CO— | >50000 | WO2006117567 |
| (structure) | (structure) | —CH2—(phenyl)—CH2NHCH2— | >50000 | WO2006117549 |
| (structure) | (structure) | —CH2—(phenyl)—CH2NHCH2— | >50000 | WO2006117549 |

The invention claimed is:

1. A compound of formula (IA) or (IB), or a salt or N-oxide thereof:

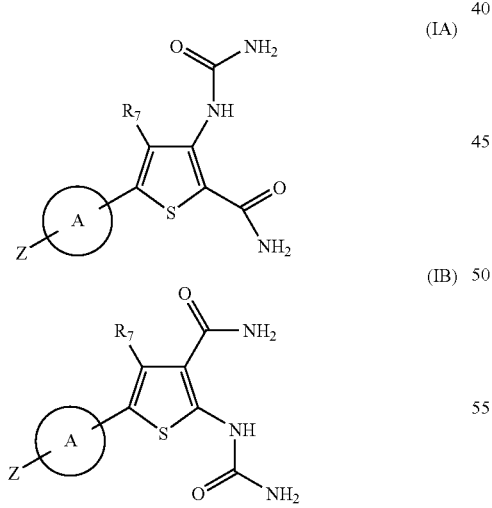

wherein $R_7$ is hydrogen or optionally substituted $(C_1\text{-}C_6)$alkyl;

ring A is an optionally substituted aryl;

Z is (a) a radical of formula $R_1R_2CHNH\text{—}Y\text{-}L^1\text{-}X^1\text{—}(CH_2)_z\text{—}$ wherein:

$R_1$ is a carboxylic acid group (—COOH), or an ester group which is hydrolysable by one or more intracellular esterase enzymes to a carboxylic acid group of formula —(C=O)$OR_{14}$ wherein $R_{14}$ is $R_8R_9R_{10}C$— wherein (i) $R_8$ is hydrogen or optionally substituted $(C_1\text{-}C_3)$alkyl-$(Z^1)_a$-$[(C_1\text{-}C_3)\text{alkyl}]_b$- or $(C_2\text{-}C_3)$alkenyl-$(Z^1)_a$-$[(C_1\text{-}C_3)\text{alkyl}]_b$- wherein a and b are independently 0 or 1 and $Z^1$ is —O—, —S—, or —$NR_{11}$— wherein $R_{11}$ is hydrogen or $(C_1\text{-}C_3)$alkyl; and $R_9$ and $R_{10}$ are independently hydrogen or $(C_1\text{-}C_3)$alkyl-;

(ii) $R_8$ is hydrogen or optionally substituted $R_{12}R_{13}N$—$(C_1\text{-}C_3)$alkyl- wherein $R_{12}$ is hydrogen or $(C_1\text{-}C_3)$alkyl and $R_{13}$ is hydrogen or $(C_1\text{-}C_3)$alkyl; or $R_{12}$ and $R_{13}$ together with the nitrogen to which they are attached form an optionally substituted monocyclic heterocyclic ring of 5- or 6-ring atoms or bicyclic heterocyclic ring system of 8 to 10 ring atoms, and $R_9$ and $R_{10}$ are independently hydrogen or $(C_1\text{-}C_3)$alkyl-; or (iii) $R_8$ and $R_9$ taken together with the carbon to which they are attached form an optionally substituted monocyclic carbocyclic ring of from 3 to 7 ring atoms or bicyclic carbocyclic ring system of 8 to 10 ring atoms, and $R_{10}$ is hydrogen;

$R_2$ is the side chain of a natural or non-natural alpha amino acid $(C_1\text{-}C_6)$alkyl, phenyl, 2-, 3-, or 4-hydroxyphenyl, 2-, 3-, or 4-methoxyphenyl, 2-, 3-, or 4-pyridylmethyl, benzyl, phenylethyl, 2-, 3-, or 4-hydroxybenzyl, 2-, 3-, or 4-benzyloxybenzyl, 2-, 3-, or 4-$(C_1\text{-}C_6)$alkoxybenzyl, and benzyloxy$(C_1\text{-}C_6\text{alkyl})$-groups;

the characterising group of a natural α amino acid, in which any functional group may be protected;

groups -[Alk]$_n$R$_{16}$ where Alk is a (C$_1$-C$_6$)alkyl or (C$_2$-C$_6$)alkenyl group optionally interrupted by one or more —O—, or —S— atoms or —N(R$_{17}$)— groups where R$_{17}$ is a hydrogen atom or a (C$_1$-C$_6$)alkyl group, n is 0 or 1, and R$_{16}$ is an optionally substituted cycloalkyl or cycloalkenyl group;

a benzyl group substituted in the phenyl ring by a group of formula —OCH$_2$COR$_{18}$ where R$_{18}$ is hydroxyl, amino, (C$_1$-C$_6$)alkoxy, phenyl(C$_1$-C$_6$)alkoxy, (C$_1$-C$_6$)alkylamino, di((C$_1$-C$_6$)alkyl)amino, phenyl(C$_1$-C$_6$)alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid;

a heterocyclic(C$_1$-C$_6$)alkyl group, either being unsubstituted or mono- or di-substituted in the heterocyclic ring with halo, nitro, carboxy, (C$_1$-C$_6$)alkoxy, cyano, (C$_1$-C$_6$)alkanoyl, trifluoromethyl (C$_1$-C$_6$)alkyl, hydroxy, formyl, amino, (C$_1$-C$_6$)alkylamino, di-(C$_1$-C$_6$)alkylamino, mercapto, (C$_1$-C$_6$)alkylthio, hydroxy (C$_1$-C$_6$)alkyl, mercapto(C$_1$-C$_6$)alkyl or (C$_1$-C$_6$)alkylphenylmethyl; and a group —CR$_a$R$_b$R$_c$, in which:
each of R$_a$, R$_b$ and R$_c$ is independently hydrogen, (C$_1$-C$_6$)alkyl, (C$_2$-C$_6$)alkenyl, (C$_2$-C$_6$)alkynyl, phenyl(C$_1$-C$_6$)alkyl, (C$_3$-C$_8$)cycloalkyl; or R$_c$ is hydrogen and R$_a$ and R$_b$ are independently phenyl or heteroaryl such as pyridyl; or R$_c$ is hydrogen, (C$_1$-C$_6$)alkyl, (C$_2$-C$_6$)alkenyl, (C$_2$-C$_6$)alkynyl, phenyl(C$_1$-C$_6$)alkyl, or (C$_3$-C$_8$)cycloalkyl, and R$_a$ and R$_b$ together with the carbon atom to which they are attached form a 3 to 8 membered cycloalkyl or a 5- to 6-membered heterocyclic ring; or R$_a$, R$_b$ and R$_c$ together with the carbon atom to which they are attached form a tricyclic ring; or R$_a$ and R$_b$ are each independently (C$_1$-C$_6$)alkyl, (C$_2$-C$_6$)alkenyl, (C$_2$-C$_6$)alkynyl, phenyl(C$_1$-C$_6$)alkyl, or a group as defined for R$_c$ below other than hydrogen, or R$_a$ and R$_b$ together with the carbon atom to which they are attached form a cycloalkyl or heterocyclic ring, and R$^c$, is hydrogen, —OH, —SH, halogen, —CN, —CO$_2$H, (C$_1$-C$_4$)perfluoroalkyl, —CH$_2$OH, —CO$_2$(C$_1$-C$_6$)alkyl, —O(C$_1$-C$_6$)alkyl, —O(C$_2$-C$_6$)alkenyl, —S(C$_1$-C$_6$)alkyl, —SO(C$_1$-C$_6$)alkyl, —SO$_2$(C$_1$-C$_6$)alkyl, —S(C$_2$-C$_6$)alkenyl, —SO(C$_2$-C$_6$)alkenyl, —SO$_2$(C$_2$-C$_6$)alkenyl or a group -Q-W wherein Q represents a bond or —O—, —S—, —SO— or —SO$_2$— and W represents a phenyl, (C$_3$-C$_8$)cycloalkyl, (C$_3$-C$_8$)cycloalkylalkyl, (C$_4$-C$_8$)cycloalkenyl, (C$_4$-C$_a$)cycloalkenylalkyl, heteroaryl or heteroarylalkyl group, which group W may optionally be substituted by one or more substituents independently selected from, hydroxyl, halogen, —CN, —CO$_2$H, —CO$_2$(C$_1$-C$_6$)alkyl, —CONH$_2$, —CONH(C$_1$-C$_6$) alkyl, —CONH(C$_1$-C$_6$alkyl)$_2$, —CHO, —CH$_2$OH, (C$_1$-C$_4$)perfluoroalkyl, —S(C$_1$-C$_6$) alkyl, —SO(C$_1$-C$_6$)alkyl, —SO$_2$(C$_1$-C$_6$)alkyl, —NO$_2$, —NH$_2$, —NH(C$_1$-C$_6$)alkyl, NHCO(C$_1$-C$_6$) alkyl, (C$_1$-C$_6$)alkyl, (C$_2$-C$_6$)alkenyl, (C$_7$-C$_6$)alkynyl, (C$_3$-C$_8$)cycloalkyl, (C$_4$-C$_8$)cycloalkenyl, phenyl or benzyl;

Y is a bond, —C(=O)—, —S(=O)$_2$—, —C(=O)O—, —C(=O)NR$_3$—, —C(=S)—NR$_3$, —C(=NH)—NR$_3$ or —S(=O)$_2$NR$_3$— wherein R$_3$ is hydrogen or optionally substituted C$_1$-C$_6$ alkyl;

L$^1$ is a divalent radical of formula -(Alk$^1$)$_m$(Q)$_n$(Alk$^2$)$_p$- wherein
m, n and p are independently 0 or 1,
Q is (i) an optionally substituted divalent mono- or bicyclic carbocyclic or heterocyclic radical having 5-13 ring members, or (ii), in the case where p is 0, a divalent radical of formula -Q$^1$-X$^2$— wherein X$^2$ is —O—, —S— or NR$^A$— wherein R$^A$ is hydrogen or optionally substituted C$_1$-C$_3$ alkyl, and Q$^1$ is an optionally substituted divalent mono- or bicyclic carbocyclic or heterocyclic radical having 5-13 ring members, Alk$^1$ and Alk$^2$ independently represent optionally substituted divalent C$_3$-C$_7$ cycloalkyl radicals, or optionally substituted straight or branched, C$_1$-C$_6$ alkylene, C$_2$-C$_6$ alkenylene, or C$_2$-C$_6$ alkynylene radicals which may optionally contain or terminate in an ether (—O—), thioether (—S—) or amino (—NR$^A$—) link wherein R$^A$ is hydrogen or optionally substituted C$_1$-C$_3$ alkyl;

X$^1$ is a bond, —C(=O)—; or —S(=O)$_2$—; —NR$_4$C (=O)—, —C(=O)NR$_4$—, —NR$_4$C(=O)—NR$_5$—, —NR$_4$S(=O)$_2$—, or —S(=O)$_2$NR$_4$— wherein R$_4$ and R$_5$ are independently hydrogen or optionally substituted C$_1$-C$_6$ alkyl; and z is 0 or 1.

2. A compound as claimed in claim 1 wherein R$_7$ is hydrogen.

3. A compound as claimed in claim 1 wherein ring A is optionally substituted 1,4-phenylene or 1,3-phenylene.

4. A compound as claimed in claim 1 wherein optional substituents in ring A are selected from, fluoro, chloro, methyl, and trifluoromethyl.

5. A compound as claimed in claim 1 wherein R$_1$ is a methyl, ethyl, n- or iso-propyl, n-, sec- or tert-butyl, cyclohexyl, allyl, phenyl, benzyl, 2-, 3- or 4-pyridylmethyl, N-methylpiperidin-4-yl, tetrahydrofuran-3-yl, methoxyethyl, indanyl, norbornyl, dimethylaminoethyl, or morpholinoethyl ester group.

6. A compound as claimed in claim 1 wherein R$_1$ is a cyclopentyl, or tert-butyl ester group.

7. A compound as claimed in claim 1 wherein R$_2$ is cyclohexylmethyl, cyclohexyl, pyridin-3-ylmethyl, sec-butyl, tert-butyl, 1-benzylthio-1-methylethyl, 1-methylthio-1-methylethyl, or 1-mercapto-1-methylethyl.

8. A compound as claimed in claim 1 wherein R$_2$ is phenyl, benzyl, phenylethyl, cyclohexyl, tert-butoxymethyl or isobutyl.

9. A compound as claimed in claim 1 wherein the radical R$_1$R$_2$CHNH—Y-L$^1$X$^1$—(CH$_2$)$_z$— is selected from R$_1$R$_2$CHNH—(CH$_2$)$_a$—, R$_1$R$_2$CHNH—(CH$_2$)$_a$O—, and R$_1$R$_2$CHNH—CH$_2$CH=CHCH$_2$—, wherein a is 1, 2, 3, 4 or 5.

10. A compound as claimed in claim 1 selected from the group consisting of
Cyclopentyl N-{4-[4-carbamoyl-5-(carbamoylamino)-2-thienyl]benzyl}-L-leucinate,
Cyclopentyl N-{3-[4-carbamoyl-5-(carbamoylamino)-2-thienyl]benzyl}-L-leucinate,
Cyclopentyl N-{4-[4-carbamoyl-5-(carbamoylamino)-2-thienyl]-3-chlorobenzyl}-L-leucinate,
Cyclopentyl N-[(2E)-3-{4-[4-carbamoyl-5-(carbamoylamino)-2-thienyl]phenyl}prop-2-en-1-yl]-L-leucinate, Cyclopentyl (2S)-{[(2E)-3-{4-[4-carbamoyl-5-(carbamoylamino)-2-thienyl]phenyl}prop-2-en-1-yl]amino}(phenyl)acetate Cyclopentyl (2S)-({3-[4-carbamoyl-5-(carbamoylamino)-2-thienyl]benzyl}amino)(phenyl)acetate Cyclopentyl N-[(2E)-3-{4-[4-carbamoyl-5-(carbamoylamino)thiophen-2-yl]-3-methylphenyl}prop-2-en-1-yl]-L-leucinate Cyclopentyl (2S)-[(2-{3-[4-carbamoyl-5-(carbamoylamino)-2-thienyl]phenyl}ethyl)amino](phenyl)acetate Cyclopentyl N-{3-[4-carbamoyl-5-(carbamoylamino)thiophen-2-yl]benzyl}-L-threoninate Cyclopentyl (2S)-({3-[4-carbamoyl-5-(carbamoylamino)-2-thienyl]benzyl}amino)(cyclohexyl)acetate Cyclopentyl N-[(2E)-3-{3-[4-carbamoyl-5-(carbamoylamino)-2-thienyl]phenyl}prop-2-en-1-yl]-L-leucinate, tert-Butyl N-{3-[4-carbamoyl-5-(carbamoylamino)-2-thienyl]benzyl}-L-leucinate, and Cyclopentyl N-(2-{3-[4-carbamoyl-5-(carbamoylamino)-2-thienyl]phenyl}ethyl)-L-leucinate, and salts or N-oxides thereof.

11. A pharmaceutical composition comprising a compound as claimed in claim 1 together with one or more pharmaceutically acceptable carriers and/or excipients.

* * * * *

UNITED STATES PATENT AND TRADEMARK OFFICE
CERTIFICATE OF CORRECTION

PATENT NO. : 8,003,695 B2
APPLICATION NO. : 12/513206
DATED : August 23, 2011
INVENTOR(S) : David Festus Charles Moffat et al.

It is certified that error appears in the above-identified patent and that said Letters Patent is hereby corrected as shown below:

Title Page, Item 57, In the abstract, line 12:
 Please delete "-S(=P)2-" and insert -- –S(=O)2- --

Title Page, Item 57, In the abstract, line 14:
 Please delete "L" and insert -- $L^1$ --

Column 92, Claim 1, Line 66:
 Please delete "natural a amino acid" and insert -- natural α amino acid --

Column 93, Claim 1, Line 54:
 Please insert -- phenylalkyl -- after the word phenyl Column 93, Claim 1, Line 55:
 Please delete "($C_4$ - $C_\alpha$)" and insert -- ($C_4$ – $C_8$) --

Column 93, Claim 1, Line 62:
 Please insert -- -O($C_1$ – $C_6$)alkyl -- after the phrase ($C_1$ – $C_4$)perfluoroalkyl, Column 93, Claim 1, Line 64:
 Please insert -- -N(($C_1$ – $C_6$)alkyl)$_2$, -- after the phrase –NH($C_1$ – $C_6$)alkyl, Column 93, Claim 1, Line 65:
 Please delete "($C_7$ – $C_6$)alkynyl" and insert -- ($C_2$ – $C_6$)alkynyl --

Signed and Sealed this
Twenty-sixth Day of June, 2012

David J. Kappos
*Director of the United States Patent and Trademark Office*